(12) United States Patent
Berry et al.

(10) Patent No.: US 9,944,902 B2
(45) Date of Patent: Apr. 17, 2018

(54) COMMERCIAL SCALE PROCESS FOR PRODUCTION OF PRRSV

(75) Inventors: Elizabeth Jane Berry, St. Joseph, MO (US); Fuad Tawfiq Haddadin, St. Joseph, MO (US); Ali Khazraeinazmpour, St. Joseph, MO (US); Jeremy Kroll, Urbandale, IA (US); Sonia Regina Cantisano Malburg, Platte City, MO (US); Edgar Arnulfo Sandoval Basurto, St. Joseph, MO (US); Stephen Scheerer, St. Joseph, MO (US)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 727 days.

(21) Appl. No.: 13/396,318

(22) Filed: Feb. 14, 2012

(65) Prior Publication Data

US 2012/0213741 A1 Aug. 23, 2012

Related U.S. Application Data

(60) Provisional application No. 61/444,071, filed on Feb. 17, 2011.

(51) Int. Cl.
| | | |
|---|---|---|
| *A01N 63/00* | (2006.01) | |
| *C12N 7/00* | (2006.01) | |
| *C12N 7/01* | (2006.01) | |
| *C12N 7/02* | (2006.01) | |
| *A61K 39/12* | (2006.01) | |
| *A61K 39/00* | (2006.01) | |

(52) U.S. Cl.
CPC ............... *C12N 7/00* (2013.01); *A61K 39/12* (2013.01); *C12N 7/02* (2013.01); *A61K 2039/552* (2013.01); *C12N 2770/10021* (2013.01); *C12N 2770/10034* (2013.01); *C12N 2770/10051* (2013.01)

(58) Field of Classification Search
None
See application file for complete search history.

(56) References Cited

U.S. PATENT DOCUMENTS

| | | |
|---|---|---|
| 3,137,631 A | 6/1964 | Soloway |
| 3,959,457 A | 5/1976 | Speaker et al. |
| 4,015,100 A | 3/1977 | Gnanamuthu et al. |
| 4,122,167 A | 10/1978 | Buynak et al. |
| 4,205,060 A | 5/1980 | Monsimer et al. |
| 4,224,412 A | 9/1980 | Dorofeev et al. |
| 4,452,747 A | 6/1984 | Gersonde et al. |
| 4,468,346 A | 8/1984 | Paul et al. |
| 4,554,159 A | 11/1985 | Roizman et al. |
| 4,606,940 A | 8/1986 | Frank et al. |
| 4,636,485 A | 1/1987 | van der Smissen |
| 4,744,933 A | 5/1988 | Rha et al. |
| 4,753,884 A | 6/1988 | Kit et al. |
| 4,810,493 A | 3/1989 | Patrick et al. |
| 4,921,706 A | 5/1990 | Roberts et al. |
| 4,927,637 A | 5/1990 | Morano et al. |
| 4,944,948 A | 7/1990 | Uster et al. |
| 5,008,050 A | 4/1991 | Cullis et al. |
| 5,009,956 A | 4/1991 | Baumann |
| 5,132,117 A | 7/1992 | Speaker et al. |
| 5,206,163 A | 4/1993 | Renard et al. |
| 5,213,759 A | 5/1993 | Castberg et al. |
| 5,419,907 A | 5/1995 | Paul et al. |
| 5,476,778 A | 12/1995 | Chladek et al. |
| 5,510,258 A | 4/1996 | Sanderson et al. |
| 5,587,164 A | 12/1996 | Sanderson et al. |
| 5,597,721 A | 1/1997 | Brun et al. |
| 5,620,691 A | 4/1997 | Wensvoort et al. |
| 5,674,500 A | 10/1997 | Peeters et al. |
| 5,677,429 A | 10/1997 | Benfield |
| 5,683,865 A | 11/1997 | Collins et al. |
| 5,690,940 A | 11/1997 | Joo |
| 5,695,766 A | 12/1997 | Paul et al. |
| 5,698,203 A | 12/1997 | Visser et al. |
| 5,789,388 A | 8/1998 | Visser et al. |
| 5,840,563 A | 11/1998 | Chladek et al. |
| 5,846,805 A | 12/1998 | Collins et al. |
| 5,858,729 A | 1/1999 | Van Woensel et al. |
| 5,866,401 A | 2/1999 | Hesse |
| 5,888,513 A | 3/1999 | Plana Duran et al. |
| 5,910,310 A | 6/1999 | Heinen et al. |
| 5,925,359 A | 7/1999 | Van Woensel et al. |
| 5,968,525 A | 10/1999 | Fitzgerald et al. |
| 5,976,537 A | 11/1999 | Mengeling et al. |
| 5,989,563 A | 11/1999 | Chladek et al. |
| 5,998,601 A | 12/1999 | Murtaugh et al. |

(Continued)

FOREIGN PATENT DOCUMENTS

| | | |
|---|---|---|
| CA | 2103460 A1 | 12/1992 |
| DE | 145705 A1 | 1/1981 |

(Continued)

OTHER PUBLICATIONS

Tiscornia et al., Nature Protocols, vol. 1, No. 1, 241-245 (2006).*
Srcek et al., Cytotechnology 45:101-106 (2004).*
Tree et al., Vaccine 19:3444-3450 (2001).*
Fox et al., Biotechnol. Bioengin., vol. 85, No. 2 (2004).*
Meuwly et al., J. Biotechnol. 122:122-129 (2006).*
Namdev et al. Wave Biotech (2000).*
Slivac et al.,J. Biosci., 31(3), 363-368 (2006).*
Rourou et al., Vaccine, 25:3879-3889 (2007).*

(Continued)

*Primary Examiner* — Thomas J. Visone

(74) *Attorney, Agent, or Firm* — Marc Began; Joyce L. Morrison

(57) ABSTRACT

The present invention describes an efficient commercial scale production method for the preparation of PRRS virus.

16 Claims, 8 Drawing Sheets

(56) References Cited

U.S. PATENT DOCUMENTS

| | | |
|---|---|---|
| 6,001,370 A | 12/1999 | Burch et al. |
| 6,015,663 A | 1/2000 | Wesley et al. |
| 6,042,830 A | 3/2000 | Chladek et al. |
| 6,080,570 A | 6/2000 | Chladek et al. |
| 6,110,467 A | 8/2000 | Paul et al. |
| 6,110,468 A | 8/2000 | Collins et al. |
| 6,149,917 A * | 11/2000 | Fanget et al. ............... 424/218.1 |
| 6,194,210 B1 * | 2/2001 | Leu et al. ...................... 435/403 |
| 6,197,310 B1 | 3/2001 | Wensvoort et al. |
| 6,241,990 B1 | 6/2001 | Collins et al. |
| 6,251,397 B1 | 6/2001 | Paul et al. |
| 6,251,404 B1 | 6/2001 | Paul et al. |
| 6,268,199 B1 | 7/2001 | Meulenberg et al. |
| 6,380,376 B1 | 4/2002 | Paul et al. |
| 6,391,314 B1 | 5/2002 | Allan et al. |
| 6,455,245 B1 | 9/2002 | Wensvoort et al. |
| 6,495,138 B1 | 12/2002 | van Nieuwstadt et al. |
| 6,498,008 B2 | 12/2002 | Collins et al. |
| 6,500,662 B1 | 12/2002 | Calvert et al. |
| 6,592,873 B1 | 7/2003 | Paul et al. |
| 6,641,819 B2 | 11/2003 | Mengeling et al. |
| 6,660,513 B2 | 12/2003 | Mengeling et al. |
| 6,773,908 B1 | 8/2004 | Paul et al. |
| 6,806,086 B2 | 10/2004 | Wensvoort et al. |
| 6,841,364 B2 | 1/2005 | Yuan et al. |
| 6,855,315 B2 | 2/2005 | Collins et al. |
| 6,982,160 B2 | 1/2006 | Collins et al. |
| 7,018,638 B2 | 3/2006 | Chu et al. |
| 7,081,342 B2 | 7/2006 | Mengeling et al. |
| 7,109,025 B1 | 9/2006 | Eloit et al. |
| 7,122,347 B2 | 10/2006 | Verheije et al. |
| 7,132,106 B2 | 11/2006 | Calvert et al. |
| 7,169,394 B2 | 1/2007 | Chu et al. |
| 7,211,379 B2 | 5/2007 | Ellis et al. |
| 7,232,680 B2 | 6/2007 | Calvert et al. |
| 7,264,804 B2 | 9/2007 | Collins et al. |
| 7,273,617 B2 | 9/2007 | Yuan et al. |
| 7,312,030 B2 | 12/2007 | van Rijn et al. |
| 7,335,361 B2 | 2/2008 | Liao et al. |
| 7,335,473 B2 | 2/2008 | Wensvoort et al. |
| 7,368,117 B2 | 5/2008 | Fetzer et al. |
| 7,618,797 B2 | 11/2009 | Calvert et al. |
| 7,632,636 B2 | 12/2009 | Roof et al. |
| 7,691,389 B2 | 4/2010 | Calvert et al. |
| 7,722,878 B2 | 5/2010 | Vaughn et al. |
| 7,897,343 B2 | 3/2011 | Wensvoort et al. |
| 2002/0012670 A1 | 1/2002 | Elbers et al. |
| 2002/0098573 A1 | 7/2002 | Meulenberg et al. |
| 2002/0172690 A1 | 11/2002 | Calvert et al. |
| 2003/0049274 A1 | 3/2003 | Meulenberg et al. |
| 2003/0118608 A1 | 6/2003 | Wensvoort et al. |
| 2003/0157689 A1 | 8/2003 | Calvert et al. |
| 2003/0219732 A1 | 11/2003 | van Rijn et al. |
| 2004/0009190 A1 | 1/2004 | Elbers et al. |
| 2004/0132014 A1 | 7/2004 | Wensvoort et al. |
| 2004/0197872 A1 | 10/2004 | Meulenberg et al. |
| 2004/0213805 A1 | 10/2004 | Verheije |
| 2004/0224327 A1 | 11/2004 | Meulenberg et al. |
| 2004/0253270 A1 | 12/2004 | Meng et al. |
| 2006/0063151 A1 | 3/2006 | Roof et al. |
| 2006/0205033 A1 | 9/2006 | Meulenberg et al. |
| 2006/0240041 A1 | 10/2006 | Meulenberg et al. |
| 2006/0286123 A1 | 12/2006 | Fetzer et al. |
| 2007/0003570 A1 | 1/2007 | Murtaugh et al. |
| 2007/0042000 A1 | 2/2007 | Mengeling et al. |
| 2009/0148474 A1 | 6/2009 | Roof et al. |
| 2010/0003278 A1 | 1/2010 | Roof et al. |
| 2010/0028860 A1 | 2/2010 | Roof et al. |
| 2010/0129398 A1 | 5/2010 | Klinge et al. |
| 2011/0104201 A1 | 5/2011 | Mengeling et al. |
| 2011/0117129 A1 | 5/2011 | Roof et al. |
| 2011/0195088 A1 | 8/2011 | Roof et al. |
| 2012/0213810 A1 | 8/2012 | Burgard et al. |
| 2016/0317642 A1 | 11/2016 | Gallei et al. |
| 2017/0065709 A1 | 3/2017 | Burgard et al. |

FOREIGN PATENT DOCUMENTS

| | | |
|---|---|---|
| EP | 208672 A1 | 1/1987 |
| EP | 0440219 A1 | 8/1991 |
| EP | 0529584 A2 | 3/1993 |
| EP | 587780 A1 | 3/1994 |
| EP | 0595436 A2 | 5/1994 |
| EP | 0610250 A1 | 8/1994 |
| EP | 676467 A2 | 10/1995 |
| EP | 732340 A2 | 9/1996 |
| EP | 0835929 A1 | 4/1998 |
| EP | 0835930 A1 | 4/1998 |
| EP | 0839912 A1 | 5/1998 |
| EP | 1018557 A2 | 7/2000 |
| FR | 2602791 A1 | 2/1988 |
| GB | 2282811 A | 4/1995 |
| GB | 2289279 A | 11/1995 |
| JP | 62/198626 A | 9/1987 |
| WO | 198803410 A1 | 5/1988 |
| WO | 198908701 A1 | 9/1989 |
| WO | 199221375 A1 | 12/1992 |
| WO | 199303760 A1 | 3/1993 |
| WO | 199306211 A1 | 4/1993 |
| WO | 199307898 A1 | 4/1993 |
| WO | 199314196 A1 | 7/1993 |
| WO | 199418311 A1 | 8/1994 |
| WO | 199528227 A1 | 10/1995 |
| WO | 199531550 A1 | 11/1995 |
| WO | 1996004010 A1 | 2/1996 |
| WO | 199606619 A1 | 3/1996 |
| WO | 1996036356 A1 | 11/1996 |
| WO | 199640932 A1 | 12/1996 |
| WO | 199700696 A1 | 1/1997 |
| WO | 199731651 A1 | 9/1997 |
| WO | 199731652 A1 | 9/1997 |
| WO | 1998018933 A1 | 5/1998 |
| WO | 199835023 A1 | 8/1998 |
| WO | 199850426 A1 | 11/1998 |
| WO | 199855625 A1 | 12/1998 |
| WO | 199855626 A2 | 12/1998 |
| WO | 2000053787 A1 | 9/2000 |
| WO | 200065032 A1 | 11/2000 |
| WO | 200159077 A1 | 8/2001 |
| WO | 200190363 A1 | 11/2001 |
| WO | 2002095040 A1 | 11/2002 |
| WO | 2003062407 A1 | 7/2003 |
| WO | 2006002193 A2 | 1/2006 |
| WO | 2006034319 A2 | 3/2006 |
| WO | 2006074986 A2 | 7/2006 |
| WO | 2007064742 A2 | 6/2007 |
| WO | 2008109237 A2 | 9/2008 |
| WO | 2008121958 A1 | 10/2008 |
| WO | 2010025109 A1 | 3/2010 |
| WO | 20110128415 A1 | 10/2011 |
| WO | 2015092058 A1 | 6/2015 |

OTHER PUBLICATIONS

Wesley et al., "Differentiation of a porcine reproductive and respiratory syndrome virus vaccine strain from North American field strains by restrction fragment length polymorphism analysis of ORF 5". Journal of Veterinary Diagnostic Investigation, vol. 10, 1998, pp. 140-144.

"Dutch Team Isolates Mystery Pig Disease Agent", Animal Pharm, vol. 230, Abstract No. 00278268, Jun. 21, 1991, p. 21.

"For purification of viral RNA from Plasma, Serum, Cell-free body fluids, Cell-Culture supernatants". QIAamp® Viral RNA Mini Kit Handbook, QIAGEN, Jan. 1999, Cat #52906, pp. 1-35.

"Frontiers closing to mystery disease pigs". Animal Pharm., No. 228, May 24, 1991, p. 2.

"Revision of the taxonomy of the Coronavirus, Torovirus, and Arterivirus genera". Archives of Virology, vol. 135, 1994, pp. 227-239.

Abstracts of Papers Presented at the 71st Annual Meeting of the Conference of Research Workers in Animal Disease, Nos. 1-6, Nov. 5-6, 1990, 2 pages.

(56) References Cited

OTHER PUBLICATIONS

Aksenova et al., "Cultivation of the rabies virus in the continuous kidney cell line 4647 from the green marmoset". Vopr. Virusol., vol. 30, No. 2, 1985, pp. 180-182. (See AXENOVA for English Abstract).

Albina et al., "Immune responses in pigs infected with porcine reproductive and respiratory syndrome virus (PRRSV)". Veterinary Immunology and Immunopathology, vol. 61, 1998, pp. 49-66.

Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.

Allende et al., "Mutations in the genome of porcine reproductive and respiratory syndrome virus responsible for the attenuated phenotype". Archives of Virology, vol. 145, No. 6, Jun. 2000, pp. 1149-1161.

Allende et al., "North American and European porcine reproductive and respiratory syndrome viruses differ in nonstructural protein coding regions". Journal of General Virology, vol. 80, 1999, pp. 307-315.

Altschul et al., "Basic Local Alignment Search Tool". Journal of Molecular Biology, vol. 215, 1990, pp. 403-410.

Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.

Ashworth et al., "Antibody-dependent cell-mediated cytotoxicity (ADCC) in Aujeszky's disease". Archives of Virology, vol. 59, No. 4, 1979, pp. 307-318.

Axenova, T.A. "Propagation of Rabies Vaccine Virus in Continuous Green Monkey Kidney Cells 4647". Vopr. Virusol., vol. 30, No. 2, 1985, p. 182. (English Abstract of Aksenova Reference.).

Backstrom et al., "Respiratory Diseases of Swine". Veterinary Clinics of North America: Large Animal Practice, vol. 4, No. 2, Nov. 1982, pp. 259-276.

Barfoed et al., "DNA vaccination of pigs with open reading frame 1-7 of PRRS virus". Vaccine, vol. 22, 2004, pp. 3628-3641.

Baric et al., "Interactions between Coronavirus Nucleocapsid Protein and Viral RNAs: Implications for Viral Transcription". Journal of Virology, vol. 62, No. 11, Nov. 1988, pp. 4280-4287.

Baric et al., "Subgenomic Negative-Strand RNA Function during Mouse Hepatitis Virus Infection". Journal of Virology, vol. 74, No. 9, May 2000, pp. 4039-4046.

Bautista et al., "Comparison of Porcine Alveolar Macrophages and CL 2621 for the Detection of Porcine Reproductive and Respiratory Syndrome (PRRS) Virus and Anti-PRRS Antibody". Journal of Veterinary Diagnostic Investigation, vol. 5, No. 2, Apr. 1993, pp. 163-165.

Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.

Beale, AJ, "Vaccines and antiviral drugs". Principles of bacteriology, virology and immunity, vol. 3, Ch. 86, 1984, pp. 147-161.

Beare et al., "Further Studies in Man of Man of HSw1N1 Influenza Viruses". Journal of Medical Virology, vol. 5, 1980, pp. 33-38.

Beghi et al., "Guillain-Barré Syndrome: Clinicoepidemiologic Features and Effect of Influenza Vaccine". Archives of Neurology, vol. 42, No. 11, 1985, pp. 1053-1057.

Benfield et al., "Characterization of swine infertility and respiratory syndrome (SIRS) virus (isolate ATCC VR-2332)". Journal of Veterinary Diagnostic Investigation, vol. 4, 1992, pp. 127-133.

Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.

Benfield et al., "Properties of SIRS Virus Isolate ATCC VR-2332 in the United States and Preliminary Characterization of a Monoclonal Antibody to this Virus". American Association of Swine Practitioners Newsletter, vol. 4, No. 4, Jul./Aug. 1992, pp. 19-21.

Berendt et al., "Evaluation of Commercially Prepared Vaccines for Experimentally Induced Type/A/New Jersey/8/76 Influenza Virus Infections in Mice and Squirrel Monkeys". The Journal of Infectious Diseases, vol. 136, Dec. 1977, pp. S712-S718.

Berendt et al., "Reaction of Squirrel Monkeys to Intratracheal Inoculation with Influenza/A/New Jersey/76 (Swine) Virus". Infection and Immunity, vol. 16, No. 2, May 1977, pp. 476-479.

Bilodeau et al., "'Porcine Reproductive and Respiratory Syndrome' in Quebec". The Veterinary Record, Aug. 3, 1991, p. 102.

Blackburn et al., "Use of human influenza vaccine to protect against blue-eared pig disease". Veterinary Record, vol. 129, No. 1, Jul. 1991, p. 19.

Bohl et al., "Isolation and Serotyping of Porcine Rotaviruses and Antigenic Comparison with Other Rotaviruses". Journal of Clinical Microbiology, vol. 19, No. 2, Feb. 1984, pp. 105-111.

Bouillant et al., "Viral Susceptibility of a Cell Line Derived from the Pig Oviduct". Canadian Journal of Comparative Medicine, vol. 39, 1975, pp. 450-456.

Boursnell et al., "Sequence of the membrane protein gene from avian coronavirus IBV". Virus Research, vol. 1, 1984, pp. 303-313.

Boursnell et all., "Completion of the Sequence of the Genome of the Coronavirus Avian Infectious Bronchitis Virus". Journal of General Virology, vol. 68, 1987, pp. 57-77.

Bowie et al., "Deciphering the Message of Protein Sequences: Tolerance to Amino Acid Substitutions". Science, vol. 247, 1990, pp. 1306-1310.

Boyer et al., "Infectious Transcripts and cDNA Clones of RNA Viruses". Virology, vol. 198, No. 2, Feb. 1994, pp. 415-426.

Bramel-Verheije et al., "Expression of a Foreign Epitope by Porcine Reproductive and Respiratory Syndrome Virus". Virology, vol. 278, 2000, pp. 380-389.

Bredenbeek et al., "The primary structure and expression of the second open reading frame of the polymerase gene of the coronavirus MHV-A59; a highly conserved polymerase is expressed by an efficient ribosomal frameshifting mechanism". Nucleic Acids Research, vol. 18, No. 7, 1990, pp. 1825-1832.

Brenner et al., "A Negative Staining Method for High Resolution Electron Microscopy of Viruses". Biochimica Et Biophysica Acta, vol. 34, 1959, pp. 103-110.

Brinton-Darnell et al., "Structure and chemical-physical characteristics of lactate dehydrogenase-elevating virus and its RNA". Journal of Virology, vol. 16, No. 2, Aug. 1975, pp. 420-433.

Brinton-Darnell, M. "Lactate Dehydrogenase-Elevating, Equine Arteritis and Lelystad Viruses". Encyclopedia of Virology, vol. 2, 1999, pp. 763-771.

Bruner, D.W., "Table XXXII. Characteristics of Viral Respiratory Infections in Swine" Hagan's Infectious Diseases of Domestic Animals: With Special Reference to Etiology, Diagnosis, and Biologic Therapy, Sixth Edition, Comstock Publishing Associations, a division of Cornell University Press, Ithaca and London, 1973, 5 pages.

Brüggemann et al., "Immunoglobulin V region variants in hybridoma cells. I. Isolation of a variant with altered idiotypic and antigen binding specificity". The EMBO Journal, vol. 1, No. 5, 1982, pp. 629-634.

Buck, K. W., "Comparison of the Replication of Positive-Stranded RNA Viruses of Plants and Animals". Advances in Virus Research, vol. 47, 1996, pp. 159-251.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue". The Journal of Cell Biology, vol. 111, 1990, pp. 2129-2138.

Burroughs, et al., "Relationship of San Miguel Sea Lion Virus to Other Members of the Calicivirus Group". Intervirology, vol. 10, 1978, pp. 51-59.

Cabasso et al., "Propagation of Infectious Canine Hepatitis Virus in Tissue Culture". Proceedings of the Society for Experimental Biology and Medicine, vol. 85, 1954, pp. 239-245.

Caeiro et al., "In vitro DNA replication by cytoplasmic extracts from cells infected with African swine fever virus". Virology, vol. 179, No. 1, Nov. 1990, pp. 87-94.

(56) References Cited

OTHER PUBLICATIONS

Callebaut et al., "Antigenic Differentiation between Transmissible Gastroenteritis Virus of Swine and a Related Porcine Respiratory Coronavirus". Journal of General Virology, vol. 69, 1988, pp. 1725-1730.
Carrascosa et al., "Relationship of San Miguel Sea Lion Virus to Other Members of the Calicivirus Group". Journal of Virological Methods, vol. 3, No. 6, Jan. 1982, pp. 303-310.
Theil et al., "Partial characterization of a bovine group A rotavirus with a short genome electropherotype". Journal of Clinical Microbiology, vol. 26, No. 6, Jun. 1988, p. 1094-1099.
Thomson et al., "Ontario. Proliferative and necrotizing pneumonia (PNP) of swine: the Ontario situation". Canadian Veterinary Journal, vol. 32, May 1991, p. 313.
Thouless et al., "Isolation of two lapine rotaviruses: Characterization of their subgroup, serotype and RNA electropherotypes". Archives of Virology, vol. 89, Nos. 1-4, 1986, pp. 161-170.
Tian et al., "Emergence of Fatal PRRSV Variants: Unparalleled Outbreaks of Atypical PRRS in China and Molecular Dissection of the Unique Hallmark". PLoS One, vol. 2, No. 6, e526, 2007, pp. 1-10.
Timony, P.J. "Equine Viral Arteritis", Manual of Standards for Diagnostic Tests and Vaccines, 1992, pp. 493-500.
Tobita et al., "Plaque Assay and Primary Isolation of influenza A Viruses in an Established Line of Canine Kidney Cells (MDCK) in the Presence of Trypsin". Medical Microbiology and Immunology, vol. 162, No. 1, Dec. 1975, pp. 9-14.
Todd et al., "Development of an adjuvant-active nonionic block copolymer for use in oil-free subunit vaccines formulations". Vaccine, vol. 15, No. 5, 1997, pp. 564-570.
Travassos et al., "Carajas and Maraba Viruses, Two New Vesiculoviruses Isolated from Phlebotomine Sand Flies in Brazil". American Journal of Tropical Medicine and Hygiene, vol. 33, No. 5, Sep. 1984, pp. 999-1006.
Tsunemitsu et al., "Isolation, characterization, and serial propagation of a bovine group C rotavirus in a monkey kidney cell line (MA104)". Journal of Clinical Microbiology, vol. 29, No. 11, Nov. 1991, pp. 2609-2613.
Ulmer et al., "Enhancement of DNA vaccine potency using conventional aluminum adjuvants". Vaccine, vol. 18, 2000, pp. 18-28.
Urasawa et al., "Sequential Passages of Human Rotavirus in MA-104 Cells". Microbiology and Immunology, vol. 25, No. 10, 1981, pp. 1025-1035.
Van Alstine, W.G., "Mystery Swine Disease in the United States". The New Pig Disease: Porcine Respiration and Reproductive Syndrome. A Report on the Seminar/Workshop Held in Brussels by the European Commission (Directorate-General for Agriculture), Apr. 29-30, 1991, pp. 65-70.
Van Alstine, W.G., "Past Diagnostic Approaches and Findings and Potentially Useful Diagnostic Strategies". Proceedings Mystery Swine Disease Committee Meeting, Oct. 6, 1990, pp. 52-58.
Van Berlo et al., "Equine Arteritis Virus-Infected Cells Contain Six Polyadenylated Virus-Specific RNAs". Virology, vol. 118, 1982, pp. 345-352.
Van Der Linden et al., "Virological kinetics and immunological responses to a porcine reproductive and respiratory syndrome virus infection of pigs at different ages". Vaccine, vol. 21, 2003, pp. 1952-1957.
Van Der Meer et al., "ORF1a-Encoded Replicase Subunits are Involved in the Membrane Association of the Arterivirus Replication Complex". Journal of Virology, vol. 72, No. 8, 1998, pp. 6689-6698.
Van Der Most et al., "A Domain at the 3' End of the Polymerase Gene is Essential for Encapsidation of Coronavirus Defective Interfering RNAs". Journal of Virology, vol. 65, No. 6, Jun. 1991, pp. 3219-3226.
Van Dinten et al., "An infectious arterivirus cDNA clone: Identification of a replicase point mutation that abolished discontinuous mRNA transcription". Proceedings of the National Academy of Sciences, vol. 94, Feb. 1997, pp. 997-996.

Van Dinten et al., "Processing of the Equine Arteritis Virus Replicase ORF1b Protein: Identification of Cleavage Products Containing the Putative Viral Polymerase and Helicase Domains". Journal of Virology, vol. 70, No. 10, Oct. 1996, pp. 6625-6633.
Van Dinten et al., "Proteolytic Processing of the Open Reading Frame 1b-Encoded Part of Arterivirus Replicase is Mediated by nsp4 Serine Protease and Is Essential for Virus Replication". Journal of Virology, vol. 73, No. 3, Mar. 1999, pp. 2027-2037.
Van Marle et al., "Arterivirus discontinuous mRNA transcription is guided by base pairing between sense and antisense transcription-regulating sequences". Proceedings of the National Academy of Sciences, vol. 96, 1999, pp. 12056-12061.
Van Marle et al., "Characterization of an Equine Arteritis Virus Replicase Mutant Defective in Subgenomic mRNA Synthesis". Journal of Virology, vol. 73, No. 7, Jul. 1999, pp. 5274-5281.
Van Marle et al., "Regulation of Coronavirus mRNA Transcription". Journal of Virology, vol. 69, No. 12, Dec. 1995, pp. 7851-7856.
Van Nieuwstadt et al., "Infection with porcine respiratory coronavirus does not fully protect pigs against intestinal transmissable gastroenteritis virus". The Veterinary Record, vol. 125, No. 3, 1989, pp. 58-60.
Van Nieuwstadt et al., "Proteins Encoded by Open Reading Frames 3 and 4 of the Genome of Lelystad Virus (*Arteriviridae*) are Structural Proteins of the Virion". Journal of Virology, vol. 70, No. 7, Jul. 1996, pp. 4767-4772.
Van Nieuwstadt et al., "Use of two enzyme-linked immunosorbent assays to monitor antibody responses in swine with experimentally induced infection with porcine epidemic diarrhea virus". American Journal of Veterinary Research, vol. 42, Jul. 1991, pp. 1044-1050.
Van Zijl et al., "Live Attenuated Pseudorabies Virus Expressing Envelope Glycoprotein E1 of Hog Cholera Virus Protects Swine Against Both Pseudorabies and Hog Cholera". Journal of Virology, vol. 65, No. 5, May 1991, pp. 2761-2765.
Vennema et al., "Nucleocapsid-independent assembly of coronavirus-like particles by co-expression of viral envelope protein genes". The EMBO Journal, vol. 15, No. 8, 1996, pp. 2020-2028.
Verheije et al., "Kissing Interaction between 3' Noncoding and Coding Sequences is Essential for Porcine Arterivirus RNA Replication". Journal of Virology, vol. 76, No. 3, Feb. 2002, pp. 1521-1526.
Verheije et al., "Safety and protective efficacy of porcine reproductive and respiratory syndrome recombinant virus vaccines in young pigs". Vaccine, vol. 21, 2003, pp. 2556-2563.
Veterinary Bulletin, vol. 58, No. 11, 1988, Nos. 6903-6909, p. 932.
Veterinary Bulletin, vol. 60, No. 3, 1990, Nos. 1536-1551, pp. 255-256.
Vieira et al., "New pUC-derived cloning vectors with different selectable markers and DNA replication origins". Gene, vol. 100, 1991, pp. 189-194.
VIIIth International Symposium on Nidoviruses (Corona and Arteriviruses), May 20-25, 2000, 32 pages.
Visser, Nicolaas, "Declaration of Dr. N. Visser". Nov. 14, 1995, pp. 1-11.
Von Busse, F.W., Epidemiologic Studies on Porcine Reproductive and Respiratory Syndrome (PRRS). Tierarztliche Umschau, Dec. 1991, pp. 708-717 (Abstract in English p. 711).
Von Ohlinger et al., "Der Seuchenhafte Spatabort beim Schwein Ein Beitrag zur Atiologie des Porcine Reproductive and Respiratory Syndrome (PRRS)". Tierarztl, vol. 46, 1991, pp. 703-708.
Waltner-Toews et al., "A Field Trial to Evaluate the Efficacy of a Combined Rotavirus-Coronavirus/ *Escherichia coli* vaccine in Dairy Cattle"., Canadian Journal of Comparative Medicine, vol. 49, No. 1, 1985, pp. 1-9.
Wang et al., "Attenuation of porcine reproductive and respiratory syndrome virus strain MN184 using chimeric construction with vaccine sequence". Virology, vol. 371, 2008, pp. 418-429.
Ward et al., "Efficiency of human rotavirus propagation in cell culture". Journal of Clinical Microbiology, vol. 19, No. 6, Jun. 1984, pp. 748-753.
Wardley et al., "The Host Response to African Swine Fever Virus". Progress of Medical Virology, vol. 34, 1987, pp. 180-192.
Wassenaar et al., "Alternative Proteolytic Processing of the Arterivirus Replicase ORF1a Polyprotein: Evidence that NSP2 Acts

(56) References Cited

OTHER PUBLICATIONS as a Cofactor for the NSP4 Serine Protease". Journal of Virology, vol. 71, No. 12, Dec. 1997, pp. 9313-9322.

Webster et al., "Chemotherapy and Vaccination: a Possible Strategy for the Control of Highly Virulent Influenza Virus". Journal of Virology, vol. 55, No. 1, 1985, pp. 173-176.

Welch et al., "Construction and evaluation of genetically engineered replication-defective porcine reproductive and respiratory syndrome virus vaccine candidates". Veterinary Immunology and Immunopathology, vol. 102, 2004, pp. 277-290.

Wensvoort et al., "'Blue ear' disease in pigs". Veterinary Record, vol. 128, No. 24, Jun. 1991, p. 574.

Wensvoort et al., "'Lelystad agent'—the cause of abortus blauw (mystery swine disease)". Tijdschr Diergeneeskd, vol. 116, No. 13, Jul. 1991, pp. 675-676.

Wensvoort et al., "An Enzyme Immunoassay Employing Monoclonal Antibodies and Detecting Specifically Antibodies to Classical Swine Fever Virus". Veterinary Microbiology, vol. 17, 1988, pp. 129-140.

Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.

Wensvoort et al., "Bovine viral diarrhoea virus infections in piglets born to sows vaccinated against swine fever with contaminated vaccine". Research in Veterinary Science, vol. 45, 1988, pp. 143-148.

Wensvoort et al., "Characterization of Porcine and Some Ruminant Pestiviruses by Cross-neutralization" vol. 20, 1989, pp. 291-306.

Haynes et al., "Temporal and Morphologic Characterization of the Distribution of Porcine Reproductive and Respiratory Syndrome Virus (PRRSV) by In Situ Hybridization in Pigs Infected with Isolates of PRRSV that Differ in Virulence". Veterinary Pathology, vol. 34, 1997, pp. 39-43.

Heath, et al., "The Behaviour of Some Influenza Viruses in Tissue Cultures of Kidney Cells of Various Species". Archiv. f. Virusforschung Bd. VIII, HS, 1958, pp. 577-591.

Hedger et al., "Swine Vesicular Disease Virus". Virus Infections of Porcines, Elsevier Science Publishers, B.V., 1989, pp. 241-250.

Hennen, J., "Statistical methods for longitudinal research on bipolar disorders". Bipolar Disorders, vol. 5, 2003, pp. 156-168.

Hill, Howard, "Overview and History of Mystery Swine". Proceedings of the Mystery Swine Disease Committee Meeting, Denver, CO, Oct. 6, 1990, pp. 29-40.

Hirsch et al., "Ultrastructure of Human Leukocytes After Simultaneous Fixation with Glutaraldehyde and Osmium Tetroxide and "Postfixation" in Uranyl Acetate". The Journal of Cell Biology, vol. 38, 1968, pp. 615-627.

Hofmann et al., "Propagation of the virus of porcine epidemic diarrhea in cell culture". Journal of Clinical Microbiology, vol. 26, No. 11, Nov. 1988, pp. 2235-2239.

Hofmann et al., "Quantitation, biological and physicochemical properties of cell culture-adapted porcine epidemic diarrhea coronavirus (PEDV)". Veterinary Microbiology, vol. 20, No. 2, Jun. 1989, pp. 131-142.

Honda et al., "A Serological Comparison of 4 Japanese Isolates of Porcine Enteroviruses with the International Reference Strains". The Japanese Journal of Veterinary Science, vol. 52, No. 1, 1990, pp. 49-54.

Horowitz et al., "Anti-schistosome monoclonal antibodies of different isotypes—correlation with cytotoxicity". The EMBO Journal, vol. 2, No. 2, 1983, pp. 193-198.

Horsfall et al., "General Principles of Animal Virus Multiplication". Viral and Rickettsial Infections of Man, Fourth Edition, J.B. Lippincott Company, Philadelphia, 1965, pp. 239-241.

Horzinek et al., "Studies on the Substructure of Togaviruses: II. Analysis of Equine Arteritis Rubella, Bovine Viral Diarrhea, and Hog Cholera Viruses". Archiv Für die gesamte Virusforschung, vol. 33, 1971, pp. 306-318.

Hoshino et al., "Isolation and characterization of an equine rotavirus". Journal of Clinical Microbiology, vol. 18, No. 3, Sep. 1983, pp. 585-591.

Hoshino et al., "Serotypic Similarity and Diversity of Rotaviruses of Mammalian and Avian Origin as Studied by Plaque-Reduction Neutralization". The Journal of Infectious Diseases, vol. 149, No. 5, May 1984, pp. 694-702.

Hsue et al., "Characterization of an Essential RNA Secondary Structure in the 3' Untranslated Region of the Murine Coronavirus Genome". Journal of Virology, vol. 74, No. 15, Aug. 2000, pp. 6911-6921.

Huang et al., "Polypyrimidine Tract-Binding Protein Binds to the Complementary Strand of the Mouse Hepatitis Virus 39 Untranslated Region, Thereby Altering RNA Conformation". Journal of Virology, vol. 73, No. 11, Nov. 1999, pp. 9110-9116.

Hurrelbrink et al., "Attenuation of Murray Valley Encephalitis Virus by Site-Directed Mutagenesis of the Hinge and Putative Receptor-Binding Regions of the Envelope Protein". Journal of Virology, vol. 75, No. 16, Aug. 2001, pp. 7692-7702.

Hwang et al., "A 68-Nucleotide Sequence within the 39 Noncoding Region of Simian Hemorrhagic Fever Virus Negative-Strand RNA Binds to Four MA104 Cell Proteins". Journal of Virology, vol. 72, No. 5, May 1998, pp. 4341-4351.

Hyllseth, B., "Structural Proteins of Equine Arteritis Virus". Archiv Für die gesamte Virusforschung, vol. 30, 1973, pp. 177-188.

Iltis et al., "Persistent Varicella-Zoster virus infection in a human rhabdomyosarcoma cell line and recovery of a plaque variant". Infection and Immunity, vol. 37, No. 1, Jul. 1982, pp. 350-358.

Imagawa et al., "Isolation of Foal Rotavirus in MA-104 Cells". Bulleting of Equine Research Institute, vol. 18, 1981, pp. 119-128.

Izeta et al., "Replication and Packaging of Transmissible Gastroenteritis Coronavirus-Derived Synthetic Minigenomes". Journal of Virology, vol. 73, No. 2, Feb. 1999, pp. 1535-1545.

Jackwood et al., "Replication of Infectious Bursal Disease Virus in Continuous Cell Lines". Avian Diseases, vol. 31, No. 2, Apr.-Jun. 1987, pp. 370-375.

Johnson et al., "Feline panleucopaenia virus. IV. Methods for obtaining reproducible in vitro results". Research in Veterinary Science, vol. 8, No. 2, Apr. 1967, pp. 256-264.

Johnson et al., "Pathogenic and humoral immune responses to porcine reproductive and respiratory syndrome virus (PRRSV) are related to viral load in acute infection". Veterinary Immunology and Immunopathology, vol. 102, No. 3, PRRS Immunology and Immunopathology Special Issue, Dec. 2004, pp. 233-247.

Johnston et al., "Genetic to genomic vaccination". Vaccine, vol. 15, No. 8, 1997, pp. 808-809.

Joo et al., "Encephalomyocarditis Virus as a Potential Cause for Mystery Swine Disease", Livestock Conservation Institute, Proceedings of the Mystery Swine Disease Committee Meeting, Denver, CO, Oct. 6, 1990, pp. 62-66.

Jun et al., "Comparison of Dynamics in Viremia Levels in Chickens Inoculated with Marek's Disease Virus Strains of Different Pathotypes". Virologica Sinica, vol. 16, No. 1, Mar. 2001, pp. 59-63.

Jusa et al., "Effect of heparin on infection of cells by porcine reproductive and respiratory syndrome virus". American Journal of Veterinary Research, vol. 58, No. 5, May 1997, pp. 488-491.

Just et al., "A/New Jersey/76 influenza vaccine trial in seronegative schoolchildren: Comparison of a subunit vaccine with a whole-virus vaccine". Medical Microbiology and Immunology, vol. 164, No. 4, 1978, pp. 277-284.

Kang et al., "Primary Isolation and Identification of Avian Rotaviruses from Turkeys Exhibiting Signs of Clinical Enteritis in a Continuous MA-104 Cell Line". Avian Diseases, vol. 30, 1986, pp. 494-499.

Kapur et al., "Genetic variation in porcine reproductive and respiratory syndrome virus isolates in the midwestern United States". Journal of General Virology, vol. 77, 1996, pp. 1271-1276.

Kasza et al., "Establishment, viral susceptibility and biological characteristics of a swine kidney cell line SK-6". Research in Veterinary Science, vol. 13, No. 1, Jan 1972, pp. 46-51.

Kasza et al., "Isolation and Characterization of a Rotavirus from Pits". Veterinary Record, vol. 87, 1970, pp. 681-686.

(56) References Cited

OTHER PUBLICATIONS

Katz et al., "Antigenic differences between European and American isolates of porcine reproductive and respiratory syndrome virus (PRRSV) are encoded by the carboxyterminal portion of viral open reading frame 3". Veterinary Microbiology, vol. 44, No. 1, Apr. 1995, pp. 65-76.

Keffaber, K., "Reproductive Failure of Unknown Etiology"., AASP Newsletter, vol. 1, No. 2, Sep.-Oct. 1989, pp. 1, 4-5, 8-10.

Keffaber, K.K., "Swine Reproductive Failure of Unknown Etiology". The George A. Young Swine Conference & Annual Nebraska SPF Swine Conference, Aug. 13-14, 1990, pp. 55-67.

Key et al., "Genetic variation and phylogenetic analyses of the ORF5 gene of acute porcine reproductive and respiratory syndrome virus isolates". Veterinary Microbiology, vol. 83, 2001, pp. 249-263.

Kim et al., "Analysis of cis-Acting Sequences Essential for Coronavirus Defective Interfering RNA Replication". Virology, vol. 197, No. 1, Nov. 1993, pp. 53-63.

Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.

Kim et al., "Enhanced replication of porcine reproductive and respiratory syndrome (PRRS) virus in a homogeneous subpopulation of MA-104 cell line". Archives of Virology, vol. 133, 1993, pp. 477-483.

Klein et al., "Deletion of the IgH enhancer does not reduce immunoglobulin heavy chain production of a hybridoma IgD class switch variant". The EMBO Journal, vol. 3, No. 11, Nov. 1984, pp. 2473-2476.

Klinge et al, "Age-dependent resistance to Porcine reproductive and respiratory syndrome virus replication in swine". Virology Journal, vol. 6, No. 177, Oct. 2009.

Klinge et al., "PRRSV replication and subsequent immune responses in swine of various ages". Abstract of Poster No. 56, International Porcine Reproductive and Respiratory Syndrome (PRRS) Symposium, PRRS and PRRSV-Related Diseases: Prevention and Control Strategies, Chicago, IL, Nov. 30-Dec. 1, 2007.

Klovins et al., "A Long-range Pseudoknot in Qb RNA is Essential for Replication". Journal of Molecular Biology, vol. 294, 1999, pp. 875-884.

Klump et al., "Complete Nucleotide Sequence of Infectious Coxsackievirus B3 cDNA: Two Initial 5' Uridine Residues are Regained during Plus-Strand RNA Synthesis". Journal of Virology, vol. 64, No. 4, Apr. 1990, pp. 1573-1583.

Klupp et al., "Sequence and expression of the glycoprotein gH gene of pseudorabies virus". Virology, vol. 182, No. 2, Jun. 1991, pp. 732-741.

Knowles et al., "Classification of porcine enteroviruses by antigenic analysis and cytopathic effects in tissue culture: Description of 3 new serotypes". Archives of Virology, vol. 62, No. 3, 1979, pp. 201-208.

Kolodziej et al., "Epitope tagging and protein surveillance". Methods in Enzymology, vol. 194, 1991, pp. 508-519.

Kouvelos et al., "Comparison of Bovine, Simian and Human Rotavirus Structural Glycoproteins". Journal of General Virology, vol. 65, Jul. 1984, pp. 1211-1214.

Mengeling et al., "Comparative safety and efficacy of attenuated single-strain and multi-strain vaccines for porcine reproductive and respiratory syndrome". Veterinary Microbiology, vol. 93, 2003, pp. 25-38.

Mengeling et al., "Comparison among strains of porcine reproductive and respiratory syndrome virus for their ability to cause reproductive failure". American Journal of Veterinary Research, vol. 57, No. 6, Jun. 1996, pp. 834-839.

Mengeling et al., "Mystery Pig Disease: Evidence and Considerations for its Etiology". Proceedings of the Mystery Swine Disease Committee Meeting, Oct. 6, 1990, Denver, Colorado, Livestock Conservation Institute, Madison, WI, USA, pp. 88-90.

Mengeling et al., "Strain specificity of the immune response of pigs following vaccination with various strains of porcine reproductive and respiratory syndrome virus". Veterinary Microbiology, vol. 93, 2003, pp. 13-24.

Meredith, MJ, "Porcine Reproductive and Respiratory Syndrome (PRRS)", Pig Disease Information Center, 1st North American Edition, University of Cambridge, Aug. 1994, pp. 1-57.

Mettenleiter et al., "Isolation of a viable herpesvirus (pseudorabies virus) mutant specifically lacking all four known nonessential glycoproteins". Virology, vol. 179, No. 1, Nov. 1990, pp. 498-503.

Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.

Meulenberg et al., "Characterization of Proteins Encoded by ORFs 2 to 7 of Lelystad Virus". Virology, vol. 206, No. 1, Jan. 1995, pp. 155-163.

Meulenberg et al., "Identification and Characterization of a Sixth Structural Protein of Lelystad Virus: The Glycoprotein GP2Encoded by ORF2 is Incorporated in Virus Particles". Virology, vol. 225, No. 1, Nov. 1996, pp. 44-51.

Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.

Meulenberg et al., "Lelystad Virus, the Causative Agent of Porcine Epidemic Abortion and Respiratory Syndrome (PEARS), is Related to LDV and EAV". Virology, vol. 192, 1993, pp. 62-72.

Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.

Meulenberg et al., "Molecular characterization of Lelystad virus". Veterinary Microbiology, vol. 55, 1997, pp. 197-202.

Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.

Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.

Meulenberg et al., "Subgenomic RNAs of Lelystad virus contain a conserved leader-body junction sequence". Journal of General Virology, vol. 74, 1993, pp. 1697-1701.

Molenkamp et al., "Isolation and Characterization of an Arterivirus Defective Interfering RNA Genome". Journal of Virology, vol. 74, No. 7, 2000, pp. 3156-3165.

Molenkamp et al., "The arterivirus replicase is the only viral protein required for genome replication and subgenomic mRNA transcription". Journal of General Virology, vol. 81, No. 10, 2000, pp. 2491-2496.

Montagnon, B.J., "Polio and rabies vaccines produced in continuous cell lines: a reality for Vero cell line". Dev Biol Stand., vol. 70, 1989, pp. 27-47.

Moore, C., "Porcine Proliferative and Necrotyzing Pneumonia Clinical Findings". Presented at American Association of Swine Practitioners, 22nd Annual Meeting, Mar. 3-5, 1991, pp. 443-453.

Moormann et al., "Hog cholera virus: identification and characterization of the viral RNA and the virus specific RNA synthesized in infected swine kidney cells". Virus Research, vol. 11, 1988, pp. 281-291.

Moormann et al., "Infectious RNA Transcribed from an Engineered Full-Length cDNA Template of the Genome of a Pestivirus". Journal of Virology, vol. 70, No. 2, Feb. 1996, pp. 763-770.

Moormann et al., "Molecular cloning and nucleotide sequence of hog cholera virus strain brescia and mapping of the genomic region encoding envelope protein E1". Virology, vol. 177, No. 1, Jul. 1990, pp. 184-198.

Morin et al., "Severe proliferative and necrotizing pneumonia in pigs: A newly recognized disease". Canadian Veterinary Journal, vol. 31, Dec. 1990, pp. 837-839.

(56) References Cited

OTHER PUBLICATIONS

Morozov et al., "Sequence analysis of open reading frames (ORFs) 2 to 4 of a U.S. isolate of porcine reproductive and respiratory syndrome virus". Archives of Virology, vol. 140, No. 7, 1995, pp. 1313-1319.
Morrison et al., "Brief Communications Serologic evidence incriminating a recently isolated virus (ATCC VR-2332) as the cause of swine infertility and respiratory syndrome (SIRS)". Journal of Veterinary Diagnostic Investigation, vol. 4, No. 2, Apr. 1992, pp. 186-188.
Morrison et al., "Sero-epidemiologic Investigation of Swine Infertility and Respiratory Syndrome (SIRS)". 72st Annual Meeting of the Conference of Research Workers in Animal Disease, Chicago, IL, Nov. 11-12, 1991, p. 55, Abstract No. 309.
Mountz et al., "The in vivo generation of murine IgD-secreting cells is accompanied by deletion of the Cμ gene and occasional deletion of the gene for the Cd1 domain". The Journal of Immunology, vol. 145, No. 5, Sep. 1990, pp. 1583-1591.
Mukamoto et al., "Immunogenicity in Aujeszky's disease virus structural glycoprotein gVI (gp50) in swine". Veterinary Microbiology, vol. 29, No. 2, Oct. 1991, pp. 109-121.
Murakami, et al., "Difference in growth behavior of human, swine, equine, and avian influenza viruses at a high temperature". Archives of Virology, vol. 100, Nos. 3-4, 1988, pp. 231-244.
Murphy et al., "Immunization Against Virus" in Virology, 2nd Edition, vol. 1, Fields, et al., eds. Raven Press, NY, 1990, pp. 469-502.
Murphy et al., "Virus Taxonomy". Chapter 2 in Fields Virology, 2nd. Edition, Fields, et al., eds, Raven Press, New York, 1990, pp. 9-35.
Murtaugh et al., "Comparison of the structural protein coding sequences of the VR-2332 and Lelystad virus strains of the PRRS virus". Archives of Virology, vol. 140, No. 8, 1995, pp. 1451-1460.
Murtaugh et al., "Genetic Variation in the PRRS Virus". Coronaviruses and Arteriviruses, Plenum Press, New York, 1998, pp. 787-794.
Murtaugh et al., "Immunological Responses of Swine to Porcine Reproductive and Respiratory Syndrome Virus Infection". Viral Immunology, vol. 15, No. 4, 2002, pp. 533-547.
Murtaugh et al., "Role of Viral Proteases in PRRS Immunity, Project Period Sep. 1, 1997-Dec. 31, 2002, no cost extension Jan. 1, 2003-Jun. 30, 2003". Final Report: Aug. 30, 2003, Department of Veterinary Pathology, University of Minnesota, St. Paul, MN and Boehringer Ingelheim Vetmedica, Inc., Ames, IA, 2003, pp. 1-38.
Murtaugh, "Allen D Lehman Swine Conference: the Evolution of the Swine veterinary profession: The PRRS Virus". University of Minnesota, Veterinary Continuing Education and Extension, vol. 20, 1993, pp. 43-47.
Myers et al., "Propagation of avian rotavirus in primary chick kidney cell and MA104 cell cultures". Avian Diseases, vol. 33, No. 3, Jul.-Sep. 1989, pp. 578-581.
Nakamura et al., "Studies on Swine Influenza III. Propagation of Swine Influenza Virus in Explants of Respiratory Tract Tissues from Fetal Pigs". The Cornell Veterinarian, vol. LX, No. 1, Jan. 1970, pp. 27-35.
Narayanan et al., "Characterization of the Coronavirus M Protein and Nucleocapsid Interaction in Infected Cells". Journal of Virology, vol. 74, No. 17, Sep. 2000, pp. 8127-8134.
NCBI: Accession No. AE005172. "*Arabidopsis thaliana* chromosome 1, top arm complete sequence." Dec. 14, 2000.
NCBI: Accession No. AF046869. "Porcine reproductive and respiratory syndrome virus isolate 16244B, Feb. 18, 1997 (Nebraska) pass.3, complete genome." Mar. 17, 1999.
NCBI: Accession No. AF066183. "Porcine reproductive and respiratory syndrome virus RespPRRS MLV, complete genome." Feb. 22, 2001.
NCBI: Accession No. AF159149. "Porcine reproductive and respiratory syndrome virus isolate MLV RespPRRS/Repro, complete genome." Aug. 28, 2000.
NCBI: Accession No. AF176348. "Porcine reproductive and respiratory syndrome virus isolate PA8 complete genome." Sep. 3, 2002.
NCBI: Accession No. AF184212. "Porcine reproductive and respiratory syndrome virus strain SP, complete genome." Sep. 28, 2000.
NCBI: Accession No. AF325691. "Porcine reproductive and respiratory syndrome virus isolate NVSL 977985 IA 1-4-2, complete genome." Feb. 11, 2001.
NCBI: Accession No. AF331831. "Porcine reproductive and respiratory syndrome virus BJ-4, complete genome." Jan. 15, 2001.
NCBI: Accession No. M96262. "Lelystad virus, complete genome." Nov. 8, 2000.
NCBI: Accession No. M96262.2. "Lelystad virus, complete genome." Nov. 8, 2000.
NCBI: Accession No. NC_001639. Lactate dehydrogenase-elevating virus, complete genome. Dec. 8, 2008.
NCBI: Accession No. NC_001961. "Porcine reproductive and respiratory syndrome virus, complete genome." Jan. 12, 2004.
NCBI: Accession No. NC_002533. "Lelystad virus, complete genome." Nov. 11, 2000.
NCBI: Accession No. NC_002534. "Lactate dehydrogenase-elevating virus, complete genome." Dec. 29, 2003.
NCBI: Accession No. U15146. "Lactate dehydrogenase-elevating virus Plagemann strain, complete genome." Jan. 26, 1996.
NCBI: Accession No. U87392 AF030244 U00153. "Porcine reproductive and respiratory syndrome virus strain VR-2332, complete genome." Nov. 17, 2000.
Nelsen et al., "Porcine Reproductive and Respiratory Syndrome Virus Comparison: Divergent Evolution on Two Continents". Journal of Virology, vol. 73, No. 1, Jan. 1999, pp. 270-280.
Nelson et al., "Differentiation of U.S. and European Isolates of Porcine Reproductive and Respiratory Syndrome Virus by Monoclonal Antibodies". Journal of Clinical Microbiology, vol. 31, No. 12, Dec. 1993, pp. 3184-3189.
Nelson et al., "High affinity interaction between nucleocapsid protein and leader/intergenic sequence of mouse hepatitis virus RNA". Journal of General Virology, vol. 81, 2000, pp. 181-188.
Nielsen et al., "Generation of an Infectious Clone of VR-2332, a Highly Virulent North American-Type Isolate of Porcine Reproductive and Respiratory Syndrome Virus". Journal of Virology, vol. 77, No. 6, Mar. 2003, pp. 3702-3711.
Nishimura et al., "Replication and Synthesis of Japanese Encephalitis Virus Ribonucleic Acids in Vero Cells". Japanese Journal of Microbiology, vol. 15, No. 4, 1971, pp. 309-316.
Nodelijk et al., "A quantitative assessment of the effectiveness of PRRSV vaccination in pigs under experimental conditions". Vaccine, vol. 19, 2000, pp. 3636-3644.
Nuttall, P.A., "Growth Characteristics of Two Strains of Bovine Virus Diarrhoea Virus". Archives of Virology, vol. 66, 1980, pp. 365-369.
Oirschot et al., "Development of an ELISA for detection of antibodies to glycoprotein I of Aujeszky's disease virus: a method for the serological differentiation between infected and vaccinated pigs". Journal of Virological Methods, vol. 22, 1988, pp. 191-206.
Ojeh et al., "Isolation, characterisation and serial propagation of a Nigerian strain of porcine group A rotavirus in a monkey kidney cell line (MA104)". Discovery and Innovation, vol. 8, No. 2, Jun. 1996, pp. 159-164.
Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes". Journal of Virology, vol. 75, No. 7, Apr. 2001, pp. 3277-3290.
Oleksiewicz et al., "Semen from Boars Infected with Porcine Reproductive and Respiratory Syndrome Virus (PRRSV) Contains Antibodies Against Structural as Well as Nonstructural Viral Proteins". Veterinary Microbiology, vol. 81, 2001, pp. 109-125.
Olsthoorn et al., "A conformational switch at the 3' end of a plant virus RNA regulates viral replication". The EMBO Journal, vol. 18, No. 17, 1999, pp. 4856-4864.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and

(56) References Cited

OTHER PUBLICATIONS

Two Recent Field Isolates of PRRSV". Journal of Virology, vol. 76, No. 23, Dec. 2002, pp. 11837-11844.
Opriessnig et al., "Use of an Experimental Model to Test the Efficacy of Planned Exposure to Live Porcine Reproductive and Respiratory Syndrome Virus". Clinical and Vaccine Immunology, vol. 14, No. 12, Dec. 2007, pp. 1572-1577.
Ostrowski et al., "Identification of Neutralizing and Nonneutralizing Epitopes in the Porcine Reproductive and Respiratory Syndrome Virus GP5 Ectodomain". Journal of Virology, vol. 76, No. 9, May 2002, pp. 4241-4250.
Pan et al., "Replication of African swine fever virus in cell cultures". American Journal of Veterinary Research, vol. 41, No. 9, Sep. 1980, pp. 1357-1367.
Parratt et al., "Radioimmunoassay of Antibody and its Clinical Applications". John Wiley & Sons, Chichester, 1982, p. 43.
Parsley et al., "Poly (rC) binding protein 2 forms a ternary complex with the 5'-terminal sequences of poliovirus RNA and the viral 3CD proteinase". RNA, vol. 3, 1997, pp. 1124-1134.
Patriarca, et al., "Lack of Significant Person-to-Person Spread of Swine Influenza-Like Virus Following Fatal Infection in an Immunocomprised Child". American Journal of Epidemiology, vol. 119, No. 2, 1984, pp. 152-158.
Paul et al., "Porcine Reproductive and Respiratory Syndrome: An Overview". Journal of Clinical Veterinary Medicine, vol. 11, No. 12, Nov. 1993, pp. 1-16.
Pearson et al., "Improved tools for biological sequence comparison". Proceedings of the National Academy of Sciences, vol. 85, Apr. 1988, pp. 2444-2448.
Pedersen et al., "Open Reading Frame 1a-Encoded Subunits of the Arterivirus Replicase Induce Endoplasmic Reticulum-Derived Double-Membrane Vesicles Which Carry the Viral Replication Complex". Journal of Virology, vol. 73, No. 3, Mar. 1999, pp. 2016-2026.
Pejsak et al., "Clinical signs and economic losses caused by porcine reproductive and respiratory syndrome virus in a large breeding farm". Veterinary Microbiology, vol. 44, 1997, pp. 317-322.
Peng et al., "Analysis of Second-Site Revertants of a Murine Coronavirus Nucleocapsid Protein Deletion Mutant and Construction of Nucleocapsid Protein Mutants by Targeted RNA Recombination". Journal of Virology, vol. 69, No. 6, Jun. 1995, pp. 3449-3457.
Penzes et al., "Characterization of a Replicating and Packaged Defective RNA of Avian Coronavirus Infectious Bronchitis Virus". vol. 203, No. 2, Sep. 1994, pp. 286-293.
Percy et al., "Expression of a Foreign Protein by Influenza A Virus". Journal of Virology, vol. 68, No. 7, Jul. 1994, pp. 4486-4492.
Pirtle et al., "Morphologic Heterogeneity of a Strain of Swine Influenza Virus (A/Swine/Wisconsin/1/68, Hsw1N1) Propagated at Different Temperatures". American Journal of Veterinary Research, vol. 36, No. 1, 1975, pp. 1783-1787.
Plagemann et al., "Lactate Dehydrogenase-Elevating Virus, Equine Arteritis Virus, and Simina Hemorrhagic Fever Virus: A New Group of Positive-Strand RNA Viruses". Advances in Virus Research, vol. 41, 1991, pp. 99-192.
Pol et al., "Pathological, ultrastructural, immunohistochemical changes caused by Lelystad virus in experimentally induced infections of mystery swine disease (synonym: porcine epidemic abortion and respiratory syndrome (PEARS))". Veterinary Quarterly, vol. 13, No. 3, Jul. 1991, pp. 137-143.
Polson et al., "An evaluation of the financial impact of Porcine Reproductive and Respiratory Syndrome (PRRS) in nursery pigs". Proceedings of the 13th International Pig Veterinary Society Congress, Jun. 1994, p. 31.
Polson et al., "Financial Implications of Mystery Swine Disease (MSD)". 1993, pp. 8-28.
Polson, DD, "Answers to Your Questions on PRRS". NOBL Laboratories, 1993, 18 Pages.
Polson, DD, "RespPRRS a PRRS Vaccine Review", NOBL Laboratories, 1993, 22 pages.

Porcine Reproductive and Respiratory Syndrome: A Report on the Seminar Held in Brussels on Nov. 4-5, 1991 and Organized by the European Commission.
Poser, C.M., "Swine Influenza Vaccination: Truth and Consequences". Archives of Neurology, vol. 42, No. 11, 1985, pp. 1090-1092.
Potgieter et al., "Isolation of Swine Influenza Virus in Oklahoma". Journal of the American Veterinary Medical Association, vol. 171, No. 8, 1977, pp. 758-760.
Potts et al., "Peroxidase-labeled primary antibody method for detection of pestivirus contamination in cell cultures". Journal of Virological Methods, vol. 26, No. 1, Oct. 1989, pp. 119-124.
Quaife, T. "Mystery Agent Isolated! Isolation of the etiological agent behind mystery swine disease is a major breakthrough". Swine Practitioner, Mystery Disease: Part 8, Nov. 1991, pp. 4-7.
Reed et al., "A Simple Method of Estimating Fifty Per Cent Endpoints"., The American Journal of Hygiene, vol. 27, No. 3, May 1938, pp. 493-497.
Reed et al., "Persistent Respiratory Virus Infection in Tracheal Organ Cultures". British Journal of Experimental Pathology, vol. 50, 1969, pp. 378-388.
Rice et al., "Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants". Journal of Virology, vol. 61, No. 12, Dec. 1987, pp. 3809-3819.
Roberts et al., "Abortion in Swine". Veterinary Ostetrics and Genital Diseases, Edwards Brothers, Inc., Ann Arbor, 1986, pp. 180-192.
Roof et al., "Efficacy of Modified Live Virus Porcine Reproductive and Respiratory Virus Vaccines Against Heterologous Respiratory Challenge". 4th International Symposium on Emerging and Re-emerging Pig Diseases, Rome, Jun. 28-Jul. 2, 2003, pp. 117-118.
Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.
Rossow et al., "Experimental porcine reproductive and respiratory syndrome virus infection in one-, four-, and 10-week-old pigs". Journal of Veterinary Diagnostic Investigation, vol. 6, 1993, pp. 3-12.
Rossow, K.D., "Porcine Reproductive and Respiratory Syndrome". Veterinary Pathology, vol. 35, 1998, pp. 1-20.
Roth et al., "Influenza virus hemagglutinin expression is polarized in cells infected with recombinant SV40 viruses carrying cloned hemagglutinin DNA". Cell, vol. 33, No. 2, Jun. 1983, pp. 435-443.
Roth et al., "The large external domain is sufficient for the correct sorting of secreted or chimeric influenza virus hemagglutinins in polarized monkey kidney cells". The Journal of Cell Biology, vol. 104, Mar. 1987, pp. 769-782.
Rottier et al., "Predicted Membrane Topology of the Coronavirus Protein E1". Biochemistry, vol. 25, 1986, pp. 1335-1339.
Rovira et al., "Experimental Inoculation of Conventional Pigs with Porcine Reproductive and Respiratory Syndrome virus and Porcine Circovirus 2", J. Virol, jApr. 2002, vol. 76, No. 7, pp. 3232-3239.
Sagripanti et al., "The Cap Structure of Simian Hemorrhagic Fever Virion RNA". Virology, vol. 151, 1986, pp. 143-150.
Saif et al., "Serial propagation of porcine group C rotavirus (pararotavirus) in a continuous cell line and characterization of the passaged virus". Journal of Clinical Microbiology, vol. 26, No. 7, Jul. 1988, pp. 1277-1282.
Saif, L.J., "Coronavirus Immunogens". Veterinary Microbiology, vol. 37, No. 3-4, Nov. 1993, pp. 285-297.
Sarnow, P. "Role of 3'-End Sequences in Infectivity of Poliovirus Transcripts Made In Vitro". Journal of Virology, vol. 63, No. 1, Jan. 1989, pp. 467-470.
Sawicki et al., "Coronavirus Transcription: Subgenomic Mouse Hepatitis Virus Replicative Intermediates Function in RNA Synthesis". Journal of Virology, vol. 64, No. 3, Mar. 1990, pp. 1050-1056.
Schmidt et al., "Infection of Influenza A Viruses of Tracheal Organ Cultures Derived from Homologous and Heterologous Hosts". The Journal of Infectious Diseases, vol. 129, No. 1, 1974, pp. 28-36.
Scott, F.W., "Immunization against feline coronaviruses". Advances in Experimental Medicine and Biology, vol. 218, 1987, pp. 569-576.

(56) References Cited

OTHER PUBLICATIONS

Seal et al., "Analysis of the Serologic Relationship among San Miguel Sea Lion Virus and Vesicular Exanthema of Swine Virus Isolates. Application of the Western Blot Assay for Detection of Antibodies in Swine Sera to these Virus Types". Journal of Veterinary Diagnostic Investigation, vol. 7, No. 2, Apr. 1995, pp. 190-195.

Seal et al., "Isolation of caliciviruses from skunks that are antigenically and genotypically related to San Miguel sea lion virus Original Research". Virus Research, vol. 37, No. 1, Jun. 1995, pp. 1-12.

Seneca, H., "Influenza: epidemiology, etiology, immunization and management". Journal of American Geriatrics Society, vol. 28, No. 6, Jun. 1980, pp. 241-250.

Sethna et al., "Coronavirus subgenomic minus-strand RNAs and the potential for mRNA replicons". Proceedings of the National Academy of Sciences, vol. 86, Jul. 1989, pp. 5626-5630.

Setzer et al., "Size Heterogeneity in the 3' End of Dihydrofolate Reductase Messenger RNAs in Mouse Cells". Cell, vol. 22, Nov. 1980, pp. 361-370.

Shaw et al., "Experimental rotavirus infection in three-week-old pigs". American Journal of Veterinary Research, vol. 50, No. 11, Nov. 1989, pp. 1961-1965.

Shen et al., "Determination of the complete nucleotide sequence of a vaccine strain of porcine reproductive and respiratory syndrome virus and identification of the Nsp2 gene with a unique insertion". Archives of Virology, vol. 145, No. 5, May 2000, pp. 871-883.

Shibata et al., "Detection of Human Papilloma Virus in Paraffin-Embedded Tissue Using the Polymerase Chain Reaction". The Journal of Experimental Medicine, vol. 167, No. 1, Jan. 1988, pp. 225-230.

Shieh et al., "The 5'-End Sequence of the Murine Coronavirus Genome: Implications of Multiple Fusion Sites in Leader-Primed Transcription". Virology, vol. 156, 1987, pp. 321-330.

Shin et al., "Assessment of Porcine Reproductive and Respiratory Syndrome Virus RNA Load in Sera and Tissues during Acute Infection". Journal of Veterinary Science, vol. 3, No. 2, 2002, pp. 75-85.

Shope et al., "The Susceptibility of Swine to the Virus of Human Influenza". Annual Meeting of the Society of American Bacteriologists in New York, 1936, pp. 791-801.

Shortridge et al., "Geographical Distribution of Swine (HSw1N1) and Hong Kong (H3N2) Influenza Virus Variants in Pigs in Southeast Asia". Intervirology, vol. 11, No. 1, 1979, pp. 9-15.

Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine". Journal of Virology, vol. 73, No. 2, Feb. 1999, pp. 1374-1381.

Smith et al., "Isolation of Swine Influenza Virus from Autopsy Lung Tissue of Man". New England Journal of Medicine, vol. 294, Mar. 1976, pp. 708-710.

Smith et al., "San Miguel Sea Lion Virus Isolation, Preliminary Characterization and Relationship to Vesicular Exanthema of Swine Virus". Nature, vol. 244, Jul. 1973, pp. 108-110.

Snijder et al., "A 3'-Coterminal Nested Set of Independently Transcribed mRNAs is Generated during Berne Virus Replication". Journal of Virology, vol. 64, No. 1, Jan. 1990, pp. 331-338.

Snijder et al., "Identification of a Novel Structural Protein of Arteriviruses". Journal of Virology, vol. 73, No. 8, Aug. 1999, pp. 6335-6345.

Snijder et al., "Non-structural proteins 2 and 3 interact to modify host cell membranes during the formation of the arterivirus replication complex". Journal of General Virology, vol. 83, 2001, pp. 985-994.

Snijder et al., "Proteolytic Processing of the Replicase ORF1a Protein of Equine Arteritis Virus". Journal of Virology, vol. 68, No. 9, Sep. 1994, pp. 5755-5764.

Snijder et al., "The carboxyl-terminal part of the putative Berne virus polymerase is expressed by ribosomal frameshifting and contains sequence motifs which indicate that toro- and coronaviruses are evolutionarily related". Nucleic Acids Research, vol. 18, No. 15, Aug. 1990, pp. 4535-4542.

Snijder et al., "The molecular biology of arteriviruses". Journal of General Virology, vol. 79, 1998, pp. 961-979.

Snijder et al., "Toroviruses: replication, evolution and comparison with other members of the coronavirus-like superfamily". Journal of General Virology, vol. 74, 1993, pp. 2305-2316.

Spaan et al., "Coronaviruses: Structure and Genome Expression". Journal of General Virology, vol. 69, 1988, pp. 2939-2952.

Stephen et al., "Swine Influenza Virus Vaccine: Potentiation in Rhesus Monkeys in Antibody Responses by a Nuclease Resistant Derivative of Ply I-Poly C". U.S. Army Medical Research Institute of Infectious Diseases, Fort Detrick, Frederick, MD 21701, 1976, 10 pages.

Stephen et al., "Swine influenza virus vaccine: potentiation of antibody responses in rhesus monkeys". Science, vol. 197, No. 4310, 1977, pp. 1289-1290.

Stevenson et al., "Endemic Porcine Reproductive and Respiratory Syndrome Virus Infection of Nursery Pigs in Two Swine Herds without Current Reproductive Failure". Journal of Veterinary Diagnostic Investigation, vol. 5, 1993, pp. 432-434.

Stim, T.B., "Arbovirus Plaquing in Two Simian Kidney Cell Lines". Journal of General Virology, vol. 5, No. 3, Oct. 1969, pp. 329-338.

Suarez et al., "Direct detection of the porcine reproductive and respiratory syndrome (PRRS) virus by reverse polymerase chain reaction (RT-PCR)". Archives of Virology, vol. 135, No. 1-2, 1994, pp. 89-99.

Suarez et al., "Phylogenetic relationships of European strains of porcine reproductive and respiratory syndrome virus (PRRSV) inferred from DNA sequences of putative ORF-5 and ORF-7 genes". Virus Research, vol. 42, Nos. 1-2, Jun. 1996, pp. 159-165.

Sumiyoshi et al., "Infectious Japanese Encephalitis Virus RNA Can Be Synthesized from In Vitro-Ligated cDNA Templates". Journal of Virology, vol. 66, No. 9, Sep. 1992, pp. 5425-5431.

Tahara et al., "Coronavirus Translational Regulation: Leader Affects mRNA Efficiency". Virology, vol. 202, No. 1, Aug. 1994, pp. 621-630.

Tao et al., "Host Range Restriction of Parainfluenza Virus Growth Occurs at the Level of Virus Genome Replication". Virology, vol. 220, 1996, pp. 69-77.

Tauraso et al., "Simian Hemorrhagic Fever: III. Characterization of a Viral Agent". The American Journal of Tropical Medicine and Hygiene, vol. 17, No. 3, May 1968, pp. 422-431.

Terpstra et al., "Experimental reproduction of porcine epidemic abortion and respiratory syndrome (mystery swine disease) by infection with Lelystad virus: Koch's postulates fulfilled". The Veterinary Quarterly, vol. 13, No. 3, Jul. 1991, pp. 131-136.

Thacker, B., "Clinical Manifestations of PRRS Virus". 2003 PRRS Compendium: Second Edition, National Pork Board, Des Moines, IA, 2003, pp. 7-15.

Thanawongnuwech et al., "Effects of Low (Modified-live Virus Vaccine) and High (VR-2385)-Virulence Strains of Porcine Reproductive and Respiratory Syndrome Virus on Pulmonary Clearance of Copper Particles in Pigs" Veterinary Pathology, vol. 35, 1998, pp. 398-406.

Theil et al., "Isolation and Serial Propagation of Turkey Rotaviruses in a Fetal Rhesus Monkey Kidney (MA104) Cell Line". Avian Diseases, vol. 30, No. 1, 1985, pp. 93-104.

Kreutz, L.C., "Cellular membrane factors are the major determinants of porcine reproductive and respiratory syndrome virus tropism". Virus Research, vol. 53, 1998, pp. 121-128.

Kundin, W.D., "Hong Kong A-2 Influenza Virus Infection among Swine during a Human Epidemic in Taiwan". Nature, vol. 228, Nov. 1970, p. 857.

Kuo et al., "A Nested Set of Eight RNAs is Formed in Macrophages Infected with Lactate Dehydrogenase-Elevating Virus", Journal of Virology, vol. 65, No. 9, Sep. 1991, pp. 5118-5123.

Kusanagi et al., "Isolation and Serial Propagation of Porcine Epidemic Diarrhea Virus in Cell Cultures and Partial Characterization of the Isolate". Journal of Veterinary Medical Science, vol. 54, No. 2, 1992, pp. 313-318.

(56) References Cited

OTHER PUBLICATIONS

Kutsuzawa et al., "Isolation of Human Rotavirus Subgroups 1 and 2 in Cell Culture". Journal of Clinical Microbiology, vol. 16, No. 4, Oct. 1982, pp. 727-730.

Kwang et al., "Cloning, expression, and sequence analysis of the ORF4 gene of the porcine reproductive and respiratory syndrome virus MN-1b". Journal of Veterinary Diagnostic Investigation, vol. 6, No. 3, Jul. 1994, pp. 293-296.

Labarque et al., "Effect of cellular changes and onset of humoral immunity on the replication of porcine reproductive and respiratory syndrome virus in the lungs of pigs". Journal of General Virology, vol. 81, 2000, pp. 1327-1334.

Labarque et al., "Respiratory tract protection upon challenge of pigs vaccinated with attenuated porcine reproductive and respiratory syndrome virus vaccines". Veterinary Microbiology, vol. 95, 2003, pp. 187-197.

Lai et al., "Coronavirus: how a large RNA viral genome is replicated and transcribed". Infectious Agents and Disease, vol. 3, Nos. 2-3, 1994, pp. 98-105.

Lai et al., "Coronavirus: organization, replication and expression of genome". Annual Review of Microbiology, vol. 33, 1990, pp. 303-333.

Lai et al., "Infectious RNA transcribed from stably cloned full-length cDNA of dengue type 4 virus". Proceedings of the National Academy of Sciences, vol. 88, Jun. 1991, pp. 5139-5143.

Lazar et al., "Transforming Growth Factor a: Mutation of Aspartic Acid 47 and Leucine 48 Results in Different Biological Activities". Molecular and Cellular Biology, vol. 8, No. 3, Mar. 1988, pp. 1247-1252.

Leitner et al., "DNA and RNA-based vaccines: principles, progress and prospects". Vaccine, vol. 18, 2000, pp. 765-777.

Levy et al., "Freeze-drying is an effective method for preserving infectious type C retroviruses". Journal of Virological Methods, vol. 5, Nos. 3-4, Nov. 1982, pp. 165-171.

Liljestrom et al., "A New Generation of Animal Cell Expression Vectors Based on the Semliki Forest Virus Replicon". Nature Biotechnology, vol. 9, 1991, pp. 1356-1361.

Lin et al., "Deletion Mapping of a Mouse Hepatitis Virus Defective Interfering RNA Reveals the Requirement of an Internal and Discontiguous Sequence fro Replication". Journal of Virology, vol. 67, No. 10, Oct. 1993, pp. 6110-6118.

Lin et al., "Identification of the cis-Acting Signal for Minus-Strand RNA Synthesis of a Murine Coronavirus: Implications for the Role of Minus-Strand RNA in RNA Replication and Transcription". Journal of Virology, vol. 68, No. 12, Dec. 1994, pp. 8131-8140.

Lin et al., "The 3' Untranslated Region of Coronavirus RNA is Required for Subgenomic mRNA Transcription from a Defective Interfering RNA". Journal of Virology, vol. 70, No. 10, Oct. 1995, pp. 7236-7240.

Liu et al., "A Specific Host Cellular Protein Binding Element Near the 3? End of Mouse Hepatitis Virus Genomic RNA". Virology, vol. 232, No. 1, May 1997, pp. 74-85.

Loula, T., "Clinical Presentation of Mystery Pig Disease in the Breeding Herd and Suckling Piglets". Proceedings of the Mystery Swine Disease Committee Meeting, Denver, CO, Oct. 6, 1990, pp. 37-40.

Loula, T., "Mystery Pig Disease", Agri-Practice, vol. 12, No. 1, Jan.-Feb. 1991, pp. 29-34.

Luytjes et al., "Replication of Synthetic Defective Interfering RNAs Derived from Coronavirus Mouse Hepatitis Virus—A59". Virology, vol. 216, No. 1, Feb. 1996, pp. 174-183.

Lv et al., "An infectious cDNA clone of a highly pathogenic porcine reproductive and respiratory syndrome virus variant associated with porcine high fever syndrome". Journal of General Virology, vol. 89, 2008, pp. 2075-2079.

Madec et al., "Consequences pathologiques d'un épisode grippal severe (virus swine A/H1N1 dans les conditions naturelles chez la truie non immune en debut de gestation". Comparative Immunology, Microbiology and Infectious Diseases, vol. 12, Nos. 1-2, 1989, pp. 17-27.

Madin, S.H. "Vesicular Exanthema Virus". Virus Infections of Porcines, Elsevier Science Publishers B.V., 1989, pp. 267-271.

Makabe et al., "Hemagglutination with Ovine Rotavirus". Archives of Virology, vol. 90, 1986, pp. 153-158.

Makino et al., "Leader sequences of murine coronavirus mRNAs can be freely reassorted: Evidence for the role of free leader RNA in transcription". Proceedings of the National Academy of Sciences, vol. 83, Jun. 1986, pp. 4204-4208.

Makino et al., "Primary Structure and Translation of a Defective Interfering RNA of Murine Coronavirus". Virology, vol. 166, 1988, pp. 550-560.

Mardassi et al., "Identification of major differences in the nucleocapsid protein genes of a Québec strain and European strains of porcine reproductive and respiratory syndrome virus". vol. 75, No. 3, Mar. 1994, pp. 681-685.

Mardassi et al., "Molecular analysis of the ORFs 3 to 7 of porcine reproductive and respiratory syndrome virus, Québec reference strain". Archives of Virology, vol. 140, No. 8, 1995, pp. 1405-1418.

Mason, P.W., "Maturation of Japanese encephalitis virus glycoproteins produced by infected mammalian and mosquito cells". Virology, vol. 169, No. 2, Apr. 1989, pp. 354-364.

Masters et al., "Functions of the coronavirus nucleocapsid protein". Coronaviruses and Their Diseases, Plenum Press, New York, pp. 235-238.

Masurel, N., "Swine Influenza Virus and the Recycling of Influenza-A Viruses in Man". The Lancet, Jul. 31, 1976, pp. 244-247.

McAuliffe et al., "Codon Substitution Mutations at Two Positions in the L Polymerase Protein of Human Parainfluenza Virus Type 1 Yield Viruses with a Spectrum of Attenuation In Vivo and Increased Phenotypic Stability In Vitro". Journal of Virology, vol. 78, No. 4, Feb. 2004, pp. 2029-2036.

McCullough et al., "9. Experimental Transmission of Mystery Swine Disease", The New Pig Disease Porcine Respiration and Reproductive Syndrome, A report on the seminar/workshop held in Brussels on Apr. 29-30, 1991, pp. 46-52.

McDaniel, H.A., "African Swine Fever". Diseases of Swine, 5th Edition, Chapter 18, The Iowa State University Press, Ames, Iowa, 1981, pp. 237-245.

McFerran, J.B., "Reovirus Infection". Diseases of Swine, Fifth Edition, Chapter 28, The Iowa State University Press, Ames, Iowa, 1981, pp. 330-334.

McIntosh, "Diagnostic Virology". Fields Virology, Ch. 17, Second Edition, vol. 1, 1990, pp. 411-437.

McKinney, W.P., "Fatal Swine Influenza Pneumonia During Late Pregnancy". Archives of Internal Medicine, vol. 150, No. 1, Jan. 1990, pp. 213-215.

McQueen et al., "Influenza in animals". Advances in Veterinary Science, vol. 12, 1968, pp. 285-336.

Meikeljohn et al., "Respiratory Virus Vaccine Evaluation and Surveillance". Semi-Annual Contract Progress Report to the National Institute of Allergy and Infectious Diseases, Sep. 15, 1965 to Mar. 15, 1966, 21 pgs.

Melchers et al., "Cross-talk between orientation-dependent recognition determinants of a complex control RNA element, the enterovirus oriR". RNA, vol. 6, 2000, pp. 976-987.

Mendez et al., "Molecular Characterization of Transmissible Gastroenteritis Coronavirus Defective Interfering Genomes: Packaging and Heterogeneity". Virology, vol. 217, 1996, pp. 495-507.

Meng et al., "Characterization of a High-Virulence US Isolate of Porcine Reproductive and Respiratory Syndrome Virus in a Continuous Cell Line, ATCC CRL11171". Journal of Veterinary Diagnostic Investigation, vol. 8, No. 3, Jul. 1996, pp. 374-381.

Meng et al., "Molecular cloning and nucleotide sequencing of the 3'-terminal genomic RNA of the porcine reproductive and respiratory syndrome virus". Journal of General Virology, vol. 75, 1994, pp. 1795-1801.

Meng et al., "Phylogenetic analyses of the putative M (ORF 6) and N (ORF 7) genes of porcine reproductive and respiratory syndrome virus (PRRSV): implication for the existence of two genotypes of PRRSV in the U.S.A. and Europe". Archives of Virology, vol. 140, No. 4, 1995, pp. 745-755.

(56) References Cited

OTHER PUBLICATIONS

Meng, X.J., "Heterogeneity of porcine reproductive and respiratory syndrome virus: implications for current vaccine efficacy and future vaccine development". Veterinary Microbiology, vol. 74, 2000, pp. 309-329.

Mengeling et al., "An update of research at the National Animal Disease Center on current field strains of Porcine Reproductive and Respiratory Syndrome (PRRS) virus". Allen D. Leman Swine Conference, 1997, pp. 138-145.

Mengeling et al., "Clinical consequences of exposing pregnant gilts to strains of porcine reproductive and respiratory syndrome (PRRS) virus isolated from field cases of "atypical" PRRS". American Journal of Veterinary Research, vol. 59, No. 12, Dec. 1998, pp. 1540-1544.

Mengeling et al., "Clinical Effects of porcine reproductive and respiratory syndrome virus on pigs during the early postnatal interval". American Journal of Veterinary Research, vol. 59, No. 1, Jan. 1998, pp. 52-55.

Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.

Wensvoort et al., "Mystery Swine Disease in the Netherlands the Isolation of Lelystad Virus". The Veterinary Quarterly, vol. 13, No. 3, 1991, pp. 121-130.

Wensvoort et al., "Production of Monoclonal Antibodies Against Swine Fever Virus and Their Use in Laboratory Diagnosis". Veterinary Microbiology, vol. 12, 1986, pp. 101-108.

Wensvoort et al., "The Porcine Reproductive and Respiratory Syndrome; Characteristics and diagnosis of the causative virus". Veterinary Biotechnology Newsletter, vol. 3, 1993, pp. 113-120.

Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.

Westenbrink et al., "An enzyme-linked immunosorbent assay for detection of antibodies to porcine parvovirus". Journal of Virological Methods, vol. 23, 1989, pp. 169-178.

Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.

Witte, K.H. "The Situation of 'Epidemic Late Abortion of Swine' in the State of Northrhine—Westphalia". Workshop Seminar, Apr. 1991.

Woode, et al., "Porcine Rotavirus Infection". Diseases of Swine, Fifth Edition, Chapter 26, The Iowa State University Press, Ames, Iowa, 1981, pp. 310-322.

Woods et al., "Antigenicity of Inactivated Swine Influenza Virus Concentrated by Centrifugation". Research Communications in Chemical Pathology and Pharmacology, vol. 13, No. 1, 1976, pp. 129-132.

Woods et al., "Experimental challenge of pregnant gilts with swine influenza virus after vaccination". Research Communications in Chemical Pathology and Pharmacology, vol. 15, No. 4, Dec. 1976, pp. 787-795.

Woods et al., "Investigation of Four Outbreaks of Acute Respiratory Disease in Swine and Isolation of Swine Influenza Virus". Health Laboratory Science, vol. 5, No. 4, Oct. 1968, pp. 218-224.

Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, pp. 37-38.

Yamane et al., "Annual Examination of Influenza Virus Infection Among Pigs in Miyagi Prefecture, Japan: The Appearance of Hsw1N1 Virus". Acta Virologica, vol. 23, 1979, pp. 240-248.

Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.

Yoon et al., "A modified serum neutralization test for the detection of antibody to porcine reproductive and respiratory syndrome virus in swine sera". Journal of Veterinary Diagnostic Investigation, vol. 6, No. 3, Jul. 1994, pp. 289-292.

Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.

Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.

Yu et al., "Specific Binding of Host Cellular Proteins to Multiple Sites within the 39 End of Mouse Hepatitis Virus Genomic RNA". Journal of Virology, vol. 69, No. 4, Apr. 1995, pp. 2016-2023.

Yuan et al., "Complete genome comparison of porcine reproductive and respiratory syndrome virus parental and attenuated strains". Virus Research, vol. 74, 2001, pp. 99-110.

Yuan et al., "Erratum to 'Complete genome comparison of porcine reproductive and respiratory syndrome virus parental and attenuated strains'[Virus Research 74 (2001) 99-110]". Virus Research, vol. 79, 2001, p. 187.

Yuan et al., "Molecular characterization of a highly pathogenic strain of PRRSV associated with porcine High Fever syndrome in China". 2007 International Porcine Reproductive and Respiratory Syndrome (PRRS) Symposium, Chicago, Illinois, Nov.-Dec. 2007, Poster 70.

Yuan et al., American Society for Virology, 16th Annual Meeting, Bozeman, Montana, Jul. 19-23, 1997, Abstract P29-5, p. 229.

Zeijst, et al., "The Genome of Equine Arteritis Virus". Virology, vol. 68, 1975, pp. 418-425.

Zhou et al., "Generation of cytotoxic and humoral immune responses by nonreplicative recombinant Semliki Forest virus". Proceedings of the National Academy of Sciences, vol. 92, Mar. 1995, pp. 3009-3013.

Zimmerman et al., "General overview of PRRSV: A perspective from the United States". Veterinary Microbiology, vol. 55, Nos. 1-4, Apr. 1997, pp. 187-196.

Carvajal et al., "Evaluation of a Blocking ELISA Using Monoclonal Antibodies for the Detection of Porcine Epidemic Diarrhea Virus and Its Antibodies". Journal of Veterinary Diagnostic Investigation, vol. 7, No. 1, Jan. 1995, pp. 60-64.

Cavanagh, D., "Nidovirales: a new order comprising Coronaviridae and Arteriviridae". Archives of Virology, vol. 142, No. 3, 1997, pp. 629-633.

Chang et al., "A cis-Acting Function for the Coronavirus Leader in Defective Interfering RNA Replication". Journal of Virology, vol. 68, No. 12, Dec. 1994, pp. 8223-8231.

Chang et al., "Evolution of Porcine Reproductive and Respiratory Syndrome Virus during Sequential Passages in Pigs". Journal of Virology, vol. 76, No. 10, May 2002, pp. 4750-4763.

Chao et al., "Monoclonal Antibodies to Metacyclic Stage Antigens of Trypanosoma Cruzi" The American Journal of Tropical Medicine and Hygiene, vol. 34, No. 4, Jul. 1985, pp. 694-701.

Charley, B., "Interaction of influenza virus with swine alveolar macrophages: Influence of anti-virus antibodies and cytochalasin B". Annales de l'Instiut Pasteur. Virologie, vol. 134, No. 1, Jan. 1983, pp. 51-59.

Chasey et al., "Replication of Atypical Ovine Rotavirus in Small Intestine and Cell Culture". Journal of General Virology, vol. 67, No. 3, Mar. 1986, pp. 567-576.

Chen et al., "Determination of the 5' end of the lactate dehydrogenase-elevating virus genome by two independent approaches". Journal of General Virology, vol. 75, 1994, pp. 925-930.

Christianson et al., "Experimental Reproduction of a Newly Described Viral Disease, Swine Infertility and Respiratory Syndrome (SIRS), in Pregnant Sows". 72nd Annual Meeting of the Conference of Research Workers in Animal Disease, Chicago, IL, Nov. 11 & 12, 1991, p. 48, Abstract No. 269.

(56) References Cited

OTHER PUBLICATIONS

Christianson et al., "Experimental reproduction of swine infertility and respiratory syndrome in pregnant sows". American Journal of Veterinary Research, vol. 53, No. 4, Apr. 1992, pp. 485-488.
Christianson et al., "Porcine reproductive and respiratory syndrome: A review"., Journal of Swine Health and Production, vol. 2, No. 2, Mar. and Apr. 1994, pp. 10-28.
Christianson et al., "Swine Infertility and Respiratory Syndrome". Pig Veterinary Journal, vol. 27, No. 9, Apr. 1991, pp. 9-12.
Chutivongse et al., "One-year study of the 2-1-1 intramuscular postexposure rabies vaccine regimen in 100 severely exposed Thai patients using rabies immune globulin and Vero cell rabies vaccine". Vaccine, vol. 9, No. 8, Aug. 1991, pp. 573-576.
Clark et al., "Trypsin enhancement of rotavirus infectivity: mechanism of enhancement". Journal of Virology, vol. 39, No. 3, Sep. 1981, pp. 816-822.
Collins et al., "Experimental Transmission of Swine Reproductive Failure Syndrome (Mystery Swine Disease) in Gnotobiotic Piglets". 71st Annual Meeting of the Conference of Research Workers in Animal Disease, Chicago, IL, Nov. 5-6, 1990, Abstract No. 2.
Collins et al., "Isolation of swine infertility and respiratory syndrome virus (isolate ATCC VR-2332) in North America and experimental reproduction of the disease in gnotobiotic pigs". Journal of Veterinary Diagnostic Investigation, vol. 4, 1992, pp. 117-126.
Collins et al., "Production of infectious human respiratory syncytial virus from cloned cDNA confirms an essential role for the transcription elongation factor from the 5' proximal open reading frame of the M2 mRNA in gene expression and provides a capability for vaccine development". Proceedings of the National Academy of Sciences, vol. 92, Dec. 1995, pp. 11563-11567.
Collins et al., "Respiratory Disease in a Swine Herd Experiencing a Reproductive Failure Syndrome". Minnesota Swine Conference for Veterinarians, Sep. 16-18, 1990, pp. 206-207.
Collins et al., "Swine Diagnostic Pathology". Allen D. Leman Swine Conference, College of Veterinary Medicine, University of Minnesota, Sep. 18-22, 1998, pp. 1-4.
Collins et al., "Swine Infertility and Respiratory Syndrome (Mystery Swine Disease)". Minnesota Swine Conference for Veterinarians, St. Paul, MN, Sep. 15-17, 1991, pp. 200-205.
Collins, J.E., "Newly Recognized Respiratory Syndromes in North American Swine Herds". American Association of Swine Practitioners Newsletter, vol. 3, No. 7, Sep.-Oct. 1991, pp. 7, 10-11.
Conner et al., "Isolation and characteristics of an equine reovirus type 3 and an antibody prevalence survey to reoviruses in horses located in New York State". Veterinary Microbiology, vol. 9, No. 1, Feb. 1984, pp. 15-25.
Conzelmann et al., "Molecular Characterization of Porcine Reproductive and Respiratory Syndrome Virus, a Member of the Arterivirus Group". Virology, vol. 193, 1993, pp. 329-339.
Cooper et al., "Porcine Reproductive and Respiratory Syndrome: NEB-1 PRRSV Infection did not Potentiate Bacterial Pathogens". Journal of Veterinary Diagnostic Investigation, vol. 7, No. 3, Jul. 1995, pp. 313-320.
Corn et al., "Isolation of Vesicular Stomatitis Virus New Jersey Serotype from Phlebotomine Sand Files in Georgia". The American Journal of Tropical Medicine and Hygiene, vol. 42, No. 5, May 1990, pp. 476-482.
Dacso, et al., "Sporadic occurrence of zoonotic swine influenza virus infections". Journal of Clinical Microbiology, vol. 20, No. 4, Oct. 1984, pp. 833-835.
Database WPIL Week 8702, Derwent Publications Ltd., London, GB; AN 87-009295 [2] & EP, A,208672 (Regional Wallonne-Chiron Corp, Wallonne Regional) Jan. 14, 1987.
Database WPIL Week 8741, Derwent Publications Ltd., London, GB; AN 87-286929 [41] & EP, A,62, 198626 (ZA Bieseibutsu Kagaku Ken) Sep. 2, 1987.
Database WPIL Week 8821, Derwent Publications Ltd., London, GB; AN 88-147502 [21] & WO,A,8 803 410 (Inst Pasteur) May 19, 1988.

De Mazancourt et al., "Antibody response to the rubella virus structural proteins in infants with the congenital rubella syndrome". Journal of Medical Virology, vol. 19, No. 2, Jun. 1986, pp. 111-122.
De Vries et al., "Genetic Manipulation of Equine Arteritis Virus Using Full-Length cDNA Clones: Separation of Overlapping Genes and Expression of a Foreign Epitope". Virology, vol. 270, No. 1, 2000, pp. 84-97.
De Vries et al., "The Genome Organization of the Nidovirales: Similarities and Differences between Arteri-, Toro-, and Coronaviruses". Seminars in Virology, vol. 8, 1997, pp. 33-47.
De Vries, et al., "All subgenomic mRNAs of equine arteritis virus contain a common leader sequence". Nucleic Acids Research, vol. 18, No. 11, 1990, pp. 3241-3247.
Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.
Dea et al., "Antigenic variant of swine influenza virus causing proliferative and necrotizing pneumonia in pigs". Journal of Veterinary Diagnostic Investigation, vol. 4, No, 4, 1992, pp. 380-392.
Dea et al., "Caracteristiques d'Isolats des virus influenza et de l'encephalomyocardite associes au Syndrome Reproducteur et Respiratoire Porcine (S.R.R.P.) au Quebec.sup.a," Le Medecin Veterinaire Du Quebec, vol. 21, No. 4, Nov. 1991, pp. 170-175.
Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.
Dea et al., "Isolation of encephalomyocarditis virus among stillborn and post-weaning pigs in Quebec". Archives of Virology, vol. 117, Nos. 1-2, 1991, pp. 121-128.
Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.
Dea et al., "Virus Isolations from Farms in Quebec Experiencing Severe Outbreaks of Respiratory and Reproductive Problems". Proceedings of the Mystery Swine Disease Committee Meeting, Denver, CO, Oct. 6, 1990, pp. 67-72.
Del Val et al., "Glycosylated components of African swine fever virus particles". Virology, vol. 152, No. 1, Jul. 1986, pp. 39-49.
Den Boon et al., "Equine Arteritis Virus is Not a Togavirus but Belongs to the Coronaviruslike Superfamily". Journal of Virology, vol. 65, No. 6, 1991, pp. 2910-2920.
Den Boon et al., "Processing and Evolution of the N-Terminal Region of the Arterivirus Replicase ORF1a Protein: Identification of Two Papainlike Cysteine Proteases". Journal of Virology, vol. 69, No. 7, Jul. 1995, pp. 4500-4505.
Deng et al., "An improved procedure for utilizing terminal transferase to add homopolymers to the 3' termini of DNA". Nucleic Acids Research, vol. 9, No. 16, 1981, pp. 4173-4188.
Derbyshire, J.B. "Porcine Enterovirus Infections". Diseases of Swine, Fifth Edition, Chapter 20, 1981, pp. 265-270.
Devereux et al., "A Comprehensive Set of Sequence Analysis Programs for VAX". Nucleic Acids Research, vol. 12, No. 1, 1984, pp. 387-395.
Dianzani et al., "Is Human Immunodeficiency Virus RNA Load Composed of Neutralized Immune Complexes". The Journal of Infectious Diseases, vol. 185, 2002, pp. 1051-1054.
Dildrop et al., "Immunoglobulin V region variants in hybridoma cells. II. Recombination between V genes". The EMBO Journal, vol. 1, No. 5, 1982, pp. 635-640.
Dreher, T.W., "Functions of the 3'-Untranslated Regions of Positive Strand RNA Viral Genomes". Annual Review of Phytopathology, vol. 37, 1999, pp. 151-174.
Drew et al., "Production, characterization and reactivity of monoclonal antibodies to porcine reproductive and respiratory syndrome virus". Journal of General Virology, vol. 76, 1995, pp. 1361-1369.
Drew, T., "Porcine Reproductive and Respiratory Syndrome Virus: A Review". Apr. 1996, 3 pages.

(56) References Cited

OTHER PUBLICATIONS

Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.

Duan et al. "Recombinant Baculovirus Vaccines Against Porcine Reproductive and Respiratory Syndrome (PRRS)". Abstracts PRRS, Aug. 9 to 10, 1995, Copenhagen, Denmark, 2 pages.

Dykhuizen et al., "Determining the Economic Impact of the 'New' Pig Disease", Porcine Reproductive and Respiratory Syndrome, A Report on the Seminar Held in Brussels on Nov. 4-5, 1991 and Organized by the European Commission, pp. 53-60.

Easterday, B.C., "Swine Influenza". Diseases of Swine, Sixth Edition, Iowa State University Press, 1986, pp. 244-315. (Part One of Two—pp. 244-285). This NPL is too large for EFS submission. Therefore filing in two parts.

Easterday, B.C., "Swine Influenza". Diseases of Swine, Sixth Edition, Iowa State University Press, 1986, pp. 244-315. (Part Two of Two—pp. 286-315). This NPL is too large for EFS submission. Therefore filing in two parts.

Easterday, et al., "Swine Influenza". In Diseases of Swine (8th Edition), BE Straw, S D'Allaire, WI. Mengeling, DJ Taylor, eds., Ames: Iowa State University Press, 1999, pp. 277-290.

Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, pp. 5227-5232.

Ehresmann et al., "RNA synthesized in calicivirus-infected cells is atypical of picornaviruses". Journal of Virology, vol. 22, No. 2, May 1977, pp. 572-576.

Ellis, R.W., "New Technologies for Making Vaccines". Vaccines, Chapter 29, Plotkin et al Eds., WB Saunders Company, Philadelphia, PA, 1988, pp. 568-575.

Enjuanes et al., "Isolation and Properties of the DNA of African Swine Fever (ASF) Virus". Journal of General Virology, vol. 32, No. 3, Sep. 1976, pp. 479-492.

*Enzo Biochem Inc. v. Gen-Probe Incorporated et al.*, No. 01-01230; Decided Jul. 15, 2002.

Estes et al., "Simian rotavirus SA11 replication in cell cultures". Journal of Virology, vol. 31, No. 3, Sep. 1979, pp. 810-815.

Fang et al., "Heterogeneity in nsp2 of European-like porcine reproductive and respiratory syndrome viruses isolated in the United States". Virus Research, vol. 100, 2004, pp. 229-235.

Fenner et al., "Immunization against Viral Diseases", Veterinary Virology, Ch. 14, 1992, pp. 265-271.

Fenner et al., "Viral Genetics and Evolution", Veterinary Virology, Ch. 5, 1992, pp. 89-95.

Ferrari et al., "Isolation of Cytopathic Strains of Rotavirus from Pigs". Microbiologica, vol. 9, No. 3, Jul. 1986, pp. 287-294.

Flint et al., "Virus Cultivation, Detection, and Genetics". Virology, Molecular Biology, Pathogenesis, and Control, Ch. 2, 2000, pp. 40-42.

Foss et al., "Adjuvant Danger Signals Increase the Immune Response to Porcine Reproductive and Respiratory Syndrome Virus". Viral Immunology, vol. 15, No. 4, 2002, pp. 557-566.

Frolov et al., "Alphavirus-based expression vectors: Strategies and applications". Proceedings of the National Academy of Sciences, vol. 93, Oct. 1996, pp. 11371-11377.

Fu et al., "Detection and survival of group a rotavirus in a piggery". Veterinary Record, vol. 125, 1989, pp. 576-578.

Fukuhara et al., "Evidence for endocytosis-independent infection by human rotavirus". Archives of Virology, vol. 97, Nos. 1-2, 1987, pp. 93-99.

Funkhouser et al., "Mutations in the 5'-noncoding, 2C and P3 Regions of the Genome Increase the Efficiency of Hepatitis A Virus Growth in MRC-5 Cells". Vaccines, vol. 94, Cold Springs Harbor Laboratory Press, 1994, pp. 345-349.

Garwes, D.J., "Transmissible gastroenteritis". Veterinary Record, vol. 122, 1988, pp. 462-463.

Geisbert et al., "Use of Immunoelectron Microscopy to Show Ebola Virus During the 1989 United States Epizootic". Journal of Clinical Pathology, vol. 43, No. 10, Oct. 1990, pp. 813-816.

Girard et al., "Experimentally induced porcine proliferative and necrotising pneumonia with an influenza A virus". The Veterinary Record, vol. 130, Mar. 1992, pp. 206-207.

Godeny et al., "Map location of lactate dehydrogenase-elevating virus (LDV) capsid protein (Vp1) gene", Virology, vol. 177, No. 2, Aug. 1990, pp. 768-771.

Godeny et al., "The 3' Terminus of Lactate Dehydrogenase-Elevating Virus Genome RNA Does Not Contain Togavirus or Flavivirus Conserved Sequences", Virology, vol. 72, 1989, pp. 647-650.

Goldfield et al., "Influenza in New Jersey in 1976: Isolations of Influenza A/New Jersey/76 Virus at Fort Dix". The Journal of Infectious Diseases, vol. 136, Supp. 3, 1977, pp. S347-S355.

Goldstein, et al., "Evaluation of Three Cell Culture Systems as Substrates for Influenza Virus Assay". Applied Microbiology, vol. 19, No. 4, Apr. 1970, pp. 580-582.

Gong et al., "Characterization of RNA synthesis during a one-step growth curve and of the replication mechanism of bovine viral diarrhoea virus". Journal of General Virology, vol. 77, 1996, pp. 2729-2736.

Gorcyca et al., RespPRRS: A new tool for the prevention and control of PRRS in pigs. Proceedings of the American Association of Swine Practitioners, Omaha, Nebraska, Mar. 1995, pp. 1-22.

Gourreau et al., "Diffusion du virus de la grippe du porc (H1N1=Hsw1N1) en France". Annales de l'Institut Pasteur/Virologie, vol. 132, No. 2, Apr.-Jun. 1981, pp. 287-294.

Goyal, S., "Porcine Reproductive and Respiratory Syndrome", Journal of Veterinary Diagnostic Investigation, vol. 5, No. 4, 1993, pp. 656-664.

Gravell et al., "Differences among isolates of simian hemorrhagic fever (SHF) virus". Proceedings of the Society for Experimental Biology and Medicine, vol. 181, No. 1, 1986, pp. 112-119.

Graves, J.H., "Swine Vesicular Disease". Diseases of Swine, Fifth Edition, Chapter 23, The Iowa State University Press, Ames, Iowa, 1958, pp. 288-293.

Grebennikova et al., "Genomic characterization of virulent, attenuated, and revertant passages of a North American porcine reproductive and respiratory syndrome virus strain". Virology, vol. 321, 2004, pp. 383-390.

Greiner et al., "Quantitative relationship of systemic virus concentration on growth and immune response in pigs". Journal of Animal Science, vol. 78, 2000, pp. 2690-2695.

Grizzard et al., "Experimental production of respiratory tract disease in cebus monkeys after intratracheal or intranasal infection with influenza A/Victoria/3/75 or influenza A/New Jersey/76 virus". Infection and Immunity, vol. 21, No. 1, Jul. 1978, pp. 201-205.

Grouse, L.D., "Swine Flue Sequelae"., Journal of the American Medical Association, vol. 243, No. 24, 1980, p. 2489.

Grunert et al., "Sensitivity of Influenza A/New Jersey/8/76 (Hsw1N1) Virus to Amantadine-HCI". Journal of Infectious Diseases, vol. 136, No. 2, 1977, pp. 297-300.

Guan et al., "Requirement of a 5?-Proximal Linear Sequence on Minus Strands for Plus-Strand Synthesis of a Satellite RNA Associated with Turnip Crinkle Virus". Virology, vol. 268, No. 2, Mar. 2000, pp. 355-363.

Gubler et al., "A simple and very efficient method for generating cDNA libraries". Gene, vol. 25, 1983, pp. 263-269.

Gustafson, D.P., "Pseudorabies". Diseases of Swine, Fifth Edition, Ch. 14, The Iowa State University Press, Ames, Iowa, 1981, pp. 209-223.

Halbur et al., "Comparative pathogenicity of nine US porcine reproductive and respiratory syndrome virus (PRRSV) isolates in a five-week-old cesarean-derived, colostrum-deprived pig model". Journal of Veterinary Diagnostic Investigation, vol. 8, 1996, pp. 11-20.

Halbur et al., "Effects of different US isolates of porcine reproductive and respiratory syndrome virus (PRRSV) on blood and bone marrow parameters of experimentally infected pigs". Veterinary Record, vol. 151, 2002, pp. 344-348.

Halbur et al., "Variable Pathogenicity of Nine Porcine Reproductive and Respiratory Syndrome Virus (PRRSV) Isolates". Conference of

(56) References Cited

OTHER PUBLICATIONS

Research Workers in Animal Diseases, Abstracts of Papers, Chicago, Illinois, paper #222, Nov. 1993.
Halbur et al., "Viral Pneumonia in Neonatal and Nursery pigs. Experimental Work with SIRS Agent and Evidence of Another New Viral Agent". Agri-Practice, vol. 12, No. 1, Jan.-Feb. 1991, pp. 23-34.
Hao et al., "Polymorphic genetic characterization of the ORF7 gene of porcine reproductive and respiratory syndrome virus (PRRSV) in China". Virology Journal, vol. 8:73, pp. 1-9.
Harlow & Lane, Editors, "Antibodies, A Laboratory Manual". Cold Spring Harbor: Cold Spring Harbor Laboratory, New York, 1988, pp. 423, 464-468.
Darwich et al., "Genetic and immunobiological diversities of porcine reproductive and respiratory syndrome genotype I strains". Veterinary Microbiology, vol. 150, 2011, pp. 49-62.
International Search Report and Written Opinon for PCT/EP2012/052476 dated May 7, 2012.
Matanin et al., "Purification of the major envelop protein GP5 of porcine reproductive and respiratory syndrome virus (PRRSV) from native virions". Journal of Virological Methods, vol. 147, 2008, pp. 127-135.
Pesch et al., "New insights into the genetic diversity of European porcine reproductive and respiratory syndrome virus (PRRSV)". Veterinary Microbiology, vol. 107, 2005, pp. 31-48.
Gao et al., "Genomic characterization of two Chinese isolates of Porcine respiratory and reproductive syndrome virus*". Archives of Virology, vol. 149, 2004, pp. 1341-1351.
UniProt: Accession No. C9E449. "SubName: Full=M protein; SubName: Full= Membrane protein". Nov. 3, 2009.
UniProt: Accession No. D0VEE4. "SubName: Full=Unglycosylated membrane protein". Dec. 15, 2009.
UniProt: Accession No. Q6TLB4. "SubName: Full= Membrane protein M". Jul. 5, 2004.
Cano et al., "Impact of a modfied-live porcine reproductive and respiratory syndrome virus vaccine intervention on a population of pigs infected with a heterologous isolate". Vaccine, vol. 25, 2007, pp. 4382-4391.
Brockmeier et al., "Genomic sequence and virulence comparison of four Type 2 porcine reproductive and respiratory syndrome virus strains". Virus Research, vol. 169, No. 1, 2012, pp. 212-221.
Charerntantanakul et al., "Porcine reproductive and respiratory syndrome virus vaccines: Immunogenicity, efficacy and safety aspects". World Journal of Virology, vol. 1, No. 1, Feb. 2012, pp. 23-30.
Collins et al., "Laboratory diagnosis of porcine reproductive and respiratory syndrome (PRRS) virus infection". Swine Health and Production, vol. 4, No. 1, Feb. 1996, pp. 33-35.
Database EMBL Accession No. EF488739, "Porcine respiratory and reproductive syndrome virus isolate MN184C, complete genome". Apr. 19, 2007, pp. 1-4.
Database EMBL Accession No. EU759247, "Porcine respiratory and reproductive syndrome virus isolate PRRSV2000000079 envelope glycoprotein gene, complete cds". Aug. 10, 2008, 1 page.
Kvisgaard et al., "Genetic and antigenic characterization of complete genomes of Type 1 Porcine Reproductive and Respiratory Syndrome viruses (PRRSV) isolated in Denmark over a period of 10 years". Virus Research, vol. 178, 2013, pp. 197-205.
Leng et al., "Evaluation of the Efficacy of an Attenuated Live Vaccine against Highly Pathogenic Porcine Reproductive and Respiratory Syndrome Virus in Young Pigs". Clinical and Vaccine Immunology, vol. 19, No. 8, Aug. 2012, pp. 1199-1206.
NCBI: Accession No. B4ZWR2. "Porcine reproductive and respiratory syndrome virus (PRRSV)." May, 2008, 1 page.
Prieto et al., "Similarity of European porcine reproductive and respiratory syndrome virus strains to vaccine strain is not necessarily predictive of the degree of protective immunity conferred". The Veterinary Journal, vol. 175, No. 3, Mar. 2008, pp. 356-363.
UniProt: Accession No. B4ZUF3. "SubName: Full=Envelope glycoprotein". Sep. 23, 2008, 1 page.
UniProt: Accession No. J9QHK0. "SubName: Full=Nucleocapsid protein". Nov. 28, 2012, 1 page.
UniProt: Accession No. J9QII1. "SubName: Full=Unglycosylated membrane protein". Nov. 28, 2012, 1 page.
UniProt: Accession No. J9QIW4. "SubName: Full=Polyprotein lab". Nov. 28, 2012, pp. 1-3.

* cited by examiner

FIG 8

```
        ┌─────────────────────────┐
        │   AK MA104              │
        │ Cell Planting and Infection │
        └─────────────────────────┘
                   │
                   ▼
        ┌─────────────────────────┐
        │ Post-infection          │
        │ Refers to the period of │
        │ time between infection  │       
        │ and Harvest 1           │        5-7 days
        └─────────────────────────┘
                   │
                   ▼
        ┌─────────────────────────┐
        │ 1st Harvest             │
        │ Refers to the point after│
        │ infection when is       │
        │ antigen is harvested    │
        └─────────────────────────┘
                   │
  Virus            ▼
  Propagation   ┌─────────────────────────┐
        ┌──────│ Re-Feed (RF)            │
        │      │ Refers to the period of │
        │      │ time between infection  │
        │      │ and Harvest 1           │
        │      └─────────────────────────┘
        │                │                  2 days    7-9 days
        │                ▼
        │      ┌─────────────────────────┐
        │      │ 2nd Harvest             │
        │      │ the point when the antigen is │
        │      │ harvested after the Re-Feed │
        │      └─────────────────────────┘
        │                │
        │                ▼
        │      ┌─────────────────────────┐
        │      │ 2nd Re-Feed (RF)        │
        │      │ Refers to the period of │
        │      │ time between infection  │    2 days    9-11 days
        │      │ and Harvest 3           │
        │      └─────────────────────────┘
        │                │
        │                ▼
        │      ┌─────────────────────────┐
        └──────│ 3rd Harvest             │
               │ Is the point when the antigen is │
               │ harvested after the 2nd Re-Feed │
               └─────────────────────────┘
```

COMMERCIAL SCALE PROCESS FOR PRODUCTION OF PRRSV

FIELD OF THE INVENTION

The present invention relates to commercial scale production of live attenuated Porcine Reproductive and Respiratory Syndrome Virus (PRRSV) which may be used in the production of vaccines based thereon and the use thereof in the treatment of swine.

BACKGROUND OF THE INVENTION

Porcine reproductive and respiratory syndrome (PRRS) is viewed by many as the most important disease currently affecting the pig industry worldwide. The syndrome first was described in 1987 in the United States as "mystery swine disease" and rapidly spread across the globe. It causes severe reproduction losses, is associated with increased mortality due to secondary infections, and is linked to reduced feed conversion and average daily weight gain. Unfortunately, control of the virus that causes PRRS has proven to be difficult.

PRRS virus (PRRSV) is an enveloped single stranded RNA virus classified in the family Arteriviridae (Cavanaugh, 1997). It causes a widespread disease of swine that was first described as 'mystery swine disease' in the USA in 1987 (Hill, 1990). The disease manifests as respiratory illness in all age groups of swine leading to death in some younger pigs and severe reproductive problems in breeding age females.

Transmission of the PRRSV can, and often does, occur through direct contact between infected and susceptible pigs. Transmission over very short distances by air or through semen also may occur. Once infected, the virus can remain in the blood of adults for about two to four weeks, and in infected pigs for one to two months or more. Infected boars may shed the virus in the semen for more than 100 days. This long period of viremia significantly increases the possibility of transmission. In addition, the PRRS virus can cross the placenta during the last third of the gestation period to infect piglets in utero and cause stillbirth or weak-born piglets.

All types and sizes of herds, including those with high or ordinary health status or from either indoor or outdoor units, can be infected with PRRS virus. Infected herds may experience severe reproductivity losses, as well as, increased levels of post weaning pneumonia with poor growth. The reproductive phase typically lasts for two to three months; however, post weaning problems often become endemic. The reproductive disease is characterized by an abortion outbreak that affects both sows and gilts in the last term of gestation. Premature farrowings around 109 and 112 days of gestation occur. The number of stillbirths and weak-born piglets increases and results in a considerable increase in pre-weaning mortality.

The respiratory phase traditionally has been seen in the nursery, especially in continuous flow nurseries. However, respiratory problems caused by PRRS virus can also be seen in the finisher as part of the porcine respiratory disease complex (PRDC). A reduction in growth rate, an increase in the percentage of unmarketable pigs, and elevated post weaning mortality can occur. Diagnostic findings indicate high levels of pneumonia that associate with the PRRS virus together with a wide variety of other microbials commonly seen as secondary infectious agents. Bacterial isolates may include *Streptococcus suis*, *Haemophilus suis*, *Actinobacillus pleuropneumoniae*, *Actinobacillus suis*, *Mycoplasma hyopneumoniae*, and *Pasteurella multocida* among others. Viral agents commonly involved include swine influenza virus and porcine respiratory corona virus. Affected pigs rarely respond to high levels of medication, and all-in/all-out systems have failed to control the disease.

PRRSV virus exists as two genotypes referred to as "US" and "EU" type which share about 50% sequence homology (Dea S et al. (2000). Arch Virol 145:659-88). These two genotypes can also be distinguished by their immunological properties. Most sequencing information on various isolates is based on the structural proteins, namely the envelope protein GP5 which accounts for only about 4% of the viral genome, while only little is known on the non-structural proteins (nsp). Isolation of PRRSV and manufacture of vaccines have been described in a number of publications (WO 92/21375, WO 93/06211, WO93/03760, WO 93/07898, WO 96/36356, EP 0 676 467, EP 0 732 340, EP 0 835 930).

Vaccination is the key method for alleviating the burden of PRRS as pigs that recover from a PRRS infection will develop an immune response, which under normal circumstances will protect them from being infected again by the same virus strain. However, PRRS virus has the ability to change because of the high rate of by mutation that often occurs in positive, single-stranded, RNA viruses; and therefore, new viral strains may arise. In such cases, cross protection between strains may not exist, and new outbreaks may be observed in farms that had been infected previously. Thus there is a continuing need for additional vaccines.

The most frequently used method for producing attenuated, live-virus vaccine is to serially passage the virus in a substrate (usually cell culture with a cell line that is permissive to the virus) other than the natural host (S) until it becomes sufficiently attenuated (i.e., reduced in virulence or diseases-producing ability) to be used as a vaccine. For the first passage, a cell culture is infected with the selected inoculum. After obtaining clear evidence of virus replication (e.g., virus-induced cytopathic effects [CPE] in the infected cells), an aliquot of the cell culture medium, or infected cells, or both, of the first passage are used to infect a second cell culture. The process is repeated until one or more critical mutations in the viral genome cause sufficient attenuation so that the virus can be safely used as a vaccine. The degree of attenuation is usually determined empirically by exposing the natural host (S) to progressively greater passage levels of the virus.

The above procedure is fundamentally sound and has been successfully used for the development of numerous vaccines for human and veterinary use. However, when it comes to industrial scale production, there remains a need to provide an efficient and cost-effective method for production of PRRSV.

BRIEF SUMMARY OF THE INVENTION

The present invention is related to a new method for the production of live PRRS virus for use in the manufacture of such vaccines. The methods described herein may be used in the large scale production of any PRRS virus, including but not limited to including but not limited to PRRSV 94881 PRRSV strain 94881 deposited with the European Collection of Cell Cultures (ECACC) under the Accession Numbers ECACC 11012501 and ECACC 11012502 each deposited on Jan. 25, 2011 in accordance with the provisions of the Budapest Treaty, or any descendant or progeny of one of the aforementioned strains.

More particularly, the present invention relates to a method for the commercial scale production of porcine reproductive and respiratory syndrome virus (PRRSV) comprising:

a) concurrently seeding a large scale culture media with a mammalian cell line that is permissive to PRRSV infection into a bioreactor and infecting the mammalian cells with a PRRSV.

b) propagating virus for 5 to 7 days post infection;

c) performing a first harvesting step by removing the media from the bioreactor and isolating propogated virus therefrom;

d) replenishing the media in the bioreactor and propagating virus for 1 to 4 days;

e) performing a second harvesting step by removing the media from the bioreactor and isolating propogated virus therefrom;

f) replenishing the media in the bioreactor and propagating virus for 1 to 4 days and g) performing a third harvesting step by removing the media from the bioreactor and isolating propogated virus therefrom.

In certain embodiments, the method may further comprise at least one re-feeding and harvest steps subsequent to the third harvesting step comprising replenishing the media in the bioreactor and propagating virus for 1 to 4 days and performing a fourth harvesting step by removing the media from the bioreactor and isolating propogated virus therefrom.

Preferably, in the method of production the target multiplicity of infection (MOI) is 0.01 to 0.30 and the mammalian cells are planted at a density of about $7 \times 10^8$ to $1.0 \times 10^9$ per 300 L bioreactor. More particularly, the cell planting density is about $1.0 \times 10^9$ per 300 L bioreactor. In specific embodiments, the MOI is about $7 \times 10^8$ virus particles.

The method may comprise monitoring the dextrose concentration of the media wherein the first harvest step is performed on the first day when the dextrose concentration of the media decreases to less than 0.1 g/L.

In the commercial production method, the second harvest is preferably performed 1 or 2 days post-refeeding with media, and the third harvest is performed 1 to 4 days post the second refeeding with media.

In specific embodiments, the culture media is added to the bioreactor on the day prior to or on the same day prior to addition of the mammalian cell line and the PRRS. Preferably, the culture media is added to the bioreactor one day prior to the addition of the mammalian cell line and the PRRS. The temperature of the bioreactor is set at between 34° C. and 38° C.

In specific embodiments, the media comprises 5% v/v irradiated fetal calf serum.

The method may be used for the commercial scale production of any PRRSV, including but not limited to PRRSV selected from the group consisting of PRRSV 94881 PRRSV strain 94881 deposited with the European Collection of Cell Cultures (ECACC) under the Accession Numbers ECACC 11012501 and ECACC 11012502 each deposited on Jan. 25, 2011 in accordance with the provisions of the Budapest Treaty, VR 2332, Lelystad virus strain (Lelystad Agent (CDI-NL-2.91), or other strains such as those deposited under the Accession Numbers ECACC 04102703, ECACC 04102702, ECACC 04102704, CNCM Accession No. I-1140, CNCM Accession No I-1387, CNCM Accession No I-1388, ATCC VR 2332, VR 2385, VR 2386, VR 2429, VR 2474, and VR 2402; CNCM I-1102, CNCM I-1140, CNCM I-1387, CNCM I-1388, or ECACC V93070108; ATCC deposit VR-2332, ATCC deposit VR-2368; ATCC VR-2495; ATCC VR 2385, ATCC VR 2386, ATCC VR 2429, ATCC VR 2474, and ATCC VR 2402, or any descendant or progeny of one of the aforementioned strains.

Also contemplated is a commercial-scale production method for the preparation of a PRRSV comprising:

a. a concurrent seeding of both mammalian cells permissive to infection by the PRRSV and the PRRSV into a bioreactor containing a media suitable for the growth of the cells; and b. performing three consecutive harvesting steps wherein PRRSV is harvested wherein after each of the first and second harvests, the media is replenished, and wherein:

i. the first harvest is performed on the first day that the dextrose concentration of the media decreases to less than 0.1 g/L;

ii. the second harvest is performed 1 or 2 days after addition of the media following the first harvest; and iii. the third harvest is performed between 1 and 4 days after addition of the media following the second harvest. An alternative method is also contemplated that uses a concurrent roller bottle process that is equivalent to the bioreactor process described above. More particularly, the present invention relates to a method for the commercial scale production of porcine reproductive and respiratory syndrome virus (PRRSV) comprising: a) concurrently seeding a large scale culture media with a mammalian cell line that is permissive to PRRSV infection into a roller bottles and infecting said mammalian cells with a PRRSV; b) propagating virus for 5 to 7 days post infection; c) performing a first harvesting step by removing the media from said roller bottle and isolating propogated virus therefrom; d) replenishing the media in said roller bottle and propagating virus for about 2 days; e) performing a second harvesting step by removing the media from said roller bottle and isolating propogated virus therefrom; f) replenishing the media in said roller bottle and propagating virus for about 2 days and g) performing a third harvesting step by removing the media from said bioreactor and isolating propogated virus therefrom.

Another aspect of the invention relates to a PRRSV MLV comprising a PRRSV produced according to the methods described herein formulated with an acceptable adjuvant or carrier for delivery to a pig.

BRIEF DESCRIPTION OF SEVERAL VIEWS OF THE DRAWINGS

FIG. 8: Definition and Timelines of the concurrent process for the roller bottle process.

DETAILED DESCRIPTION OF THE INVENTION

Figure 1:
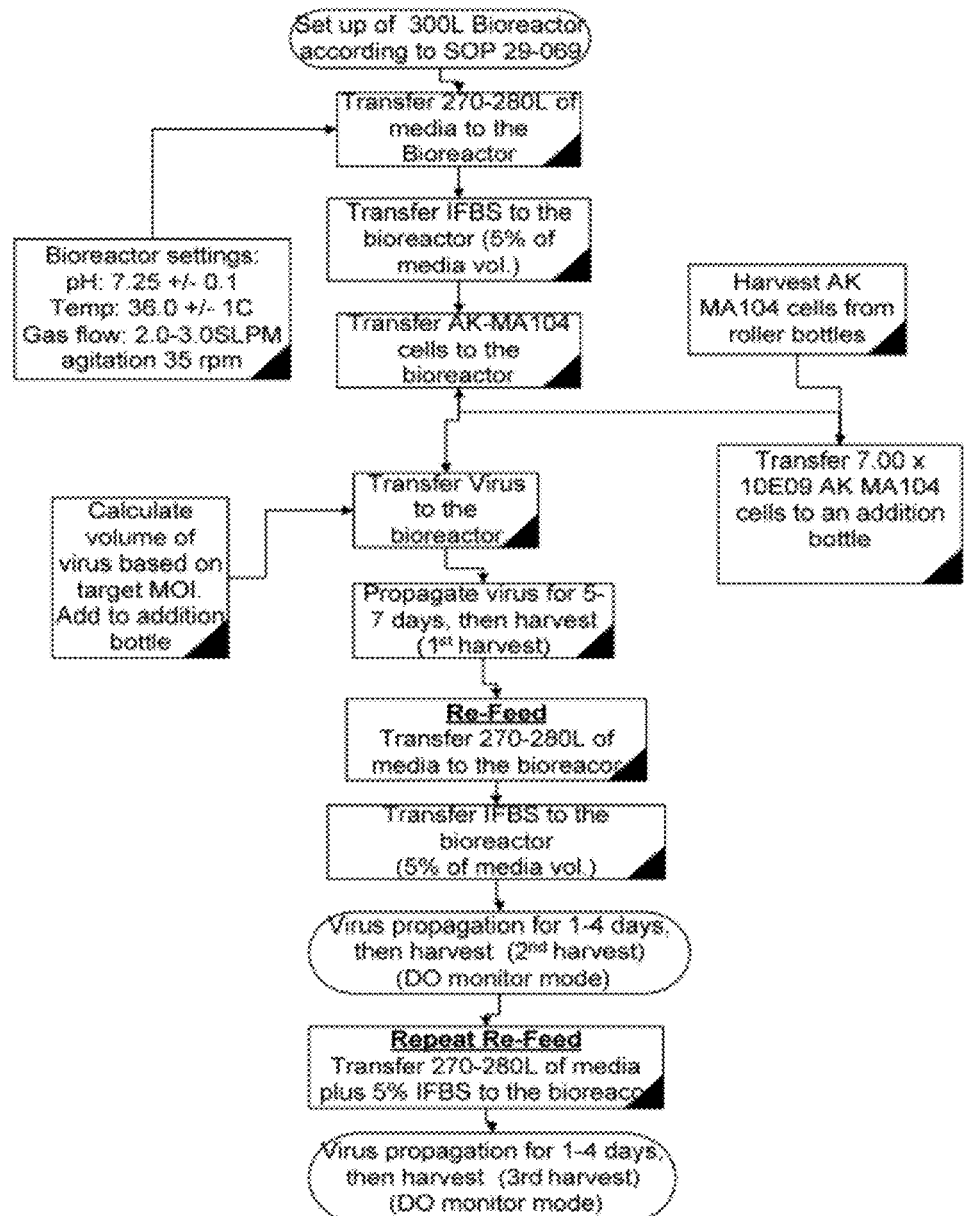
FIG. 1: Concurrent process for large-scale production of PRRSV 94881.
Figure 2:
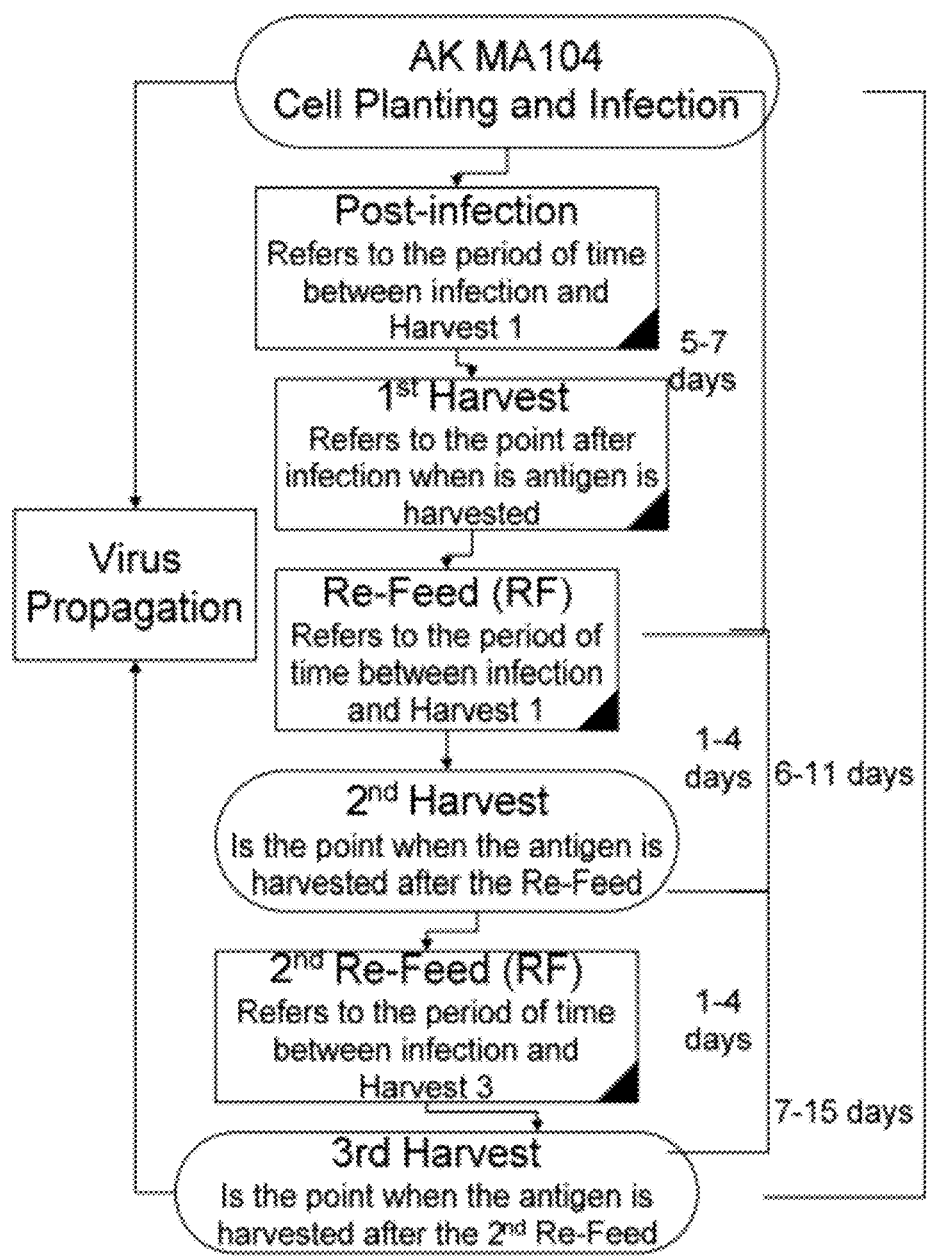
FIG. 2: Definition and Timelines of the concurrent process for the 300 L Bioreactors FIG. 3 Viral titers and dextrose profiles for the three concurrent runs in the 300 L Bioreactors.

The present invention provides methods for the large scale production of live porcine reproductive and respiratory syndrome virus (PRRSV) for use in the production of vaccines and other compositions. In typical production methods, the virus is grown on a cell line that is permissive to PRRSV infection. However, in such general methods the cell line is grown to at or near confluence prior to infection with the PRRSV. In the present invention, the inventors have unexpectedly demonstrated that the cell line does not need to be planted and grown prior to infection with PRRSV, but rather that the PRRSV and the cell line may be added to the cell culture process concurrently. This invention thus provides the significant advantage of savings in time, cost and materials when the virus is being mass produced at commercial scale. The term commercial scale refers to volumes of cell culture in excess of 10 L. For example, commercial scale refers to a range of from 10 L to 3000 L production scale for live PRRSV. In more specific embodiments, the volume is from 30 L to about 300 L.

The methods of the present invention may be used for the production of any PRRSV strain, including but not limited to PRRSV strain deposited as ATCC VR 2332, VR 2385, VR 2386, VR 2429, VR 2474, and VR 2402; CNCM I-1102, CNCM I-1140, CNCM I-1387, CNCM I-1388, or ECACC V93070108. In particularly preferred embodiments, the methods of the invention are used to produce PRRSV strain 94881 deposited with the European Collection of Cell Cultures (ECACC) under the Accession Numbers ECACC 11012501 (parental strain) and ECACC 11012502 (high passage attenuated MSV) each deposited on Jan. 25, 2011 in accordance with the provisions of the Budapest Treaty, or any descendant or progeny of one of the aforementioned strains. The viruses grown may be any of the aforementioned viruses in their attenuated format. Alternatively, the viruses may be genetically modified to comprise one or more heterologous nucleic acids that encode further antigenic determinants of one or more swine diseases.

The skilled person will understand that there are a number of cell lines that are permissive to infection by PRRSV. Exemplary cells are cells porcine alveolar macrophage cells such as those derived from MARC-145 cells. Other cells that can be infected with the PRRSV include MA-104 cells; Baby Hamster Kidney (BHK) cells; Chinese Hamster Ovary (CHO) cells; and African Green Monkey kidney cells other than MA-104 cells or MARC-145 cells, such as VERO cells; that are transfected. In addition, the cells may be primary cells from a swine animal that have been adapted for long term growth in culture. Particularly suitable host cells are the simian cell line MA-104, Vero cells, or porcine alveolar macrophages. PRRSV preferentially grows in alveolar lung macrophages (Wensvoort et al., 1991). A few cell lines, such as CL2621 and other cell lines cloned from the monkey kidney cell line MA-104 (Benfield et al., 1992; Collins et al., 1992; Kim et al., 1993) are also susceptible to the virus and may be used in the large-scale production methods described herein.

In the exemplary method of the present invention shown in Example 1 below there is provided a concurrent process for the production of PRRSV 94881 MLV. While this procedure is shown for PRRSV 94881 MLV skilled person will understand that this procedure may be readily used for any PRRSV for which large scale production is required.

The viruses produced by the production method of the invention may be used for any applications for which PRRSV is currently used. In a specific embodiment, the virus produced according to the methods described herein is used to prepare a PRRSV MLV.

The virus strains grown according to the methods of the invention may be virulent PRRS viruses, attenuated PRRS viruses or indeed PRRS viruses that have been modified to impart further desirable properties to them. This may be achieved by classical propagation and selection techniques, like continued propagation in suitable host cells to extend the attenuated phenotype. Alternatively, the strains may be genetically modified by directed mutation of the nucleic acid sequence of the genome of these strains by suitable genetic engineering techniques. The genome of PRRSV was completely or partly sequenced (Conzelmann et al., 1993; Meulenberg et al., 1993a, Murthaugh et al, 1995) and encodes, besides the RNA dependent RNA polymerase (ORFs 1a and 1b), six structural proteins of which four envelope glycoproteins named GP2 (ORF2), GP3 (ORF3), GP4 (ORF4) and GP5 (ORF5), a non-glycosylated membrane protein M (ORF6) and the nucleocapsid protein N(ORF7) (Meulenberg et al. 1995, 1996; van Nieuwstadt et al., 1996). Immunological characterization and nucleotide sequencing of European and US strains of PRRSV has identified minor antigenic differences within strains of PRRSV located in the structural viral proteins (Nelson et al., 1993; Wensvoort et al., 1992; Murtaugh et al., 1995).

Indeed, the exemplary virus grown in the invention is PRRSV 94881 virus. While an attenuated strain is grown using the methods described herein, the virus may easily be a PRRSV 94881 virus that is made into a chimeric virus wherein the backbone of the PRRSV 94881 virus under ECACC Accession No. 11012502 or indeed the parent strain deposited under ECACC Accession No 11012501 is modified to replace the endogenous sequence of one or more of ORF 1a, ORF 1b, ORF 2, ORF 3, ORF 4, ORF 5, ORF 6, or ORF 7 with the corresponding ORF from a different strain of PRRS virus. For example, the different strain of the PRRS virus may be a different European strain such as Lelystad virus strain (Lelystad Agent (CDI-NL-2.91), or other strains such as those deposited under the Accession Numbers ECACC 04102703, ECACC 04102702, ECACC 04102704, CNCM Accession No. I-1140, CNCM Accession No I-1387, CNCM Accession No I-1388, ATCC VR 2332, VR 2385, VR 2386, VR 2429, VR 2474, and VR 2402; CNCM I-1102, CNCM I-1140, CNCM I-1387, CNCM I-1388, or ECACC V93070108 or indeed may be a U.S. strain such as North American PRRS virus, pT7P129A; ATCC deposit VR-2332, ATCC deposit VR-2368; ATCC VR-2495; ATCC VR 2385, ATCC VR 2386, ATCC VR 2429, ATCC VR 2474, and ATCC VR 2402.

Recombinant techniques for preparing modified sequences are well known to those of skill in the art and usually employ construction of a full-length complementary DNA copies (infectious clones) of the viral genome which may then be modified by DNA recombination and manipulation methods (like site-directed mutagenesis etc.). This way, for example antigenic sites or enzymatic properties of viral proteins may be modified. Infectious clones of PRRS virus strains of European and North American genotype have been reported in the literature and may be grown using the methods of the invention.

Preferably, vaccines according to the present invention are modified live vaccines comprising one or more of these strains alive in a suitable carrier, but inactivated virus may also be used to prepare killed vaccine (KV). MLV are typically formulated to allow administration of $10^1$ to $10^7$ viral particles per dose, preferably $10^3$ to $10^5$ particles per dose, more preferably $10^4$ to $10^5$ particles per dose (4.0-5.0 $\log_{10}$ TCID$_{50}$). KV may be formulated based on a pre-inactivation titre of $10^3$ to $10^{10}$ viral particles per dose. The vaccine may comprise a pharmaceutically acceptable carrier, for example a physiological salt-solution. The vaccine may or may not comprise an adjuvant. An example of a suitable adjuvant is α-tocopherol acetate which can be obtained under the trade name Diluvac Forte®. Alternatively, for example alum based adjuvants may be used.

Pigs can be infected by PRRSV via the oronasal route. Virus in the lungs is taken up by lung alveolar macrophages and in these cells replication of PRRSV is completed within 9 hours. PRRSV travels from the lungs to the lung lymph nodes within 12 hours and to peripheral lymph nodes, bone marrow and spleen within 3 days. At these sites, only a few cells stain positive for viral antigen. The virus is present in the blood during at least 21 days and often much longer. After 7 days, antibodies to PRRSV are found in the blood. The combined presence of virus and antibody in PRRS infected pigs shows that the virus infection can persist for a long time, albeit at a low level, despite the presence of antibody. During at least 7 weeks, the population of alveolar cells in the lungs is different from normal SPF lungs.

A vaccine may be presented in form of a freeze-dried preparation of the live virus, to be reconstituted with a solvent, to result in a solution for injection. Thus, after the harvesting steps of the present invention, the virus may be combined and freeze dried. The solvent may e.g. be water, physiological saline, or buffer, or an adjuvanting solvent. The solvent may contain adjuvants, for example a-tocopherol acetate. The reconstituted vaccine may then be injected into the a pig, for example as an intramuscular or intradermal injection into the neck. For intramuscular injection, a volume of 2 ml may be applied, for an intradermal injection it is typically 0.2 ml. In a further aspect, the present invention therefore is a vaccine product, comprising in separate containers a freeze-dried composition of the virus, and a solvent for reconstitution, and optionally further containing a leaflet or label comprising instructions of use.

A vaccine prepared from a virus produced by a method of the invention may not only comprise one or more of the aforementioned strains, but may include further components active against PRRS or other porcine viral or bacterial diseases, like porcine circovirus or classical swine fever virus. Therefore, the invention further relates to a vaccine as described, characterized in that it contains at least one further antigen active against a porcine disease which is not PRRS. In addition, the vaccine may comprise certain pharmaceutically or veterinary acceptable adjuvants. One such adjuvant is α-tocopherol. Thus, new vaccine compositions, in particular, PRRS virus vaccines comprising PRRSV 94881 may be further improved by addition of adjuvants. Such improvements comprise preparation of the vaccines in combination with adjuvants that enhance the efficacy of the vaccine such that a better clinical response/outcome is seen with the administration of the combination of the adjuvant and the vaccine as compared to administration of the vaccine alone. For example, the vaccine compositions of the invention may comprise a PRRSV 94881 virus vaccine and an adjuvant selected from the group consisting of MCP-1, *Haemophilus sonmus* fractions, Carbapol™ and combinations thereof. In some embodiments, the virus vaccine comprising the PRRSV 94881 virus vaccine, which may be a recombinant subunit vaccine or alternatively may be a live attenuated virus vaccine. An exemplary live vaccine that exists is Ingelvac®PRRS MLV and the PRRSV 94881 may be formulated in a manner similar to Ingelvac®PRRS MLV.

In addition to the above, the vaccine compositions may contain other ingredients so long as the other ingredients do not interfere with the adjuvant properties of the MCP-1, *Haemophilus sonmus* fractions, Carbapol™ or other carbomer or the underlying virus vaccine. Such other ingredients include, for example, binders, colorants, desiccants, antiseptics, wetting agents, stabilizers, excipients, adhesives, plasticizers, tackifiers, thickeners, patch materials, ointment bases, keratin removers, basic substances, absorption promoters, fatty acids, fatty acid ester, higher alcohols, surfactants, water, and buffer agents. Preferred other ingredients include buffer agents, ointment bases, fatty acids, antiseptics, basic substances, or surfactants.

The content or amount of the adjuvants used in the invention may vary and can be determined by taking into consideration, for example, the properties of the PRRS virus vaccine being used, and the dosage form. The adjuvant may comprise, for example, 1 to 100% by weight. The PRRSV 94881-based compositions of the invention are produced by mixing together the adjuvant component and the virus vaccine component, either alone or with various other ingredients. The compositions may be such that the virus vaccine and the adjuvant are presented as one formulation or alternatively, the adjuvant and the vaccine are presented in distinct formulations that can be administered simultaneously or sequentially.

The adjuvant component may be administered separately from the virus vaccine in the administration to organisms. Alternatively, the adjuvant according to the present invention, together with the virus vaccine, can be administered as a single vaccine composition. The virus vaccine may be any virus vaccine. More specific embodiments contemplate the use of a PRRS virus vaccine comprising PRRSV 94881. In addition such a vaccine may be combined with other vaccines such as Ingelvac® PRRS MLV and/or Porcilis® PRRS. This is merely one exemplary PRRS virus vaccine and other such vaccines can be supplemented with the adjuvants described herein.

The immunogenic compositions described herein are particularly advantageous in the induction of the production of an antibody response to PRRS virus. In particular it is shown herein that the use of these specific adjuvants, and in particular, MCP-1, enhances immune response to PRRS virus when there is a combined administration of the adjuvant and the PRRS virus vaccine as compared to administration of vaccine alone. Such administration is shown to produce a lessening of the severity of clinical symptoms, such as lung lesions, anorexia, skin discolorations, lethargy, respiratory signs, mummified piglets, coughing, diarrhea and combinations thereof, that are associated with PRRSV infection. Indeed, there is a greater lessening of the severity of the clinical symptoms associated with PRRS virus infection observed with the combination of the vaccine and adjuvant as compared to the lessening of the severity of such symptoms produced by administration of vaccine alone in the absence of said adjuvant.

The compositions thus particularly enhance the clinical outcome in a diseased animal as compared to the outcome from administration of PRRS virus vaccine alone. In specific embodiments, the enhanced clinical outcome is a reduction of the percentage of lung lesions when compared to animals not receiving the immunogenic composition in combination with said adjuvant. In other embodiments, the enhance clinical outcome is a reduction of viremia in animals when compared to animals not receiving the immunogenic composition in combination with said adjuvant.

Thus, in one aspect, the invention relates to an improved vaccine, more particularly and improved PRRS virus vaccine, wherein the improvement comprises admixing with the virus vaccine an adjuvant selected from the group consisting of MCP-1, *Haemophilus sonmus* fractions, carbapol and combinations thereof. The vaccine composition of the invention may further comprise a pharmaceutically acceptable carrier. In addition, the vaccines may comprise other active ingredients including HS, ORF 5, INF alpha, Poly ICLC, IL-12 for further enhancing the function of the PRRS vaccine. Such adjuvants may be added alone or in combination with MCP-1.

The vaccine compositions of the invention may be formulated by any method known in the art of formulation, for example, into liquid preparations, suspensions, ointments, powders, lotions, W/O emulsions, O/W emulsions, emulsions, creams, cataplasms, patches, and gels and is preferably used as medicaments. Thus, according to another aspect of the present invention, there is provided a pharmaceutical composition comprising the above vaccine composition. The vaccine composition according to the present invention, when dermally administered, can significantly induce antibody production. Accordingly, in another preferred embodiment of the present invention, the vaccine composition can be provided as a transdermal preparation.

Further, as described above, the virus and adjuvant in the present invention may be administered, to an organism, together as a single vaccine composition, or as an adjuvant preparation separate and distinct from the antigenic PRRS virus component of the vaccine, whereby the adjuvant acts in a manner such that amount of an antibody produced in the organism in response to the PRRS virus vaccine can be significantly increased as compared to administration of the PRRS virus vaccine alone. Thus, according to a still another aspect of the present invention, there is provided a method for increasing the amount of an antibody produced against PRRS virus, the method comprising administering an immunologically effective amount of the PRRS virus vaccine, and an adjuvant selected from the group consisting of MCP-1, *Haemophilus sonmus* fractions, carbapol and combinations thereof either alone or in combination with a further component selected from the group consisting of HS, ORF 5, INF alpha, Poly ICLC, IL-12 and combinations thereof, in an amount effective as an immunoadjuvant simultaneously or successively into the organism.

When the adjuvant and the PRRS virus vaccine are administered to an organism, the clinical outcome of the animal is enhanced. The effective amount of the adjuvant and the immunologically effective amount of the PRRS virus vaccine may be properly determined by a person having ordinary skill in the art by taking into consideration, for example, the type and properties of the antigenic substance, the species of organisms, age, body weight, severity of diseases, the type of diseases, the time of administration, and administration method and further using the amount of an antibody produced against the antigenic substance in the organism as an index.

The PRRS virus vaccine, the adjuvant, or combinations thereof can be administered to organisms by any suitable method selected depending, for example, upon the condition of patients and properties of diseases. Examples of such methods include intraperitoneal administration, dermal administration (for example, subcutaneous injection, intramuscular injection, intradermal injection, and patching), nasal administration, oral administration, mucosa administration (for example, rectal administration, vaginal administration, and corneal administration). Among them, intramuscular administration is preferred.

An exemplary therapeutic dose of PRRSV MLV is about two milliliters (2 mLs). Skilled artisans will recognize that the dosage amount may be varied based on the breed, size, and other physical factors of the individual subject, as well as, the specific formulation of PRRSV MLV and the route of administration. Preferably, the PRRSV MLV is administered in a single dose; however, additional doses may be useful. Again, the skilled artisan will recognize through the present invention that the dosage and number of doses is influenced by the age and physical condition of the subject pig, as well as, other considerations common to the industry and the specific conditions under which the PRRSV MLV is administered.

In certain other embodiments, the vaccine may be a multivalent vaccine that comprises two or more PRRS viruses where at least one of the PRRS viruses is the attenuated 94881 virus deposited under ECACC Accession No. 11012502. The other PRRS viruses may be one or more selected from the group consisting of PRRSV strain deposited under the Accession Numbers Lelystad virus strain (Lelystad Agent (CDI-NL-2.91), or other strains such as those deposited under the Accession Numbers ECACC 04102703, ECACC 04102702, ECACC 04102704, CNCM Accession No. I-1140, CNCM Accession No I-1387, CNCM Accession No I-1388, ATCC VR 2332, VR 2385, VR 2386, VR 2429, VR 2474, and VR 2402; CNCM I-1102, CNCM I-1140, CNCM I-1387, CNCM I-1388, or ECACC V93070108 or indeed may be a U.S. strain such as North American PRRS virus, pT7P129A; ATCC deposit VR-2332, ATCC deposit VR-2368; ATCC VR-2495; ATCC VR 2385, ATCC VR 2386, ATCC VR 2429, ATCC VR 2474, and ATCC VR 2402.

The vaccines based on PRRS viruses may be used to vaccinate both piglets and sows. In one aspect of the invention, a particular dose regimen is selected based on the age of the pig and antigen selected for administration. This will permit pigs of any age to receive the most efficacious dose based on the present invention's discovery that PRRSV infection (from both wild type exposure and vaccination) is cleared much more quickly in older animals. Thus, in some respects, vaccination of older animals is preferred but that vaccination of younger pigs, including those three weeks of age and younger helps to induce active immunity and is still very beneficial. Animal age may be an important factor in PRRS control and may be a factor that impacts vaccination and development of an effective immune response. Thus, age, disease management, animal husbandry, innate, and active immunity are important and need to be considered in control strategies.

The PRRSV 94881 vaccine can be administered in any conventional fashion and in some preferred methods the administration is nasally. It is preferred that the administered PRRSV vaccine provide its benefits of treating or reducing the severity of or incidence of PRRSV infection after a single dose, as with Ingelvac®, however, if other antigens or combination or multivalent vaccines are selected, it should be understood that they can be administered in their conventional fashion, which may include one or more booster doses after the initial administration. Those of skill in the art will be able to determine appropriate dosing levels based on the PRRSV vaccine selected and the age range of the animal to which the antigen will be administered.

EXAMPLE 1

Exemplary Scale-Up for Production of PRRSV 94881 MLV

The 300 L bioreactor process scale up for PRRSV 94881 used MA104 cells that were between 64-84 passage. These cells were expanded in 850 cm$^2$ Roller bottles (Corning). The cells were cultured concurrently with virus infection in 300 L air-lift Bioreactors. Throughout the culture process the media dextrose/lactate concentrations were monitored in g/L. At harvest of the fluids were discarded and the virus samples were retained.

The media compositions was as shown in the following table:

| Component | Quantity |
|---|---|
| Fetal Bovine Serum Gamma irradiated | 5% |
| MEM without Phenol Red Powder | 9.6 g/L |
| Neomycin Sulfate | 30 mg/L |
| Sodium Bicarbonate | 1.4 g/L |
| Hydrochloric acid | To adjust pH |

The MEM without Phenol Red medium, neomycin and 1.4 g/L sodium bicarbonate were prepared and filtered. The FBS was added to the media concurrently with the media being placed in the bioreactor. The amount of neomycin added is calculated by: vol(L)×30 mg/L÷Potency (mg/g base).

The concurrent process for the growth of PRRSV 94881 is comprises of planting AK MA104 cells into the bioreactor and concurrently infecting the cells with the PRRSV 94881 viral seed. FIG. 1 outlines the concurrent process. In FIG. 2 there is provided timelines for the concurrent process outlined in FIG. 1.

In the concurrent process, a volume of 270 L of media was sterile filtered into the bioreactor. The media was added to the vessel on the same day or the day before the cell and serum addition. If the media is added to the bioreactor the day before the addition of the cells and serum, it is recommended that the temperature control be activated such that the media is maintained at 35° C., the pH in the control mode with the pH maintained 7.25±0.1 and DO monitor mode and agitation set at 35 rpm. At the day of the addition of the cells and irradiated fetal bovine serum (IFBS), the temperature control is set at 36° C. The IFBS is added to the bioreactor after addition of the media and before seeding of the cells. The target concentration of the IFBS is 5% v/v, which in the 270 L volume is a 14.0 L volume of IFBS per bioreactor.

Three 300 L bioreactor rounds were performed. The bioreactor parameters were: temperature set point at 36° C., pH set point at 7.25 in control mode, DO monitor and agitator at 35 rpm. Tables 3, 4, and 5 show data recorded for DO % from the OIT, dextrose and lactate from YSI, and pH and L-Glutamine from NOVA. PD titers are for reference only. QC titers are the official titers.

TABLE 3

Results for lot 00IPD-X run in 300 L bioreactor

| days | pH | DO % | Dextrose g/L YSI | Lactate g/L YSI | Gln mmol/L NOVA | Titer PD TCID50 | Titer QC TCID50 | Comments |
|---|---|---|---|---|---|---|---|---|
| −1 | 7.24 | 168 | N/A | N/A | N/A | N/A | N/A | Media only |
| 0PI | 7.2 | 92 | N/A | N/A | N/A | N/A | N/A | N/A |
| 1PI | 7.26 | 168 | 1 | 0.073 | 2.63 | 3.67 | N/A | N/A |
| 2PI | 7.25 | 83 | 0.95 | 0.12 | 2.36 | 4.9 | N/A | N/A |
| 3PI | 7.23 | 74 | 0.742 | 0.262 | 2.14 | 5.88 | N/A | N/A |
| 4PI | 7.24 | 63 | 0.408 | 0.58 | 1.72 | 6.45 | 7.0 | N/A |
| 5PI | 7.06 | 30 | 0.044 | 0.921 | 1.19 | 6.50 | 7.3 | DO control |
| 6PI | 7.25 | 30 | 0.011 | 0.902 | 0.74 | 6.38 | 6.7 | clear |
| 7PI | 7.24 | 30 | 0 | 0.855 | 0.49 | 7.40 | 7.4 | cloudy |

Table 3 shows results from lot 001 PD-X during 7 days of infection. Samples were taken daily and the run was terminated on day 7PI. pH was set at 7.25 and it was constant during run except on day 4PI when it dropped below 7.0. On day 4PI, glucose dropped to 0.4 from 0.74 the day before, glutamine started to be consumed and the titer started to go up about one log. The peak titer was observed on day 5PI when glucose was totally consumed (0.1 g/L). Also on day 5PI, DO dropped to 30% and Control was started to avoid DO drop to zero overnight. Day 6PI titer dropped and then increased to 7.4. on day 7PI. The sample was cloudy on day 7 PI.

TABLE 4

Results for lot 002PD-X run in 300 L bioreactor

| days | pH | DO % | Dextroxe g/L YSI | Lactate g/L YSI | Gln mmol/L NOVA | titer PD TCID50 | Titer QC TCID50 | comments |
|---|---|---|---|---|---|---|---|---|
| −1 | 7.27 | 116 | N/A | N/A | N/A | N/A | N/A | Added media |
| 0PI | 7.2 | 83 | 1.04 | 0 | N/A | N/A | N/A | Added cells/serum/seed |
| 1PI | 7.25 | 75 | 1.01 | 0.073 | 1.64 | 3.88 | n/a | N/A |
| 2PI | 7.25 | 74 | 0.954 | 0.105 | 1.73 | 5.5 | n/a | N/A |
| 3PI | 7.24 | 70 | 0.762 | 0.223 | 1.41 | 5.93 | 6 | N/A |
| 4PI | 7.19 | 60 | 0.409 | 0.561 | 1.25 | 6.62 | 6.5 | N/A |

TABLE 4-continued Results for lot 002PD-X run in 300 L bioreactor

| days | pH | DO % | Dextroxe g/L YSI | Lactate g/L YSI | Gln mmol/L NOVA | titer PD TCID50 | Titer QC TCID50 | comments |
|---|---|---|---|---|---|---|---|---|
| 5PI | 7.21 | 30 | 0.005 | 0.881 | 0.9 | 6.79 | 7.5 | HARVEST-I |
| R0PI (refed) | 7.24 | 116 | 0.001 | 0.858 | 0.64 | N/A | N/A | DO probe failed |
| R1PI | 6.99 | 116 | 0.247 | 0.726 | 1.38 | 7.13 | 7.5 | N/A |
| R2PI | 7.15 | 116 | 0.0 | 0.894 | 0.95 | 7.06 | 7.0 | dextrose was zero |
| R3PI | 7.13 | 116 | 0.0 | 0.865 | 0.66 | 6.69 | 7.5 | clear |
| R4PI | 7.13 | 116 | 0.0 | 0.819 | 0.21 | 7.52 | 7.5 | clear |
| R5PI | 7.13 | 116 | 0.0 | N/A | 0.1 | 7 | 7.3 | Some cloudiness |

Table 4 shows results from lot 002PD-X(R0P1 is the point at which the culture is re-fed). Based on titer results from lot 001 PD-X, harvest day was set at day 5PI. Lot 002PD-X days 1 PI through 5 PI were consistent with lot 001 PD-X. The bioreactor was harvested and then re-fed on day 5 PI. The growth curve for harvest-II was established. Samples were taken on daily basis for 5 days. Dextrose was completely consumed by day R2PI. Titer was at peak for 5 days (0.5 logs variation is within the assay error). Glutamine was totally consumed by day R5PI. The DO probe failed after re-feed. The DO level couldn't be measured (most likely close to zero). On day R4PI cells were still attached, since sample in bottle was clear. On day R5PI, some cloudiness was observed on the sample bottle indicating that cells might have started to come off springs.

basis. Dextrose was consumed completely by day 2R2PI. The titer was at peak for 4 days and then dropped to 7.0 for 2 days (0.5 logs variation was within the assay error), then dropped to 6.2 on day 7PI. Glutamine was totally consumed by day 2R5PI. DO was taken out of Control on day 2R2PI to monitor cell death.

Harvest-I Phase for Virus Propagation in the 300 L Scale:

The growth curve for Harvest-I (lot 001 PD-X) showed that viral particles continued growing till day 7PI despite of dextrose being completely consumed (0.1 g/l) by day 5 PI. Glutamine consumption started when dextrose was about half of the initial concentration of 1 g/L (day 4PI), and then after dextrose was consumed, glutamine seemed to be the primary source of energy. The inconsistency in the gluta-

TABLE 5

Results for lot 003PD-X run in 300 l bioreactor

| days | pH | DO % | Dextrose g/L YSI | Lactate g/L YSI | Glutamine mmol/L NOVA | Titer PD TCID50 | Titer QC TCID50 | comments |
|---|---|---|---|---|---|---|---|---|
| 0PI | 7.49 | 78 | N/A | N/A | N/A | N/A | N/A | N/A |
| 1PI | 7.25 | 69 | 0.987 | 0.078 | 2.05 | 4.38 | 4.7 | DO monitor/pH control |
| 2PI | 7.23 | 66 | 0.935 | 0.107 | 1.9 | 5.13 | 5.7 | N/A |
| 3PI | 7.22 | 60 | 0.783 | 0.221 | 1.71 | 6.2 | 6.5 | N/A |
| 4PI | 7.29 | 53 | 0.453 | 0.519 | 1.45 | 6.36 | 6.6 | N/A |
| 5PI | 7.1 | 30 | 0.049 | 0.899 | 1.17 | 6.36 | 7.0 | HARVEST-I |
| 0PI (refeed) | 7.19 | 71 | N/A | N/A | N/A | N/A | N/A | DO Monitor |
| R1PI | 6.98 | 18 | 0.305 | 0.702 | 2.69 | 7.26 | 7.3 | N/A |
| R2PI | 7.23 | 7 | 0.0 | 0.917 | 1.82 | 6.85 | 7.5 | HARVEST-II |
| 0PI 2$^{nd}$ refeed | 7.21 | 74 | N/A | N/A | N/A | N/A | N/A | N/A |
| 2R1PI | 6.91 | 13 | 0.097 | 0.853 | 1.69 | 7.0 | 7.5 | DO control at 10% |
| 2R2PI | 7.19 | 3 | 0.0 | 0.883 | 0.82 | 7.2 | 7.3 | DO Monitor |
| 2R3PI | 7.17 | 2 | N/A | N/A | 0.42 | 7.46 | 7.5 | cloudy |
| 2R4PI | 7.24 | 18 | N/A | N/A | 0.22 | 7.0 | 7.5 | DO is going up |
| 2R5PI | 7.24 | 47 | N/A | N/A | 0.13 | 6.68 | 7.0 | cloudy |
| 2R6PI | 7.22 | 62 | N/A | N/A | 0.06 | 6.5 | 7.0 | cloudy |
| 2R7PI | 7.24 | 68 | N/A | N/A | 0.04 | 6.36 | 6.2 | cloudy |

Table 5 shows results from lot 003PD-X. Based on titer results from lot 002PD-X, Harvest-II day was set at day 1 PI or 2PI. It was decided to harvest fluids on day 2PI to give flexibility for Production. A growth curve for Harvest-III was established for 7 days. Samples were taken on daily basis.

mine readings for the first 2-3 days could be attributed to fluctuations in the NOVA instrument since the medium only contains 2 mmol/L. The DO levels were consistently declining during the dextrose/glutamine metabolism and the virus propagation.

The virus propagation kinetics suggested harvesting the virus 5-7 days PI. The variation in QC titers between day 4 PI and 7 PI were within the variation of the assay (±0.71 logs/ml). The Harvest-I criterion was the time when dextrose was completely consumed (0.1 g/l) which was consistent with 30 L data (Study#6127-1310-09K-198). Therefore, the offline measurements of dextrose starting from day 4 PI would be necessary to track the dextrose levels. Table 3 showed that PRRSV 94881 virus was stable for 3 days (5-7 days PI) in the 300 L bioreactor after dextrose was depleted. However, if a second harvest is to be performed, based on results from table 4 and 5, it is recommended that Harvest-I be performed on the first day dextrose concentration is <0.1 g/L (using YSI measurement) to ensure cells' adherence to the springs (carriers) in the bioreactor.

Harvest-II Phase for Virus Propagation in the 300 L Scale:

For Lot 002PD-X and 003PD-X, after Harvest-I was performed on day 5PI, Fresh medium and 5% serum were added to generate the second harvest viral fluids (Tables 4 and 5). The MEM Medium (270-280 L) with IFBS (5% v/v) were added to the bioreactor following the same procedures as stated for setting up the first harvest material. A growth curve for harvest-II was conducted for 5 days on lot 002PD-X and the peak titer was achieved on day 1 days post re-feed (See Table 4). The titer was stable for 4 days. The virus titer at day 1 post-refeed was comparable to the titer of the first harvest Table 2). Dextrose level was completely consumed on day 2 PI. A range of four days post-refeed could be used for the second harvest criterion. However, performing the second harvest on day 4PI could have an effect on the third harvest since some cloudiness was observed on fluid samples that were taken on day 4 PI indicating cell death or detachment from springs. So for lot 003PD-X harvest-II was performed on day 2PI. Based on data from lot 003PD-X it is recommended that Harvest II target days be 1-2PI if a second reefed and a third harvest is going to be performed.

Harvest-III Phase for Virus Propagation in the 300 L Scale:

For lot 003PD-X (Table 5) after Harvest II that was performed on day 2PI, additional medium and serum was added to the vessel for generation of third harvest viral fluids (Table 5). The MEM Media (270-280 L) with IFBS (5% v/v) were added to the bioreactor following the same procedures as stated for setting up the first harvest material. A growth curve for harvest-III was conducted for 7 days and the peak titer was achieved on day 1 post re-feed (See Table 5). The titer was stable for 4 days. The virus titer at day 1 post-refeed was comparable to the titer of the second harvest (Tables 4 and 5). Dextrose was completely consumed on day 1 PI. A range of four days post-refeed could be used for the third harvest criterion.

The three graphics below represent the dextrose, glutamine and DO profiles, and the titers for the three runs performed in the 300 L bioreactor. The purpose of the graphics is to show the consistency of the three runs.

Figure 3:
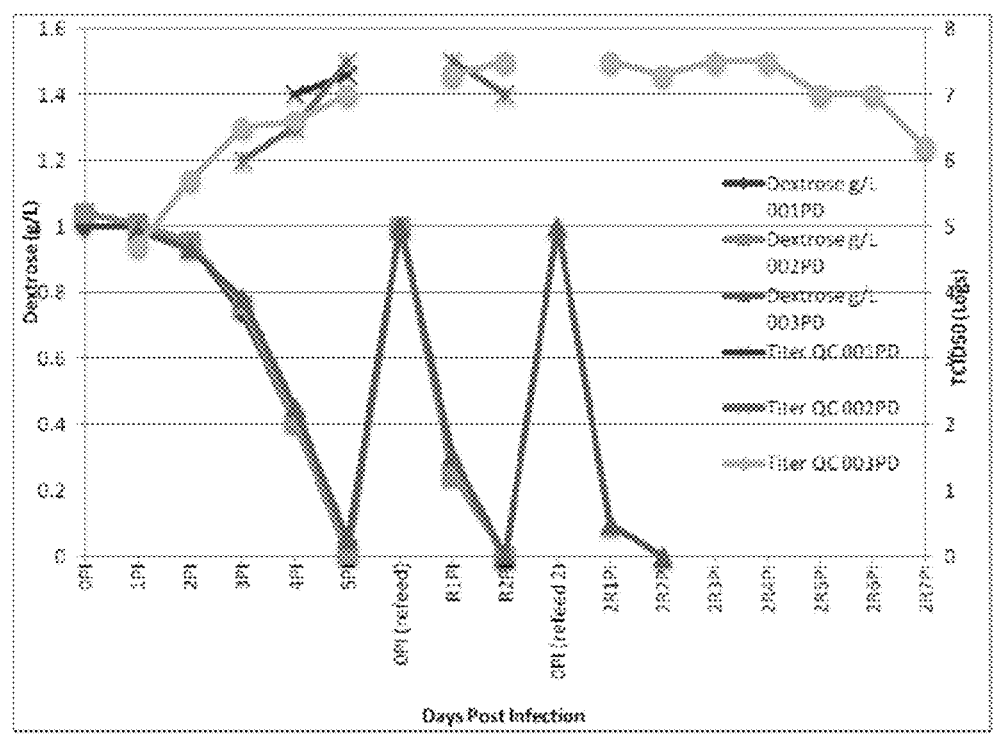

FIG. 3 shows a summary of all three runs performed in the 300 L scale for dextrose consumption and virus titers. Harvest-I profile for the three runs were very consistent, dextrose was totally consumed (0.1 g/l) by day 5PI and it coincided with peak titer on the three runs performed. After the first reefed, dextrose was below 0.3 g/l for lots 002PD and 003PD on day 1 PI and the titer was already at peak. On day 2PI, dextrose was completely consumed and virus titer stayed at peak. For harvest III in lot 003PD, when second reefed was performed on day R2PI, dextrose was down to less than 0.1 g/L by day 2R1PI and the titer was at peak.

Figure 4:
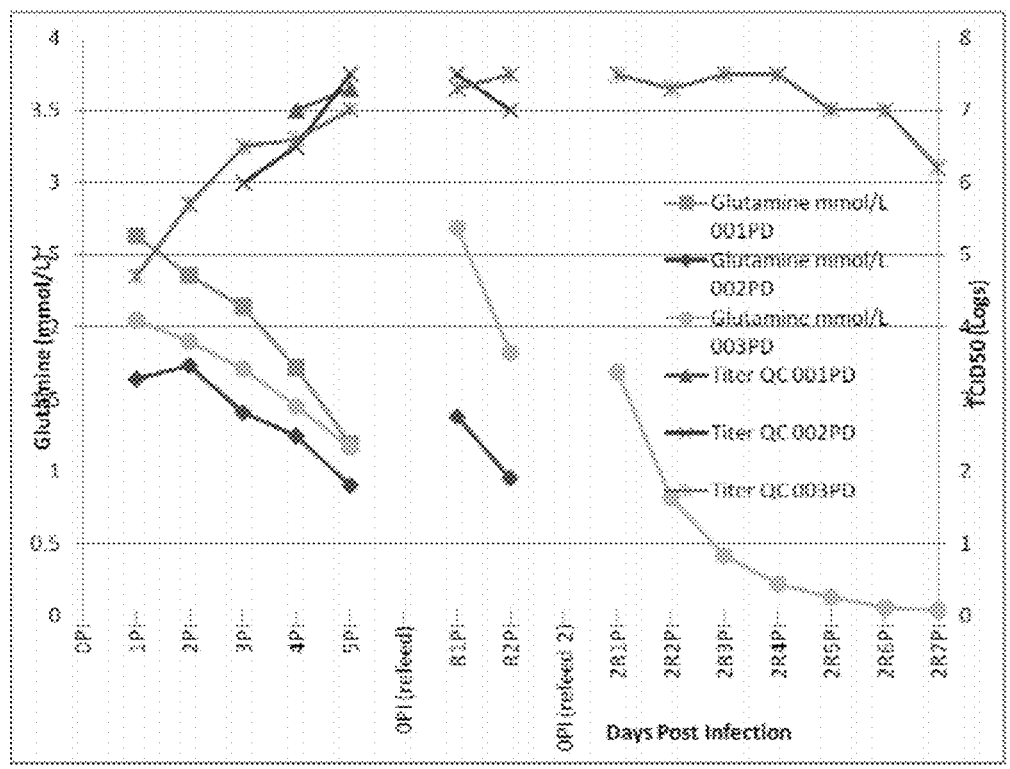
FIG. 4: Viral titers and glutamine profiles for the three concurrent runs in the 300 L Bioreactors.
Figure 5:
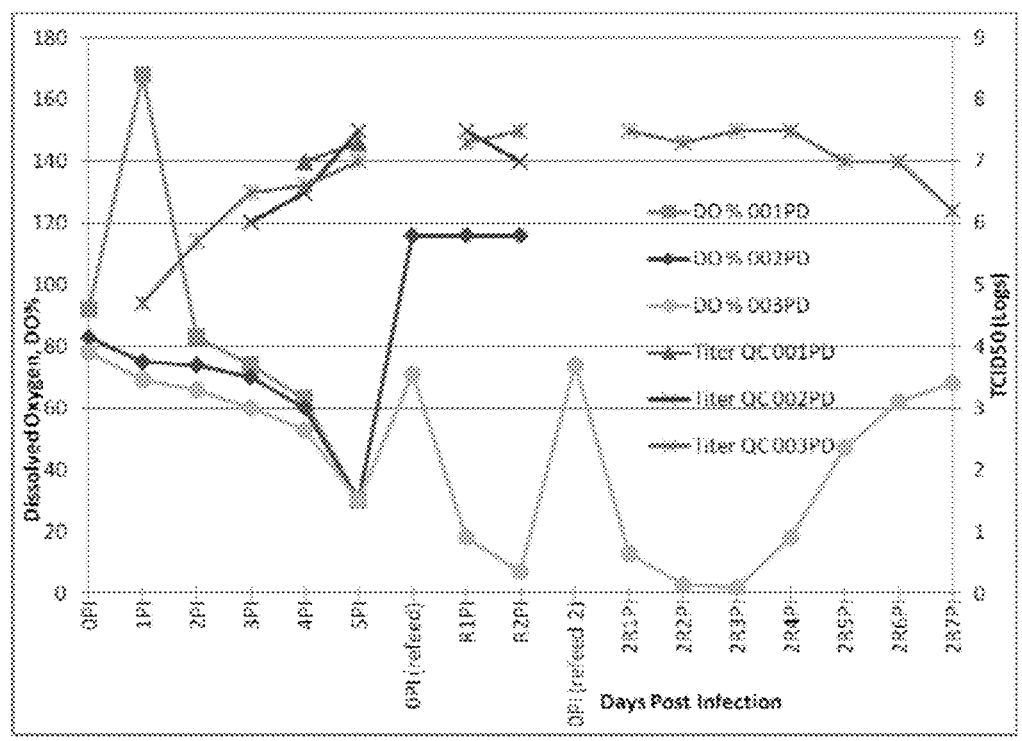
FIG. 5: Viral titers and DO profiles for the three concurrent runs in the 300 L Bioreactors.

FIG. 4 shows a summary of all three runs performed in the 300 L scale for glutamine consumption and virus titers. As can be seen for harvest-I profile for the three runs were very consistent. Glutamine droped to half its initial concentration of 2 mmol/L by day 5PI and it coincided with peak titer on the three runs performed. After the first re-feed, glutamine dropped to half of its initial concentration by day 2 PI for lots 002PD and 003PD and titer was already at peak since day 1 PI. For harvest III in lot 003PD, when second re-feed was performed on day R2PI. Glutamine was slowly being consumed to 0 by day 5 PI and virus titer was consistent, then cells started to die and titer dropped by day 7PI.

As can be seen for harvest-I profile, the three runs were very consistent, DO down to 30% by day 5 PI and it coincided with the peak titers on the three runs performed. After first re-feed, DO probe failed for lot 002PD-X, so data is not available, on lot 003PD-X DO dropped on day 1 PI, coinciding with peak titer. For harvest-III in lot 003PD, when second re-feed was performed on day R2PI DO was rapidly decreasing until day 3 PI when cells started to die and DO was consumed to 0 by day 5 PI and virus titer was consistent, then cells started to die and titer dropped by day 7PI.

TABLE 6

Summary of the conditions and results of concurrent process in 300 L bioreactor runs*.

| Lot | PCD | MOI | TOH1 | Titer H1 | TOH2 | Titer H2 | TOH3 | Titer H3 |
|---|---|---|---|---|---|---|---|---|
| 001PD-X | $7.0 \times 10^9$ | 0.1 | 5 | 7.3 | N/A | N/A | N/A | N/A |
| 002PD-X | $7.0 \times 10^9$ | 0.1 | 5 | 7.5 | 1-4 | 7.5 | N/A | N/A |
| 003PD-X | $7.0 \times 10^9$ | 0.1 | 5 | 7.0 | 2 | 7.5 | 1-4 | 7.5 |

*Target conditions (0.1MOI, $7.0 \times 10^9$ total cells per 300 L bioreactor, pH 7.25, and 36° C.)
(H1): Denotes the first harvests in days post infection.
(H2): Denotes the second harvest in days post infection.
(H3): Denotes the third harvest in days post infection.

The viral fluids from Lot 001 PD-X were bleached and discarded. One liter from Lot 002PD-X harvest-I was kept and SGS added (25% v/v) for research purposes, the rest of fluids were bleached and discarded. Two liters from lot 003PD-X Harvest II were kept frozen for concentration purposes, the rest of fluids were bleached and discarded Range of Planting Cell Density (PCD) for 300 L Scale:

The target planting cell density (PCD) is $7.0 \times 10^9$ total cells per 300 L bioreactor with a working volume of 270-280 L. Based on the data from 30 L Final Process Transfer Report (6127-1310-09K-198), the total cell planting range is between $7.0 \times 10^8$-$1.0 \times 10^9$ per 30-L bioreactor. Due to time constraints only target cell planting density was evaluated.

Range of the Multiplicity of Infection (MOI) for 300 L Scale:

The target MOI of 0.1 is ideal for propagation of PRRSV 94881 within this growth system. Low and high MOI level of 0.01 and 0.3, respectively, were examined in the 30 L bioreactors.

Risk Analysis:

The recommended 300 L bioreactor concurrent process parameters are outlined in Table 11. Only target parameters were tested and considered for whether they were critical or non-critical to the process. Ranges were evaluated at the 30 L scale. The definitions are as follows:

- Critical parameters are those parameters that are critical to quality attributes of the final product;
- Non critical parameters are those parameters that can either be controlled directly within the defined range or have a wide operational range so a deviation from the set-point is non-critical. Non-critical parameters aid in controlling the critical parameters within the defined range
- "For Information Only" parameters are parameters that are monitored to gain additional information about the process, but have no direct correlation to the attributes of the final product.

MA104 cells were planted at a density of $7 \times 10^9$/300 L spring bioreactor in 270-280 L of media supplemented with 14.0 L of Fetal Bovine Serum 5% v/v (range: $7 \times 10^9$-$1 \times 10^{10}$/300 L spring bioreactor). The temperature of the bioreactor was controlled at 36±1° C. DO is set at "Monitor Mode". Activate DO Control at Set Point of 10% once DO level drops to 10-30%. pH 7.2 is set at Control Mode. PID parameters used for pH High ($CO_2$ addition) were:

| | |
|---|---|
| Gain | 300.00 |
| Reset mins per repeat | 2.20 |
| Rate, minutes | 0.50 |
| Fine valve spam pH units | 0.03 |
| Fine valve CV limit | 5% |

The air flow flow rate is set at 2.0 SLPM; the $CO_2$ flow rate at 2.0 SLPM; the $O_2$ flow rate at 2.0 SLPM; the N2 flow rate set at 2.0 SLPM and total gas sparge rate should be at 2.0 SLPM.

The target MOI is 0.1 (range $7 \times 10^8$-$1 \times 10^9$ virus particles/ 300 L spring bioreactor).

For harvest-I criterion, the offline sampling of dextrose measurements are taken starting on day 4 PI. DO trend could

TABLE 7

Summary of 300 L bioreactor Concurrent Process parameters for PRRSV 94881 MLV

| Parameter | *Lower Limit Tested | *Upper Limit Tested | *Accepted Range | Accepted Target | Critical/Non-Critical |
|---|---|---|---|---|---|
| MOI | 0.01 | n/a | 0.01-0.30 | 0.10 | NC* |
| Cell Planting Density | $7.0 \times 10^9$ cells | $1.0 \times 10^{10}$ cells # | $7.0 \times 10^8$ cells to $10 \times 10^9$ cells | $7.0 \times 10^9$ cells | NC* |
| Time of 1$^{st}$ Harvest (Days post infection) | Day 4 | Day 7 | Day 5-Day 7 PI | Day 5-7 PI | Critical** |
| Temperature | 35° C. | 38° C. | 36 ± 1° C. | 36° C. | NC* |
| pH | 6.5 | 7.9 | 6.9-7.9 | 7.2 | NC* |
| Time of 2$^{nd}$ Harvest (Days post re-feed) | Day 1 | Day 5 | Day 1-Day 4 | 1-2 | Critical*** |
| Time of 3$^{rd}$ Harvest (Days post re-feed) | Day 1 | Day 7 | Day 1-Day 4 | 1-4 | Critical |

*Non critical within the examined range at the 30 L scale.
**First-Harvest criterion is decided by the time of the complete consumption of dextrose within the period of 5-7 days PI. However if a second harvest is to be performed Harvest-I should be on the first day dextrose is 0.1 g/L
***Fluids are stable for 5 days. However if a third harvest is to be performed harvest should be between days 1 and 2
Based on 30 L data for scale-up Conclusions and Process Recommendations:

The concurrent process scale up from 30 L to 300 L bioreactor was successfully achieved. Harvest-I was within the range of 30 L bioreactor for days of harvest and titer. Harvest-II was also successful with titers comparable of Harvest-I. The titer of the 2nd harvest was stable for 4 days. An additional (third) harvest was achieved with titers comparable to harvest-I and II. The titer of the third harvest was stable for at least 4 days.

The recommendations for a preferred 300 L bioreactor concurrent process for PRRSV 94881 MLV are as follows:

Virus Propagation, HARVEST-I:

The media composition was MEM without Phenol Red, 30 mg/L Neomycin and 1.4 g/L Sodium bicarbonate.

be used as indicator. Harvest-I should be performed when dextrose is ≤1 g/L (range 2 days+/−) which usually occurs between 5-7 days PI. However if a second harvest is to be performed Harvest-I is recommended on the first day dextrose concentration is ≤1 g/L.

First Re-Feed—HARVEST-II: After the first Harvest, re-feed the bioreactor with 270-280 L of media composition MEM without Phenol Red, Neomycin and 1.4 g/L Sodium bicarbonate supplemented with 14.0 L of Fetal Bovine Serum (5% v/v). The re-feed is performed under same conditions as the first harvest media set-up (see First Harvest parameters above). pH control is to remain at a set point of 7.2. PID parameters used for pH High (CO2 addition) were:

| | |
|---|---|
| Gain | 300.00 |
| Reset mins per repeat | 2.20 |
| Rate, minutes | 0.50 |
| Fine valve spam pH units | 0.03 |
| Fine valve CV limit | 5% |

Temperature control remains on at a set point of 36±1° C. DO control is set at Monitor Mode.

Second Re-Feed—HARVEST-III: Immediately after the second harvest, re-feed the bioreactor with 270-280 L of media composition MEM without Phenol Red, Neomycin and 1.4 g/L Sodium bicarbonate supplemented with 1.40 L of Irradiated Fetal Bovine Serum (5% v/v). The re-feed is performed under same conditions as the first harvest media set-up (see second harvest parameters above). pH control is to remain at a set point of 7.2. PID parameters used for pH High ($CO_2$ addition) were:

| | |
|---|---|
| Gain | 300.00 |
| Reset mins per repeat | 2.20 |
| Rate, minutes | 0.50 |
| Fine valve spam pH units | 0.03 |
| Fine valve CV limit | 5% |

Temperature control is to remain on at a set point of 36±1° C. DO is set at Monitor Mode. Current test results show that the optimal time is between days 1-4 post re-feed for third Harvest viral fluids.

It should be understood that the above process is exemplary and may be further modified to increase yield and/or decrease costs of running the bioprocessor. For example, changes in parameters may include, but are not limited to: Reducing the serum concentration for second and third harvests, reducing cell planting density, adding cells and seed in the same bottle and let it stir, so virus propagation can be shorten for harvest I. Also, the virus yield may be further improved by one more re-feed for a possible Harvest IV. Feeding spent media components, such as, but not limited to, glucose and glutamine

EXAMPLE 2

In a specific example the PRRSV 94881 produced according to the method described above was used to determine the efficacy of the PRRSV 94881 in vaccinating pigs. In this study, Piglets from 4 to 13 days old were vaccinated intramuscularly with a composition comprising $10^{7.6}$ TCID 50 in 2 ml (day 0 of study). At day 13, the piglets were weaned and were monitored for various disease parameters through to day 90. Study parameters included monitoring viremia, presence of virus in tissues and secretions, clinical observations, lung lesions and weight gain.

Each of the study groups: the vaccinates, the sentinels and the controls were weighed on study day 0, 14, 28, 56 and 90. Blood was sampled every alternate day between days 0 and 14 and once a week to day 90 for both the vaccinated group and the sentinels and once a week throughout the study periods for the controls up to day 90.

Nasal, oral and faecal swabs were taken every alternate day between days 0 and 14 and once a week to day 56 for both the vaccinated group and the sentinels and once a week throughout the study periods for the controls up to day 56.

Necropsy was assessed in the vaccinated group in two pigs every other day from Day 0 to 14 and one a week day 14 to day 90 with remaining pigs at day 90. In the sentinel group 5 pigs at day 56 with remaining at Day 90. Control group 2 pigs every other day between Day 0 to day 14, once a week between day 14 and day 56 and remaining pigs at day 90.

Clinical observations were taken every day.

Quantitative RT-PCR was performed using PRRSV European specific primers for samples form blood, oral, faecal, and nasal swab, as well as lung lavages.

From these studies data showed that the piglets showed normal health except for a few pigs that were lame. Post-mortem there were no abnormalities at necropsy except that 1-2 animal showed signs of mildly enlarged inguinal lymph notes. Importantly, it was seen that there were no lung lesions observed with the vaccinated group.

Figure 6:
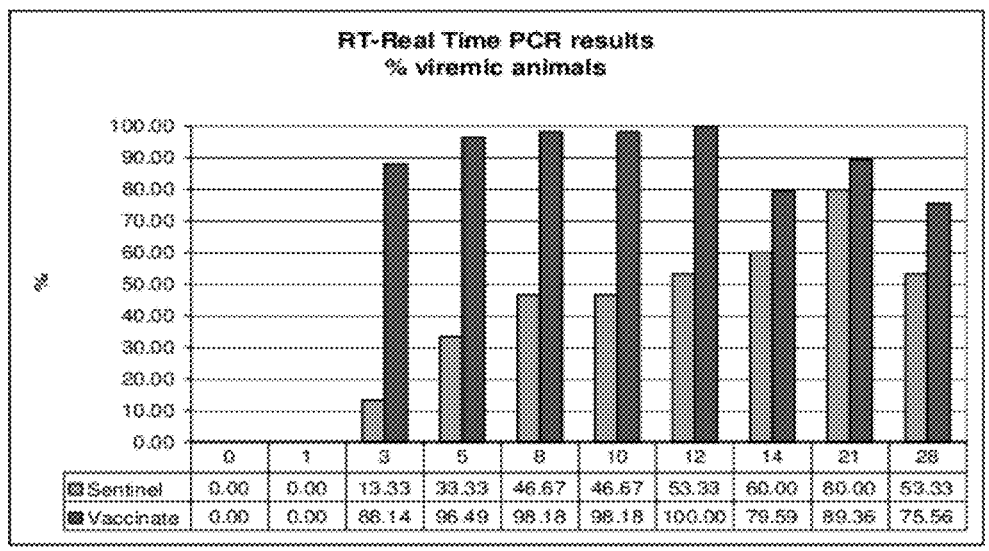
FIG. 6: Shows RT-PCT Time PCR results depicting % viremia in animals vaccinated with PRRSV 94881.

FIG. 6 shows the percentage of viremic animals in the sentinel group as compared to the group vaccinated with a composition containing the attenuated PRRS virus strain deposited at ECACC Accession No. 11012502 showing efficacy of the PRRS virus produced according to the methods of the invention in providing protective immunity to pigs.

EXAMPLE 3

The following equipment and reagents (Table 8) were used in the development of the concurrent roller bottle process for EU PRRS 94881:

TABLE 8

| Equipment | | |
|---|---|---|
| Process Step | Procedure | Equipment |
| MA104 (passages 58-78) and AK-MA104 (passages 64-84) cell maintenance. Same cell line, different passages | Maintenance and scale-up, according to process records BPF-777 and BPF-778 | 850 $cm^2$ Roller Bottles (CORNING) |
| Cell count | Automated count | Vi-Cell |
| Cell Culture Virus Production | Cell growth Infection | 850 $cm^2$ Roller Bottles (CORNING) Roller rack and incubator |
| | Dextrose/Lactate Conc. g/L (±5% assay variation) | YSI 2700 |
| | Sampling | pipettes |

MEM with Phenol Red medium and 1.4 g/L Sodium Bicarbonate was obtained from SAFC. Table 9 describes the Medium composition, plus serum concentration. This medium was used to propagate the virus including all roller bottle re-feeds.

TABLE 9

| MEM Media Composition. | | | |
|---|---|---|---|
| Catalog/Item # | Component | Lot number | Quantity per roller bottle |
| 700754 | Fetal Bovine Serum Gamma irradiated, US | 10D837 | 20 mL (5% v/v) |
| 62892-1000M3056 | MEM with Phenol Red | 10L259 | 400 mL |

Figure 7:
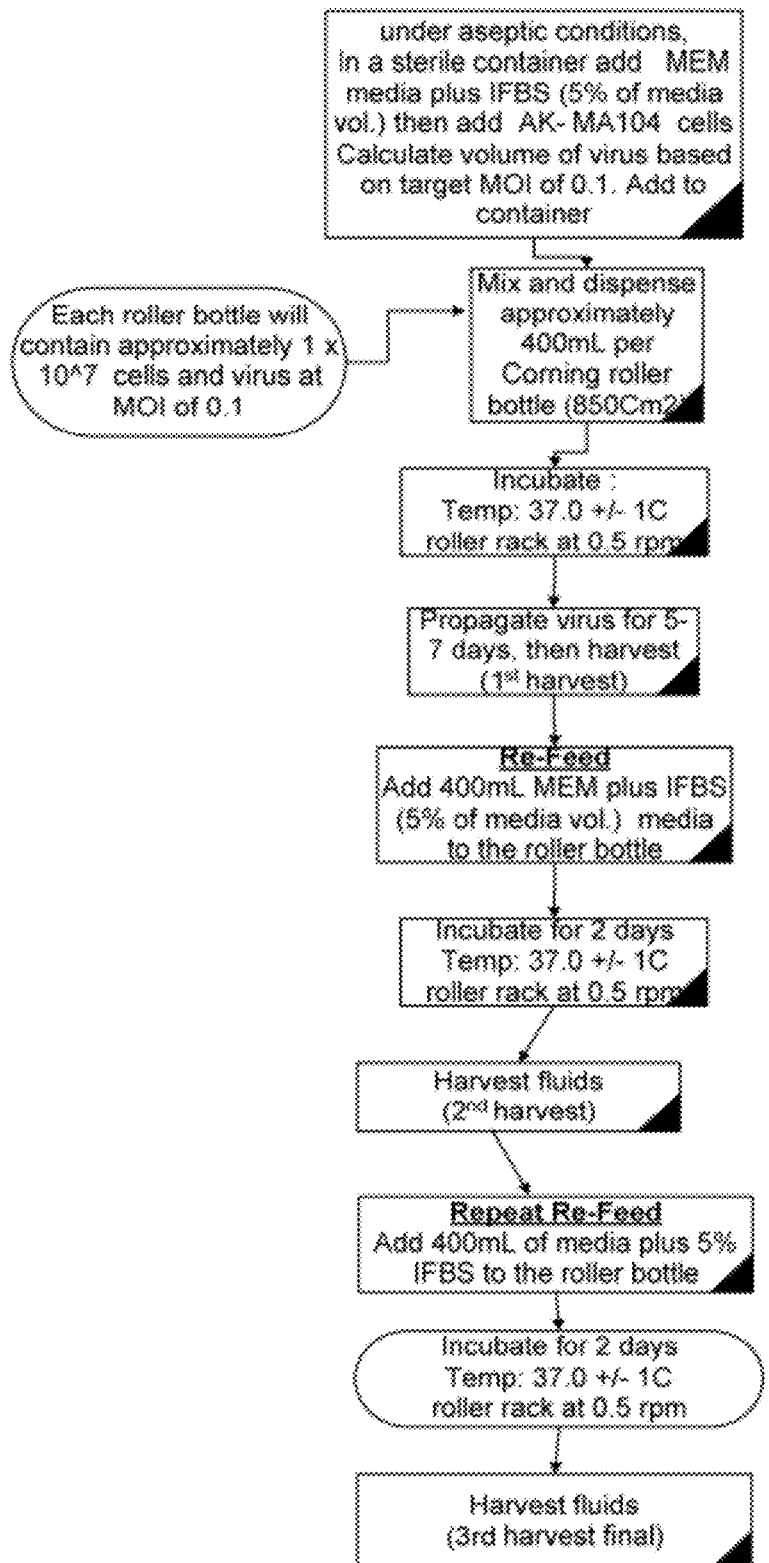
FIG. 7: Concurrent process for roller bottle production of PRRSV 94881.

Concurrent Process with Three Harvests:

The concurrent process added media with serum, AK-MA104 cells and EU PRRS 94881 virus seed in a container. Then, the contents of the container were mixed and dispensed into the roller bottles (TOI equals zero days PP). FIG. 7 illustrates the concurrent process method and FIG. 8 illustrates the process definition and timelines.

Roller Bottle and Media Preparation:

The experiment presented here was a batch of 5 roller bottles. Actual batch size may vary.

Under aseptic conditions, 2000 mL of MEM media and 100 mL of Irradiated Fetal Bovine Serum were added to a container. Then $5\times10^7$ AK-MA104 cells and EU PRRS virus seed at a MOI of 0.1 were added. These materials were mixed and under aseptic conditions, An approximately 400 mL per 850 cm2 Corning roller bottle was dispensed. The roller bottles were then incubated at 37° C. in a roller rack at a speed of 0.5 rpm. Up to three harvests were performed with two media re-feeds.

Criteria for Harvest and Acceptable Potency:

The criteria for harvest the roller bottles was based on the set point/target for the critical parameters from the validated 300 L bioreactor process of Examples 1 and 2, as shown in Table 10 below.

Harvest-I was performed on days 5-7 PI and dextrose levels 0.1 g/L. Harvest II occurred on day 2PI after re-feed and Harvest III on day 2PI after second re-feed.

The potency of all three roller bottle harvests should be $\geq10^{5.5}$ $TCID_{50}$/mL.

TABLE 10

Harvest Criteria/acceptable potency for EU PRRS 94881 MLV

| Parameter | Acceptable Target |
|---|---|
| Time of 1st Harvest (Days post infection) | Day 5-7 PI |
| Dextrose level at 1st harvest | ≤0.1 g/L |
| Time of 2nd Harvest (Days post re-feed) | 2 |
| Time of 3rd Harvest (Days post re-feed) | 2 |
| Potency | $\geq10^{5.5}$ $TCID_{50}$/mL |

*Critical parameters are those parameters that are critical to quality attributes of the final product Roller Bottle Runs

TABLE 11

Initial experiment for the development of the EU PRRS 94881 concurrent roller bottle process and titer results

| Roller bottle code | Cell planting density per RB | MOI | H-I + refeed | Dextrose g/L | $TCID_{50}$ per mL | H-II + refeed | $TCID_{50}$ per mL | H-III final | $TCID_{50}$ per mL |
|---|---|---|---|---|---|---|---|---|---|
| A | $3.5\times10^6$ | 0.1 | 5PI | 0.304 | ≤5.5 | 7PI | 6.5 | 9PI | ≤6.0 |
| B | $3.5\times10^6$ | 0.1 | 6PI | 0.048 | 6.5 | 8PI | 6.6 | 10PI | ≤5.7 |
| C | $3.5\times10^6$ | 0.1 | 7PI | 0.006 | ≤5.5 | 9PI | ≤6.3 | 11PI | 6.7 |
| D | $3.5\times10^6$ | 0.005 | 5PI | N/A | ≤5.6 | 7PI | 6.5 | 9PI | ≤5.5 |
| E | $3.5\times10^6$ | 0.005 | 6PI | 0.057 | ≤5.5 | 8PI | ≤5.5 | 10PI | 7.4 |
| F | $3.5\times10^6$ | 0.005 | 7PI | 0.0 | ≤5.5 | 9PI | ≤5.5 | 11PI | ≤5.5 |
| G | $7\times10^6$ | 0.1 | 5PI | 0.066 | 6.6 | 7PI | 6.9 | 9PI | ≤6.3 |
| H | $7\times10^6$ | 0.1 | 6PI | 0.009 | 6.5 | 8PI | 7.3 | 10PI | 6.7 |
| I | $7\times10^6$ | 0.1 | 7PI | 0 | ≤6.2 | 9PI | 7.0 | 11PI | 6.6 |
| J | $1\times10^7$ | 0.1 | 5PI | 0.095 | 6.9 | 7PI | 6.6 | 9PI/10PI | ≤6.3/6.7 |
| K | $1\times10^7$ | 0.1 | 6PI | 0 | 7.3 | 8PI | 7.5 | 10PI/11PI | 6.5/6.6 |
| L | $1\times10^7$ | 0.1 | 7PI | 0 | 7.7 | 9PI | ≤5.5 | 11PI/12PI | 7.2/6.6 |
| M | $1\times10^7$ | 0.005 | 5PI | 0.118 | ≤5.6 | 7PI | 7.5 | 9PI | ≤6.0 |
| N | $1\times10^7$ | 0.005 | 6PI | 0.014 | 7.0 | 8PI | 6.7 | 10PI | 6.7 |
| O | $1\times10^7$ | 0.005 | 7PI | 0 | 6.7 | 9PI | 7.3 | 11PI | 6.7 |

Control experiment: Roller bottle conventional process for EU PRRS 94881

| Roller bottle code | Cell planting density | TOI | MOI | Harvest I + refeed | $TCID_{50}$ per mL | Harvest II + refeed | $TCID_{50}$ per mL | Harvest III final | $TCID_{50}$ per mL |
|---|---|---|---|---|---|---|---|---|---|
| P | $2\times10^7$ | 3 days | 0.005 | 3PI | 6.7 | 6PI | 7.4 | 9PI | 6.9 |
| Q | $2\times10^7$ | 3 days | 0.005 | 4PI | 6.7 | 7PI | 7.7 | 10PI | 6.7 |
| R | $2\times10^7$ | 3 days | 0.005 | 5PI | 7.0 | 8PI | 7.2 | 11PI | 6.6 |
| S | $2\times10^7$ | After 3 days, cells were counted for MOI calculation for RBs P, Q and R | | | | | | | |

Table 11 shows the initial experiment designed to define the concurrent roller bottle process based on the following parameters from the process described in Examples 1 and 2 and working seed virus reports showed on Table 12a.

TABLE 12a

Parameters evaluated to define concurrent roller bottle process

| parameters | range | information |
|---|---|---|
| Cell planting density per 850 $cm^2$ RB | $3.5\times10^6$ | low cell planting range |
| | $7.0\times10^6$ | Middle cell planting range |
| | $1.0\times10^7$ | Equivalent to 300 L BR based on cells/mL |
| MOI | 0.005 | RB conventional process |
| | 0.1 | Target MOI for 300 L BR process |

Fifteen roller bottles were planted with MA-104 cells at cell planting densities that ranged from $3.5\times10^6$ to $1\times10^7$ (see Table 11 column 2). The roller bottles were labeled in alphabetical order. Sets of three roller bottles had the same cell planting density and same MOI that ranged from 0.005 to 0.1 (Table 11, third column).

Three cell planting densities and two MOIs were evaluated (Table 12). Sets of three roller bottles had same cell planting density and same MOI (Table 4 column 1). Roller bottles were set up according to roller bottle and media preparation described above and incubated in a roller rack at a speed of 0.5 RPM at 37° C. walk in incubator.

Roller bottles A, D, G, J and M harvest I occurred on day 5PI, and then they were re-fed and incubated for two days.

H-II was then performed, roller bottles were re-fed and incubated and a third and final harvest was performed two days later.

Roller bottles B, E, H, K and N H-I occurred on day 6PI, and then they were re-fed and incubated for two days. H-II was then performed; roller bottles were re-fed one more time and re-incubated. A third and final harvest was performed two days later.

Finally, roller bottles C, F, I, L and O H-I occurred on day 7PI, and then they were re-fed and incubated for two days. H-II was then performed, roller bottles were re-fed and re-incubated and a third and final harvest was performed two days later.

The roller bottle conventional process (roller bottles P, Q, R and S) was utilized as a control for this experiment. This process was developed with two harvests. The third harvest was added to the process in these experiments as well as the harvest-I range up to 5 daysPI.

MA104 cells were planted on 850 cm² roller bottles at 2×10⁷ and incubated for 3 days (roller bottles P, Q, R and S). After three days, roller bottle S was trypsinized and cells were counted by Vi-cell. Cell count was used for virus MOI calculation for RB's P, Q and R. Calculated amount of virus were added to roller bottles that are incubated, at 37° C. in a roller rack. After 3 days harvest-I is performed on roller bottle P, which was then re-fed and incubated at 37 C. After 3 days, a second harvest was obtained, and re-fed a second time, and incubated an additional 3 days for a third and final harvest.

Roller Bottles Q and R followed the same procedure after H-I, on day 4P1 for RB Q and 5PI for RB R.

The conventional roller bottle process is longer than the concurrent process described in Examples 1 and 2 and requires more labor, since cells need to grow for 3 days, before they are infected with virus. Also, it requires double cell planting density when compared with the concurrent process but lower MOI. This process yielded high consistent titers for the three harvests.

It was decided that the H-I time of harvest (TOH) for the concurrent process be based on target days only, regardless of dextrose consumption. Samples were taken for dextrose measuring and titer at harvest days.

Based on the criteria for potency acceptable titer (Table 10), Roller Bottles A, B, C, D, E and F showed inconsistent titers for harvests I, II and III.

Roller bottles G, H and I with cell planting density of 7×10^6 and target MOI of 0.1 had dextrose level at first harvest within target of ≤0.1 g/L. Titer results for roller bottles G and H were acceptable. For harvest-II, all roller bottles G, H and I had titers in the high 6 and low 7 logs. For harvest-III, roller bottles G and H were acceptable with titers of 6.6 and 6.5, respectively. For most harvests set G, H and I were acceptable.

The next set experiment J, K and L was the most promising one in terms of titers. Dextrose was consumed at H-I for all RBs and titer within acceptable criteria based on Table 10. On second and third harvests the titers also met criteria on Table 3 except for two roller bottles. H-III for RBs J, K and L were extended for one more day showing that titers were still acceptable. (Table 11)

Last roller bottles M, N and O, had high cell planting density, and low MOI showed consistent titer results for roller bottles N and O.

TABLE 12b

Comparison of parameters between the concurrent roller bottle process and the bioreactor process

| Parameter | 300 L bioreactor | Roller Bottle set J, K and L |
|---|---|---|
| Media plus serum working volume in mL | 283500 | 400 |
| Cell planting density/mL | $2.53 \times 10^4$ | $2.5 \times 10^4$ |
| MOI | 0.1 | 0.1 |

Based on Table 10, the roller bottles J, K and L TCID$_{50}$/mL results shown on Table 11, met all the criteria for harvests I, II and III. The ratio of cell planting density per mL in the roller bottles J, K and L are equivalent to the bioreactor cell planting density per mL (Table 6) for the 300 L. Based on these data, the parameters for roller bottles J, K and L were the chosen for a confirmation run (Table 13).

TABLE 13

Concurrent roller bottle process development confirmation run set up and dextrose concentration at harvest-I

| Roller bottle code | Cell planting density/RB | MOI | Harvest I + refeed | dextrose g/L at TOH | H II + refeed | H III Final |
|---|---|---|---|---|---|---|
| J1 | 1 × 10⁷ | 0.1 | 5PI | 0.080 | 7PI | 9PI |
| J2 | 1 × 10⁷ | 0.1 | 5PI | 0.128 | 7PI | 9PI |
| J3 | 1 × 10⁷ | 0.1 | 5PI | 0.066 | 7PI | 9PI |
| J4 | 1 × 10⁷ | 0.1 | 5PI | 0.076 | 7PI | 9PI |
| J5 | 1 × 10⁷ | 0.1 | 5PI | 0.128 | 7PI | 9PI |
| K1 | 1 × 10⁷ | 0.1 | 6PI | 0.137 | 8PI | 10PI |
| K2 | 1 × 10⁷ | 0.1 | 6PI | 0.058 | 8PI | 10PI |
| K3 | 1 × 10⁷ | 0.1 | 6PI | 0.100 | 8PI | 10PI |
| K4 | 1 × 10⁷ | 0.1 | 6PI | 0.088 | 8PI | 10PI |
| K5 | 1 × 10⁷ | 0.1 | 6PI | 0.087 | 8PI | 10PI |
| L1 | 1 × 10⁷ | 0.1 | 7PI | 0.005 | 9PI | 11PI |
| L2 | 1 × 10⁷ | 0.1 | 7PI | 0.006 | 9PI | 11PI |
| L3 | 1 × 10⁷ | 0.1 | 7PI | 0.0 | 9PI | 11PI |
| L4 | 1 × 10⁷ | 0.1 | 7PI | 0.013 | 9PI | 11PI |
| L5 | 1 × 10⁷ | 0.1 | 7PI | 0.004 | 9PI | 11PI |

Table 13 shows the confirmation run for the chosen concurrent process evaluated on Table 10.

A total of 15 roller bottles were set up at cell planting density of 1×10⁷ each in 400 mL of media with serum and EU PRRS 94881 MSV+4 seed at MOI of 0.1. Roller bottles were divided and 3 groups of 5. Harvest-I was performed on day 5PI for J1 to J5 RBs, on day 6PI for K1 to K5 and day 7PI for L1 to L5. Dextrose was measured for each roller bottle. Then harvests were pooled and samples were taken for titer. Subsequent re-feeds and harvests II and III final were performed.

At harvest-I, on average, all fifteen roller bottles had dextrose within harvest criteria of ≤0.1 g/L set for the bioreactor process (Table 3), which confirmed that the process is consistent in roller bottles.

TABLE 14

Summary of the conditions and $TCID_{50}$ results of concurrent roller bottle process

| Lot (pool of 5 roller bottles) | PCD | MOI | TOH1 | Dextrose g/L at TOH1 | $TCID_{50}$/mL H1 | TOH2 | $TCID_{50}$/mL H2 | TOH3 | $TCID_{50}$/mL H3 |
|---|---|---|---|---|---|---|---|---|---|
| J | $1.0 \times 10^7$ | 0.1 | 5PI | 0.092 | 6.5 | 7PI | 7.3 | 9PI | 6.5 |
| K | $1.0 \times 10^7$ | 0.1 | 6PI | 0.084 | 6.7 | 8PI | 7.6 | 10PI | 6.7 |
| L | $1.0 \times 10^7$ | 0.1 | 7PI | 0.000 | 6.5 | 9PI | 7.7 | 11PI | 7.4 |

Table 14 shows a summary of the conditions and the virus titers in $TCID_{50}$/mL for the pool of roller bottles J, K and L for H-I, H-II and H-III for the concurrent roller bottle process of the present invention.

To mimic the roller bottle process, samples from each individual roller bottle for set J (Table 13) were pooled and the pooled sample for titer. Same procedure was applied to roller bottles K and L for H-I, H-II and H-III.

Dextrose for H-1 pool samples were 0.0 g/L for J, K and L. Titers for H-I, H-II and H-III range from 6.5 to 7.7 which is comparable to the 300 L bioreactor process. (Table 15)

TABLE 15

Summary of the conditions and $TCID_{50}$/mL results of concurrent 300 L BR validated process*

| Lot | PCD | MOI | TOH1 | Dextrose g/L at TOH1 | TCID50/mL H1 | TOH2 | TCID50/ mL H2 | TOH3 | TCID50/mL H3 |
|---|---|---|---|---|---|---|---|---|---|
| 021610PD | 7.2 × 109 | 0.1 | 5PI | 0.0 | 7.5 | 7PI | 7.5 | 9PI | 6.7 |
| 030110PD | 7.2 × 109 | 0.1 | 6PI | 0.0 | 7.3 | 8PI | 7.4 | 10PI | 7.4 |
| 031510PD | 7.2 × 109 | 0.1 | 7PI | 0.0 | 7.5 | 9PI | 6.7 | 11PI | 7.4 |

*samples contain SGS as stabilizer

Table 15 shows the parameters and titers in $TCID_{50}$/mL for the three Validation runs performed under cGMP conditions. All three lots had the same planting cell density, same MOI. Dextrose was 0.0 g/L on harvest I for all three lots. All harvests had results within acceptance criteria.

Range of Planting Cell Density (PCD) for Roller Bottle:

The target planting cell density (PCD) is $1.0 \times 10^7$ total cells per roller bottle with a working volume of 400 mL. For the low range $7 \times 10^6$ was evaluated (Table 4) with acceptable titers as well. The high range was evaluated on the conventional process (Table 11).

Range of the Multiplicity of Infection (MOI) for Roller Bottle:

The target MOI of 0.1 is ideal for propagation of EU PRRS 94881 within this growth system. Low and high MOI level of 0.01 and 0.3, respectively, were examined in the 30 L bioreactors. In the roller bottle due to time constraints only target 0.1 MOI and 0.005 MOI were evaluated (Table 10).

Analysis

The recommended roller bottle concurrent process parameters are outlined in Table 16. Only target parameters were tested and considered for whether they were critical or non-critical to the process. The definitions are as follows: Critical parameters are those parameters that are critical to quality attributes of the final product and non critical parameters are those parameters that can either be controlled directly within the defined range or have a wide operational range so a deviation from the set-point is non-critical. Non-critical parameters aid in controlling the critical parameters within the defined range

TABLE 16

Summary of Concurrent roller bottle Process parameters for EU PRRS 94881 MLV.

| Parameter | Lower Limit Tested | Upper Limit Tested | Acceptable Range | Target | Critical/ No n-Critical |
|---|---|---|---|---|---|
| MOI | 0.005 | 0.1@ | 0.005-0.3& | 0.10 | NC |
| Cell Planting Density per Roller Bottle | 7 × 106 cells | 2.0 × 107 cells # | 7.0 × 106 cells to 2.0 × 107 cells | 1.0 × 107 cells | NC |
| Time of 1st Harvest (Days post infection) | Day 5 | Day 7 | Day 5-Day 7 PI | Day 5-7 PI | Critical** |
| Temperature | NT | 37° C. | 36 + 1° C. | 36° C. | NC |
| Time of 2nd Harvest (Days post re-feed) | Day 2 | Day 2 | NT | 2 | Critical |
| Time of 3rd Harvest (Days post re-feed) | Day 2 | Day 2 | 2-3 | 2 | Critical |

**First-Harvest criterion is decided by the time of the complete consumption of dextrose within the period of 5-7 days PI.
based on conventional roller bottle process
@tested at 30 L, 300 L bioreactor scale and roller bottle
&tested at 30 L bioreactor scale

CONCLUSIONS

The concurrent roller bottle process development was successfully achieved and it is equivalent to the bioreactor process described above in terms of potency measured as TCID50/mL. Critical parameters for H-I, H-II and H-III at target were successfully reproduced in the concurrent roller process.

The preferred embodiments for the roller bottle concurrent process for EU PRRS 94881 MLV are as follows for virus propagation, HARVEST-I: Media composition MEM with 1.4 g/L Sodium bicarbonate; Plant cells at $1\times10^7/850$ cm$^2$ Corning Roller bottle with 400 mL of media supplemented with 20 mL of Fetal Bovine Serum 5% v/v (range: $7\times10^6$-$2\times10^7$/roller bottle); Temperature controlled at $36\pm1°$ C.; Roller bottle rack speed is 0.5 RPM; and Target MOI is 0.1.

For harvest-I criterion, start sampling for offline dextrose measurements on day 5 PI. Harvest-I should be performed when dextrose is ≤0.1 g/which usually occurs between 5-7 days PI. However, if a second harvest is to be performed, first re-fee HARVEST II.

II. First Re-Feed—HARVEST-II

Re-Feed with 400 mL of media composition MEM, and 1.4 g/L Sodium bicarbonate supplemented with 20 mL of Fetal Bovine Serum (5% v/v). Perform Re-Feed under same conditions as the first harvest media set-up (see first harvest parameters above). Temperature control is to remain on at a set point of $36\pm1°$ C. Roller bottle rack speed is 0.5 RPM. Second Harvest of viral fluids occurs on day 2 post re-feed.

III. Second Re-Feed—HARVEST-III

Re-Feed with 400 mL of media composition MEM, Neomycin and 1.4 g/L Sodium bicarbonate supplemented with 20 mL of Irradiated Fetal Bovine Serum (5% v/v). Perform Re-Feed under the same conditions as the first harvest media set-up (see second harvest parameters above). Temperature control is to remain on at a set point of $36\pm1°$ C. Roller bottle rack speed is 0.5 RPM. Third Harvest of viral fluids occurs on day 2 post re-feed.

The invention claimed is:

1. A method for the commercial scale production of porcine reproductive and respiratory syndrome virus (PRRSV), in an amount in excess of 10 liters, comprising:
    a) concurrently seeding a large scale culture media with a mammalian cell line that is permissive to PRRSV infection into a bioreactor and infecting said mammalian cells with a PRRSV, wherein the culture media is added to the bioreactor before the mammalian cells and the PRRSV are later added concurrently;
    b) propagating virus for 5 to 7 days post infection;
    c) performing a first harvesting step by removing the media from said bioreactor and isolating propagated vim s therefrom;
    d) replenishing the media in said bioreactor and propagating virus for 1 to 4 days;
    e) performing a second harvesting step by removing the media from said bioreactor and isolating propagated virus therefrom;
    f) replenishing the media in said bioreactor and propagating virus for 1 to 4 days; and
    g) performing a third harvesting step by removing the media from said bioreactor and isolating propagated virus therefrom;
    wherein the PRRSV is PRRSV strain 94881.

2. The method of claim 1, further comprising at least one re-feeding step and at least one harvest step subsequent to the third harvesting step comprising replenishing the media in said bioreactor and propagating virus for 1 to 4 days and performing a fourth harvesting step by removing the media from said bioreactor and isolating propagated vim s therefrom.

3. The method of claim 1, wherein the target multiplicity of infection (MOI) is 0.01 to 0.30.

4. The method of claim 1, wherein said mammalian cells are planted at a density of about $7\times10^8$ to $1.0\times10^9$ per 300 L bioreactor.

5. The method of claim 4, wherein said cell planting density is about $1.0\times10^9$ per 300 L bioreactor.

6. The method of claim 5, wherein said cell planting density is about $7\times10^8$ virus particles per 300 L bioreactor.

7. The method of claim 1, comprising monitoring the dextrose concentration of said media wherein said first harvest step is performed on the first day when the dextrose concentration of the media decreases to less than 0.1 g/L.

8. The method of claim 1, wherein said second harvest is performed 1 or 2 days post-refeeding with media.

9. The method of claim 1, wherein the culture media is added to the bioreactor one day prior to or on the same day but prior to addition of said mammalian cell line and said PRRSV.

10. The method of claim 1, wherein the culture media is added to the bioreactor one day prior to the addition of said mammalian cell line and said PRRSV.

11. The method of claim 1, wherein the temperature of said bioreactor is set at between 34° C. and 38° C.

12. The method of claim 1, wherein said media comprises 5% v/v irradiated fetal calf serum.

13. A method for the commercial scale production of porcine reproductive and respiratory syndrome virus (PRRSV), in an amount in excess of 10 liters, comprising:
    a) concurrently seeding a large scale culture media with a mammalian cell line that is permissive to PRRSV infection into a bioreactor and infecting said mammalian cells with a PRRSV, wherein the culture media is added to the bioreactor before the mammalian cells and the PRRSV are later added concurrently;
    b) propagating virus for 5 to 7 days post infection;
    c) performing a first harvesting step by removing the media from said bioreactor and isolating propagated vim s therefrom;
    d) replenishing the media in said bioreactor and propagating virus for 1 to 4 days;
    e) performing a second harvesting step by removing the media from said bioreactor and isolating propagated virus therefrom;
    f) replenishing the media in said bioreactor and propagating virus for 1 to 4 days and
    g) performing a third harvesting step by removing the media from said bioreactor and isolating propagated vim s therefrom,
    wherein said PRRSV is PRRSV strain 94881.

14. The method of claim 1, wherein said mammalian cell line is selected from the group consisting of: porcine alveolar macrophage cells, MA-104 cells; baby hamster kidney cells; Chinese hamster ovary cells; African green monkey kidney cells; VERO cells; and CL2621 cells.

15. The method of claim 1, wherein the culture media is added to the bioreactor at least one day prior to the addition of said mammalian cell line and said PRRSV.

16. The method of claim 13, wherein the culture media is added to the bioreactor at least one day prior to the addition of said mammalian cell line and said PRRSV.

* * * * *